US008759612B2

(12) United States Patent
Li

(10) Patent No.: US 8,759,612 B2
(45) Date of Patent: Jun. 24, 2014

(54) SOYBEAN PROMOTERS LTP2 AND FLOWER-PREFERRED EXPRESSION THEREOF IN TRANSGENIC PLANTS

(75) Inventor: Zhongsen Li, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1182 days.

(21) Appl. No.: 12/152,369

(22) Filed: May 14, 2008

(65) Prior Publication Data

US 2008/0295201 A1 Nov. 27, 2008

Related U.S. Application Data

(60) Provisional application No. 60/930,878, filed on May 17, 2007.

(51) Int. Cl.
*A01H 5/00* (2006.01)
*C12N 15/82* (2006.01)
*C12N 15/87* (2006.01)

(52) U.S. Cl.
USPC ........ 800/287; 536/24.1; 800/278; 435/320.1

(58) Field of Classification Search
USPC .......................................... 800/287
See application file for complete search history.

(56) References Cited

U.S. PATENT DOCUMENTS

| | | | |
|---|---|---|---|
| 4,945,050 A | 7/1990 | Sanford et al. | |
| 5,004,863 A | 4/1991 | Umbeck | |
| 5,107,065 A | 4/1992 | Shewmaker et al. | |
| 5,159,135 A | 10/1992 | Umbeck | |
| 5,231,020 A | 7/1993 | Jorgensen et al. | |
| 5,416,011 A | 5/1995 | Hinchee et al. | |
| 5,463,174 A | 10/1995 | Moloney et al. | |
| 5,569,834 A | 10/1996 | Hinchee et al. | |
| 6,072,050 A | 6/2000 | Bowen et al. | |
| 2002/0042931 A1* | 4/2002 | Kaplan et al. ................. | 800/290 |

FOREIGN PATENT DOCUMENTS

| | | |
|---|---|---|
| WO | WO9217598 A1 | 10/1992 |
| WO | WO9836083 A1 | 8/1998 |
| WO | WO9953050 A1 | 10/1999 |
| WO | WO0037662 A2 | 6/2000 |
| WO | WO0200904 A2 | 1/2002 |

OTHER PUBLICATIONS

Odell et al., "Identification of DNA sequences required for activity of the cauliflower mosaic virus 35S promoter," Nature vol. 313. pp. 810-812 (1985).
P. R. Ebert et al., "Identification of an Essential upstream element in the nopaline synthase . . . ," Proc. Natl. Acad. Sci. U.S.A., vol. 84, pp. 5745-5749 (1987).
R. A. Jefferson et al., "GUS fusions: β-glucuronidase as a sensitive and versatile gene fusion marker in higher plants," EMBO J. vol. 6, No. 13, pp. 3901-3907 (1987).
Klein et al., "High-Velocity microprojectiles for delivering nucleic acids into living cells," Letter of Nature (London) vol. 327, pp. 70-73 (1987).
Lawton et al., "Expression of a soybean β-conclycinin gene under the control of the Cauliflower Mosiac Virus 35S and 19S . . . ," Plant Mol. Biol. 9:315-324 (1987).
J. C. Walker et al., "DNA sequences required for anaerobic expression of the maize alcohol dehydrogenase 1 gene," Proc. Natl. Acad. Sci. vol. 84, pp. 6624-6628 (1987).
Raschke et al., "Nucleotide Sequence Analysis of Soybean Small Heat Shock Protein Genes Belonging to two Different Multigene ..," J. Mol. Biol. 199(4), pp. 549-557 (1988).
V. L. Chandler et al., "Two Regulartory Genes of the Maize Anthocyanin Pathway Are Homologous: Isolation of B Utilizing R Genomic ..," Plant Cell, vol. 1, pp. 1175-1183 (1989).
J. K. Okamuro et al, "Regulation of plant gene expression: general principles," Biochemistry of Plants 15:1 82 (1989).
M. J. Battraw et al., "Histochemical analysis of CaMV 35S promoter-β-glucuronidase gene expression in transgenic rice plants," Plant Mol. Biol. 15:527-538 (1990).
J. Callis et al., "Ubiquitin Extension Proteins of *Arabidopsis thaliana*," J. Biol. Chem. 265(21):12486-12493 (1990).
Neuhaus et al., "Plants transformation by microinjection techniques," Physiol. Plant. 79:213-217 (1990).
M. Sanger et al., "Characteristics of a strong promoter from figwort mosaic virus: comparison with the analogous 35S promoter . . . ," Plant Mol. Biol. 14:433-443 (1990).
N. S. Yang et al., "Maize sucrose synthase-1 promoter directs phloem cell-specific expression of Gus gene ..," Proc. Natl. Acad. Sci. 87:4144-4148 (Jun. 1990).
Pelese-Siebenbourg et al., "A pair of genes coding for lipid-transfer proteins in *Sorghum vulgare*," Gene 148:305-308 (1994).
A. L. Plant et al., "Regulation of an *Arabidopsis* oleosin gene promoter in transgenic *Brassica napus*," Plant Mol. Biol. 25:193-205 (1994).
S. Thoma et al., Tissue-Specific Expression of a Gene Encoding a Cell Wall-Localized Lipid Transfer Protein from *Arabidopsis*, Plant Physiol. 105:35-45 (1994).
Vignols et al., "Characterization of a rice gene coding for a lipid transfer protein," Gene 142:265-270 (1994).
S. Holtorf et al., "Comparison of different constitutive and inducible promoters for the . . . *Arabidopsis thaliana*," Plant Mol. Biol. 29:637-646 (1995).
Pellegrineschi et al., "Expression of horseradish peroxidase in transgenic tobacco," Biochem. Soc. Trans. 23(2):247-250 (1995).
A. Wilmink et al., "Activity of constitutive promoters in various species from the Liliaceae," Plant Mol. Biol. 28:949-955 (1995).

(Continued)

*Primary Examiner* — Li Zheng

(57) ABSTRACT

The invention relates to gene expression regulatory sequences from soybean, specifically to the promoters of a soybean lipid transfer protein LTP2 and fragments thereof and their use in promoting the expression of one or more heterologous nucleic acid fragments in plants. The described LTP2 promoters preferentially initiate transcription in flower cells. The invention further discloses compositions, polynucleotide constructs, transformed host cells, transgenic plants and seeds containing the recombinant construct with the promoter, and methods for preparing and using the same.

Figure 1:
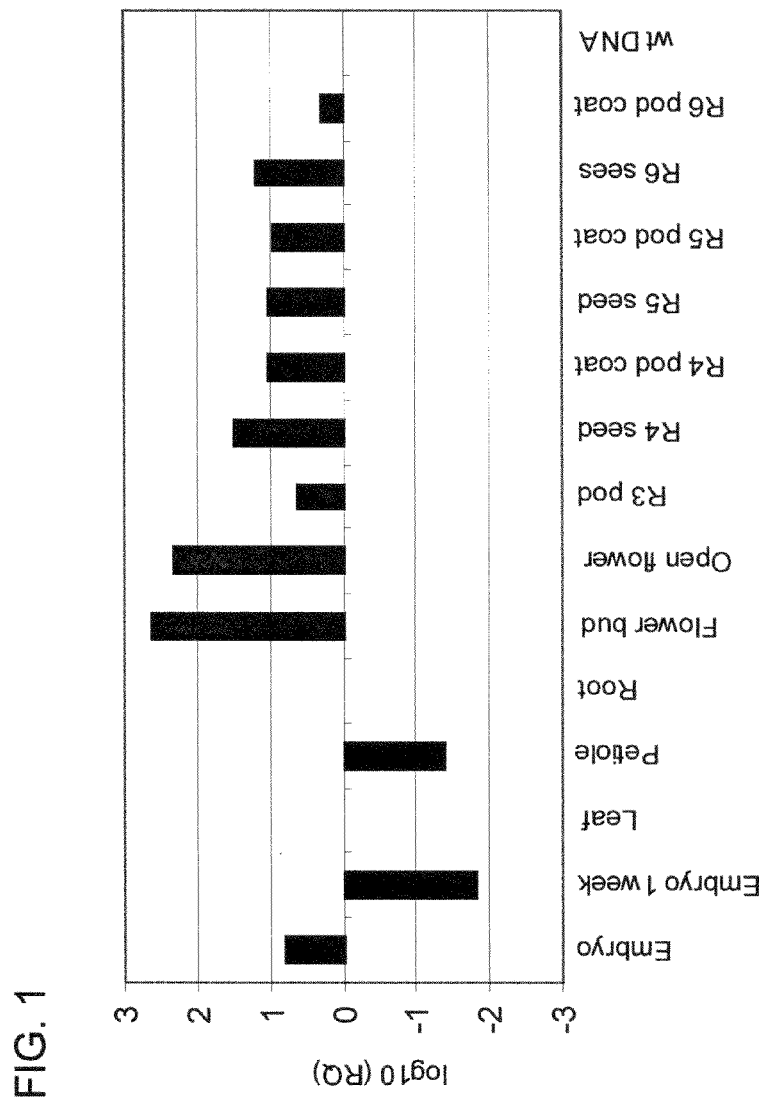

16 Claims, 7 Drawing Sheets
(2 of 7 Drawing Sheet(s) Filed in Color)

(56) References Cited

OTHER PUBLICATIONS

Jean-Claude Kader, "Lipid-Transfer Proteins in Plants," Annu. Rev. Plant Physiol. Plant Mol. Biol. 47: 627-654 (1996).

Zhongsen Li, "Iolation and Characterizationof *Arabidopsis*," Texas A&M Univ., May 1997.

M. A. J. Toonen et al., "AtLTP1 luciferase expression during carrot somatic embryogenesis," Plant Journal 12(5):1213-1221 (1997).

R. Atanassova et al., "Functional analysis of the promoter region of a maize (*Zea mays* L.) H3 histone gene in transgenic *Arabidopsis* . . . ," Plant Mol. Biol. 37:275-285 (1998).

T. Elmayan et al., "*Arabidopsis* Mutants Impaired in Cosuppression," Plant Cell 10:1747-1757 (Oct. 1998).

Rollfinke et al., "Characterization and expression of a heptaubiquitin gene from tomato," Gene 211:267-276 (1998).

A. K. Sohal et al., "The promoter of a *Brassica napus* lipid transfer protein gene is active in a range of tissues . . . transgenic *Arabidopsis*," Plant Mol. Biol. 41:75-87 (1999).

I. Sabala et al., "Tissue-specific expression of Pa18, a putative lipid transfer protein gene, during embryo . . . (*Picea abies*)," Plant Mol. Biol. 42:461-478 (2000).

H. Chang et al., "Overproduction of Cytokinins in *Petunia* Flowers Transformed with PSAG12-IPT Delays Corolla . . . Sensitivity to Ethylene," Plant Physiol. 132:2174-2183 (Aug. 2003).

T. Kakimoto, "Biosynthesis of cytokinins," J. Plant Res. 116:233-239 (2003).

E. Yubero-Serrano et al, "Identification of a strawberry gene encoding a non-specific lipid transnfer protein that responds to ABA, . . . ," J. Exp. Bot. 54:1865-1877 (2003).

C. Espinosa-Soto et al., "A Gene Regulatory Network Model for Cell-Fate Determination during *Arabidopsis* Gene Expression Profiles" Plant Cell 16:2923-2939 (Nov. 2004).

S. Mori et al., "Heterologous expression of the flavonoid 3,5,-hydroxylase gene of *Vinca major* alters transgenic *Petunia hybrida*," Plant Cell Reports 22:415-421 (2004).

T. E. Young et al., "Senescence-induced expression of cytokinin reverses pistil abortion during maize flower development," Plant Journal, 38:910-922 (2004).

M. L. Federico et al., "The complex development expression of a novel stress-responsive barley Ltp gene is determined by a . . . sequence," Plant Mol. Biol. 57:35-51 (2005).

Y. Tanaka et al., "Genetic engineering in floriculture," Plant Cell, Tissue and Organ Culture 80:1-24 (2005).

Copending U.S. Appl. No. 12/080,113, filed Mar. 31, 2008.

Copending U.S. Appl. No. 12/152,375, filed May 14, 2008.

\* cited by examiner 1771 bp LTP2 promoter

SEQUENCE LISTING

<160> NUMBER OF SEQ ID NOS: 50

<210> SEQ ID NO 1
<211> LENGTH: 1771
<212> TYPE: DNA
<213> ORGANISM: Glycine max

<400> SEQUENCE: 1

| | | | | | |
|---|---|---|---|---|---|
| gggatccatg | gtctcccaaa | attttaattc | taaaaatatt | gtatgtttat | caaaatttat | 60 |
| aagagggat | aaaacacttc | gtcaaaatta | agtcaatttt | acaatcttgt | ttgacaaatc | 120 |
| tcccactact | tattgcttat | taattaggtc | ttttataggc | aaaaaattac | aatacaataa | 180 |
| taatataaat | aaacctgcat | ccggaggaaa | acttaactga | gtattatatt | ataaactttt | 240 |
| tgattcaaat | tgtaatttca | tacatcaaat | ctcttgactc | atgagatata | aacttttttac | 300 |
| acacacatgt | aggcgaaggc | taaggtggga | gagcatatga | tgtatcccac | cataggaaac | 360 |
| tatctttttc | acccttatat | gatgtatccc | accataaggc | actttgcagg | gcaactgaca | 420 |
| aagattgata | actcaaagta | cctaaattac | tattattgag | aagcattgaa | tataacatgg | 480 |
| tctgttctac | ctaacccata | aatgttgatg | gttgcatact | tcagttgtta | catttaggaa | 540 |
| aagacagtta | cgaatatatc | atcacagtag | aataattaat | tctatttttt | ttttgtcata | 600 |
| gaatcttctt | actaattata | tcatcacttg | ttagatatag | aaaatattgg | atgttttaaa | 660 |
| agtttttaag | acataaaatg | tattctatt | aattttttt | tattataaaa | catcaagaag | 720 |
| atttataaga | aaatataaca | ttacttatta | taatactatc | attattcata | tttttttaaaa | 780 |
| aaatatctct | agctttatat | ttacgtgaat | atgaaattaa | agacatatat | gttttatctg | 840 |
| ttttattttt | tcagttttta | cttggtttga | aaataattat | caaaacataa | taaattagaa | 900 |
| agttacaaaa | tggtaaagaa | aaaactgaga | agagaaacaa | gcacgagttt | aatttctggt | 960 |
| gaagaattag | tttatcgttg | gcttcatacg | aatataacga | aaacagagta | ataaaatgtt | 1020 |
| acacagagta | atatacaaag | atagagatat | aagtagttga | taaaacaatt | gaaaaacgat | 1080 |
| gaaggaaaaa | aggtgaagag | agaactcatg | gattccaaac | ctcccattaa | catttacaac | 1140 |
| aaaattaaca | tttataatgt | cttagaaagt | atcatatcac | taaatgatct | aataaagaaa | 1200 |
| ggagttaatt | agacaaaaag | agaagaatat | aaaaataaaa | tgactacgca | tcatcaaata | 1260 |
| tcgaaaccaa | caatacttat | ggtgacttta | attaatgatt | tcggcagagt | tgaagtcgga | 1320 |
| aattataaac | aagttagtac | aaatttaagt | gcagccatat | gaaaactttt | aattcttagg | 1380 |
| aaagtggcag | catctcttag | ggctccaaaa | tcattttggg | ggaagcagaa | acctgccaag | 1440 |
| ccacatggct | ataaatatat | agaaacggat | gatcaagtta | gccaaccatt | atgaactctg | 1500 |
| atatacatat | ttgtctaaac | ctatagatat | atattcatta | attgtatcat | attgtaggtt | 1560 |
| tcagctaccc | cgcggtcatt | caattgcttg | catatgttaa | atgaaatcaa | tcagtaaaat | 1620 |
| tacctaccat | tccttcacct | ttcacctaac | aaactcaggt | tgaatctgta | ctctatattt | 1680 |
| agtccttaaa | ttctcaaatc | ataacattct | cactcactat | aactaaccat | tgaagaagtg | 1740 |
| caatttcgtc | ctctaacact | cttccaaatc | c | | | 1771 |

<210> SEQ ID NO 2
<211> LENGTH: 1384
<212> TYPE: DNA
<213> ORGANISM: Glycine max

<400> SEQUENCE: 2

| | | | | | |
|---|---|---|---|---|---|
| cccaccataa | ggcactttgc | agggcaactg | acaaagattg | ataactcaaa | gtacctaaat | 60 |

```
tactattatt gagaagcatt gaatataaca tggtctgttc tacctaaccc ataaatgttg      120
atggttgcat acttcagttg ttacatttag gaaaagacag ttacgaatat atcatcacag      180
tagaataatt aattctattt ttttttttgtc atagaatctt cttactaatt atatcatcac     240
ttgttagata tagaaaatat tggatgtttt aaaagttttt aagacataaa atgtattcta      300
tttaattttt ttttattata aaacatcaag aagatttata agaaaatata acattactta      360
ttataatact atcattattc atattttta aaaaaatatc tctagcttta tatttacgtg       420
aatatgaaat taaagacata tatgttttat ctgtttttat ttttcagttt ttacttggtt      480
tgaaaataat tatcaaaaca taataaatta gaaagttaca aatggtaaa gaaaaaactg       540 agaagagaaa caagcacgag tttaatttct ggtgaagaat tagtttatcg ttggcttcat      600
acgaatataa cgaaaacaga gtaataaaat gttacacaga gtaatataca aagatagaga     660
tataagtagt tgataaaaca attgaaaaac gatgaaggaa aaaaggtgaa gagagaactc     720
atggattcca aacctcccat taacatttac aacaaaatta acatttataa tgtcttagaa     780
agtatcatat cactaaatga tctaataaag aaaggagtta attagacaaa agagaagaa      840 tataaaaata aaatgactac gcatcatcaa atatcgaaac caacaatact tatggtgact     900
ttaattaatg atttcggcag agttgaagtc ggaaattata acaagttag tacaaattta      960 agtgcagcca tgaaaaact tttaattctt aggaaagtgg cagcatctct tagggctcca     1020 aaatcattt ggggggaagca gaaacctgcc aagccacatg gctataaata tatagaaacg    1080
gatgatcaag ttagccaacc attatgaact ctgatataca tatttgtcta aacctataga    1140
tatatattca ttaattgtat catattgtag gtttcagcta ccccgcggtc attcaattgc    1200
ttgcatatgt taaatgaaat caatcagtaa aattacctac cattccttca cctttcacct    1260
aacaaactca ggttgaatct gtactctata tttagtcctt aaattctcaa atcataacat    1320
tctcactcac tataactaac cattgaagaa gtgcaattt gtcctctaac actcttccaa      1380
atcc                                                                  1384

<210> SEQ ID NO 3
<211> LENGTH: 988
<212> TYPE: DNA
<213> ORGANISM: Glycine max

<400> SEQUENCE: 3
tatctctagc tttatattta cgtgaatatg aaattaaaga catatatgtt ttatctgttt       60
ttattttcca gttttactt ggtttgaaaa taattatcaa aacataataa attagaaagt       120
tacaaaatgg taagaaaaa actgagaaga gaaacaagca cgagtttaat ttctggtgaa      180
gaattagttt atcgttggct tcatacgaat ataacgaaaa cagagtaata aaatgttaca      240
cagagtaata tacaaagata gagatataag tagttgataa aacaattgaa aaacgatgaa      300
ggaaaaaagg tgaagagaga actcatggat tccaaacctc ccattaacat ttacaacaaa     360
attaacattt ataatgtctt agaaagtatc atatcactaa atgatctaat aaagaaagga     420
gttaattaga caaaagaga agaatataaa aataaaatga ctacgcatca tcaaatatcg      480
aaaccaacaa tacttatggt gactttaatt aatgatttcg gcagagttga agtcggaaat      540
tataaacaag ttagtacaaa tttaagtgca gccatgaaa aacttttaat tcttaggaaa      600
gtggcagcat ctcttagggc tccaaaatca ttttgggggga agcagaaacc tgccaagcca    660
catggctata aatatataga aacggatgat caagttagcc aaccattatg aactctgata     720
```

```
tacatatttg tctaaaccta tagatatata ttcattaatt gtatcatatt gtaggtttca      780
gctaccccgc ggtcattcaa ttgcttgcat atgttaaatg aaatcaatca gtaaaattac      840
ctaccattcc ttcacctttc acctaacaaa ctcaggttga atctgtactc tatatttagt      900
ccttaaattc tcaaatcata acattctcac tcactataac taaccattga agaagtgcaa      960
tttcgtcctc taacactctt ccaaatcc                                         988

<210> SEQ ID NO 4
<211> LENGTH: 682
<212> TYPE: DNA
<213> ORGANISM: Glycine max

<400> SEQUENCE: 4
aaggtgaaga gagaactcat ggattccaaa cctcccatta acatttacaa caaaattaac       60
atttataatg tcttagaaag tatcatatca ctaaatgatc taataagaa aggagttaat      120 tagacaaaaa gagaagaata taaaaataaa atgactacgc atcatcaaat atcgaaacca      180
acaatactta tggtgacttt aattaatgat ttcggcagag ttgaagtcgg aaattataaa      240
caagttagta caaatttaag tgcagccata tgaaaacttt taattcttag gaaagtggca      300
gcatctctta gggctccaaa atcattttgg gggaagcaga aacctgccaa gccacatggc      360
tataaatata tagaaacgga tgatcaagtt agccaaccat tatgaactct gatatacata      420
tttgtctaaa cctatagata tatattcatt aattgtatca tattgtaggt ttcagctacc      480
ccgcggtcat tcaattgctt gcatatgtta aatgaaatca atcagtaaaa ttacctacca      540
ttccttcacc tttcacctaa caaactcagg ttgaatctgt actctatatt tagtccttaa      600
attctcaaat cataacattc tcactcacta taactaacca ttgaagaagt gcaatttcgt      660
cctctaacac tcttccaaat cc                                               682

<210> SEQ ID NO 5
<211> LENGTH: 393
<212> TYPE: DNA
<213> ORGANISM: Glycine max

<400> SEQUENCE: 5
ggaaagtggc agcatctctt agggctccaa atcattttg ggggaagcag aaacctgcca       60
agccacatgg ctataaatat atagaaacgg atgatcaagt tagccaacca ttatgaactc      120
tgatatacat atttgtctaa acctatagat atatattcat taattgtatc atattgtagg      180
tttcagctac cccgcggtca ttcaattgct tgcatatgtt aaatgaaatc aatcagtaaa      240
attacctacc attccttcac ctttcaccta acaaactcag gttgaatctg tactctatat      300
ttagtcctta aattctcaaa tcataacatt ctcactcact ataactaacc attgaagaag      360
tgcaatttcg tcctctaaca ctcttccaaa tcc                                   393

<210> SEQ ID NO 6
<211> LENGTH: 224
<212> TYPE: DNA
<213> ORGANISM: Glycine max

<400> SEQUENCE: 6
catattgtag gtttcagcta ccccgcggtc attcaattgc ttgcatatgt aaatgaaat       60 caatcagtaa aattacctac cattccttca cctttcacct aacaaactca ggttgaatct      120
gtactctata tttagtcctt aaattctcaa atcataacat tctcactcac tataactaac      180
cattgaagaa gtgcaatttc gtcctctaac actcttccaa atcc                       224
```

<210> SEQ ID NO 7
<211> LENGTH: 27
<212> TYPE: DNA
<213> ORGANISM: Artificial
<220> FEATURE:
<223> OTHER INFORMATION: Primer

<400> SEQUENCE: 7
ggatttggaa gagtgttaga ggacgaa                                              27

<210> SEQ ID NO 8
<211> LENGTH: 22
<212> TYPE: DNA
<213> ORGANISM: Artificial
<220> FEATURE:
<223> OTHER INFORMATION: Primer

<400> SEQUENCE: 8
cccaccataa ggcactttgc ag                                                   22

<210> SEQ ID NO 9
<211> LENGTH: 32
<212> TYPE: DNA
<213> ORGANISM: Artificial
<220> FEATURE:
<223> OTHER INFORMATION: Primer

<400> SEQUENCE: 9
tatctctagc tttatattta cgtgaatatg aa                                        32

<210> SEQ ID NO 10
<211> LENGTH: 27
<212> TYPE: DNA
<213> ORGANISM: Artificial
<220> FEATURE:
<223> OTHER INFORMATION: Primer

<400> SEQUENCE: 10
aaggtgaaga gagaactcat ggattcc                                              27

<210> SEQ ID NO 11
<211> LENGTH: 24
<212> TYPE: DNA
<213> ORGANISM: Artificial
<220> FEATURE:
<223> OTHER INFORMATION: Primer

<400> SEQUENCE: 11
ggaaagtggc agcatctctt aggg                                                 24

<210> SEQ ID NO 12
<211> LENGTH: 26
<212> TYPE: DNA
<213> ORGANISM: Artificial
<220> FEATURE:
<223> OTHER INFORMATION: Primer

<400> SEQUENCE: 12
catattgtag gtttcagcta ccccgc                                               26

<210> SEQ ID NO 13
<211> LENGTH: 23
<212> TYPE: DNA
<213> ORGANISM: Artificial
<220> FEATURE:

<223> OTHER INFORMATION: Primer

<400> SEQUENCE: 13
agctggcaac cctcacaagc agt                                             23

<210> SEQ ID NO 14
<211> LENGTH: 25
<212> TYPE: DNA
<213> ORGANISM: Artificial
<220> FEATURE:
<223> OTHER INFORMATION: Primer

<400> SEQUENCE: 14
gtaatacgac tcactatagg gcacg                                           25

<210> SEQ ID NO 15
<211> LENGTH: 32
<212> TYPE: DNA
<213> ORGANISM: Artificial
<220> FEATURE:
<223> OTHER INFORMATION: Primer

<400> SEQUENCE: 15
gccatggatt tggaagagtg ttagaggacg aa                                   32

<210> SEQ ID NO 16
<211> LENGTH: 22
<212> TYPE: DNA
<213> ORGANISM: Artificial
<220> FEATURE:
<223> OTHER INFORMATION: Primer

<400> SEQUENCE: 16
ctatagggca cgcgtggtcg ac                                              22

<210> SEQ ID NO 17
<211> LENGTH: 629
<212> TYPE: DNA
<213> ORGANISM: Glycine max

<400> SEQUENCE: 17
cacgagtgaa gaagtgcaat ttcgtcctct aacactcttc caaatcatgg ctagctcact     60
gcttgtgagg gttgccagct gcatggttgt ggtgtggatg tttagttttg ggcacataat    120
tcccttggca gaagctgaaa ttccatgtgg cagggtgcaa atcactgtgg ctccatgcat    180
agggtaccta aggggtcctg gtggaggtgt ccctgcacca tgctgcaatg gggttaagag    240
cataaacaac caagccaaaa ccaccccaga tcgtcaaggg gtgtgtaggt gcctcaaaag    300
cactgttttg agcttggctg gactcaatct tgcaacccttt tcagccctcc ctagcaagtg    360
tgggatcaac ttgccctaca agatcacccc caccattgat tgcaacacgg taaagtactg    420
acagtttgct cgagggtttt acgcttgttg actttacact tgtttcgcag taataaccag    480
caaaagaggg aataaagatg gtttaatttc ctccattgtt tggatcccac tagggagtat    540
aataatgttg attgtccaaa atgacatata ttggattttc tgtcactaat atacaagaaa    600
aaaaaaaaaa aaaaaaaaa aaaaaaaa                                       629

<210> SEQ ID NO 18
<211> LENGTH: 124
<212> TYPE: PRT
<213> ORGANISM: Glycine max

<400> SEQUENCE: 18

```
Met Ala Ser Ser Leu Leu Val Arg Val Ala Ser Cys Met Val Val
1               5                   10                  15

Trp Met Phe Ser Phe Gly His Ile Ile Pro Leu Ala Glu Ala Glu Ile
                20                  25                  30

Pro Cys Gly Arg Val Gln Ile Thr Val Ala Pro Cys Ile Gly Tyr Leu
            35                  40                  45

Arg Gly Pro Gly Gly Gly Val Pro Ala Pro Cys Cys Asn Gly Val Lys
        50                  55                  60

Ser Ile Asn Asn Gln Ala Lys Thr Thr Pro Asp Arg Gln Gly Val Cys
65                  70                  75                  80

Arg Cys Leu Lys Ser Thr Val Leu Ser Leu Ala Gly Leu Asn Leu Ala
                85                  90                  95

Thr Leu Ser Ala Leu Pro Ser Lys Cys Gly Ile Asn Leu Pro Tyr Lys
            100                 105                 110

Ile Thr Pro Thr Ile Asp Cys Asn Thr Val Lys Tyr
        115                 120

<210> SEQ ID NO 19
<211> LENGTH: 26
<212> TYPE: DNA
<213> ORGANISM: Artificial
<220> FEATURE:
<223> OTHER INFORMATION: Primer

<400> SEQUENCE: 19
gaccaagaca cactcgttca tatatc                                          26

<210> SEQ ID NO 20
<211> LENGTH: 25
<212> TYPE: DNA
<213> ORGANISM: Artificial
<220> FEATURE:
<223> OTHER INFORMATION: Primer

<400> SEQUENCE: 20
tctgctgctc aatgtttaca aggac                                           25

<210> SEQ ID NO 21
<211> LENGTH: 48
<212> TYPE: DNA
<213> ORGANISM: Artificial
<220> FEATURE:
<223> OTHER INFORMATION: Longer strand sequence of the adaptor supplied
      in GenomeWalker(tm) kit

<400> SEQUENCE: 21
gtaatacgac tcactatagg gcacgcgtgg tcgacggccc gggctggt                  48

<210> SEQ ID NO 22
<211> LENGTH: 17
<212> TYPE: DNA
<213> ORGANISM: Artificial
<220> FEATURE:
<223> OTHER INFORMATION: MPSS tag sequence

<400> SEQUENCE: 22
gatcccacta gggagta                                                    17

<210> SEQ ID NO 23
<211> LENGTH: 21
<212> TYPE: DNA
<213> ORGANISM: Artificial
```

```
<220> FEATURE:
<223> OTHER INFORMATION: Primer

<400> SEQUENCE: 23
ccctagcaag tgtgggatca a                                         21

<210> SEQ ID NO 24
<211> LENGTH: 25
<212> TYPE: DNA
<213> ORGANISM: Artificial
<220> FEATURE:
<223> OTHER INFORMATION: Primer

<400> SEQUENCE: 24
tcagtacttt accgtgttgc aatca                                     25

<210> SEQ ID NO 25
<211> LENGTH: 24
<212> TYPE: DNA
<213> ORGANISM: Artificial
<220> FEATURE:
<223> OTHER INFORMATION: Primer

<400> SEQUENCE: 25
catgattggg agaaacctta agct                                      24

<210> SEQ ID NO 26
<211> LENGTH: 20
<212> TYPE: DNA
<213> ORGANISM: Artificial
<220> FEATURE:
<223> OTHER INFORMATION: Primer

<400> SEQUENCE: 26
agattgggcc agaggatcct                                           20

<210> SEQ ID NO 27
<211> LENGTH: 22
<212> TYPE: DNA
<213> ORGANISM: Artificial
<220> FEATURE:
<223> OTHER INFORMATION: Primer

<400> SEQUENCE: 27
ggaagaagag aatcgggtgg tt                                        22

<210> SEQ ID NO 28
<211> LENGTH: 23
<212> TYPE: DNA
<213> ORGANISM: Artificial
<220> FEATURE:
<223> OTHER INFORMATION: FAM labeled fluorescent DNA oligo probe

<400> SEQUENCE: 28
attgtgttgt gtggcatggt tat                                       23

<210> SEQ ID NO 29
<211> LENGTH: 23
<212> TYPE: DNA
<213> ORGANISM: Artificial
<220> FEATURE:
<223> OTHER INFORMATION: Primer

<400> SEQUENCE: 29
ggcttgttgt gcagtttttg aag                                       23
```

```
<210> SEQ ID NO 30
<211> LENGTH: 20
<212> TYPE: DNA
<213> ORGANISM: Artificial
<220> FEATURE:
<223> OTHER INFORMATION: Primer

<400> SEQUENCE: 30
aacggccaca agttcgtgat                                                   20

<210> SEQ ID NO 31
<211> LENGTH: 20
<212> TYPE: DNA
<213> ORGANISM: Artificial
<220> FEATURE:
<223> OTHER INFORMATION: FAM labeled fluorescent DNA oligo probe

<400> SEQUENCE: 31
accggcgagg gcatcggcta                                                   20

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
cttcaagggc aagcagacca                                                   20

<210> SEQ ID NO 33
<211> LENGTH: 24
<212> TYPE: DNA
<213> ORGANISM: Artificial
<220> FEATURE:
<223> OTHER INFORMATION: Primer

<400> SEQUENCE: 33
caaacttgac aaagccacaa ctct                                              24

<210> SEQ ID NO 34
<211> LENGTH: 20
<212> TYPE: DNA
<213> ORGANISM: Artificial
<220> FEATURE:
<223> OTHER INFORMATION: VIC labeled fluorescent DNA oligo probe

<400> SEQUENCE: 34
ctctcatctc atataaatac                                                   20

<210> SEQ ID NO 35
<211> LENGTH: 21
<212> TYPE: DNA
<213> ORGANISM: Artificial
<220> FEATURE:
<223> OTHER INFORMATION: Primer

<400> SEQUENCE: 35
ggagaaattg gtgtcgtgga a                                                 21

<210> SEQ ID NO 36
<211> LENGTH: 21
<212> TYPE: DNA
<213> ORGANISM: Artificial
<220> FEATURE:
<223> OTHER INFORMATION: Recombination site attB1 sequence
```

<400> SEQUENCE: 36
caagtttgta caaaaaagca g        21

<210> SEQ ID NO 37
<211> LENGTH: 21
<212> TYPE: DNA
<213> ORGANISM: Artificial
<220> FEATURE:
<223> OTHER INFORMATION: Recombination site attB2 sequence

<400> SEQUENCE: 37
cagctttctt gtacaaagtg g        21

<210> SEQ ID NO 38
<211> LENGTH: 3291
<212> TYPE: DNA
<213> ORGANISM: Artificial
<220> FEATURE:
<223> OTHER INFORMATION: Nucleotide sequence of QC299

<400> SEQUENCE: 38
tcgacccggg atccatggcc cacagcaagc acggcctgaa ggaggagatg accatgaagt        60
accacatgga gggctgcgtg aacggccaca gttcgtgat caccggcgag ggcatcggct       120
accccttcaa gggcaagcag accatcaacc tgtgcgtgat cgaggcggc cccctgccct       180 tcagcgagga catcctgagc gccggcttca gtacggcga ccggatcttc accgagtacc       240
cccaggacat cgtggactac ttcaagaaca gctgccccgc cggctacacc tggggccgga       300
gcttcctgtt cgaggacggc gccgtgtgca tctgtaacgt ggacatcacc gtgagcgtga       360
aggagaactg catctaccac aagagcatct tcaacggcgt gaacttcccc gccgacggcc       420
ccgtgatgaa gaagatgacc accaactggg aggccagctg cgagaagatc atgcccgtgc       480
ctaagcaggg catcctgaag gcgacgtga gcatgtacct gctgctgaag gacggcggcc       540
ggtaccggtg ccagttcgac accgtgtaca aggccaagag cgtgcccagc aagatgcccg       600
agtggcactt catccagcac aagctgctgc gggaggaccg gagcgacgcc aagaaccaga       660
agtggcagct gaccgagcac gccatcgcct tccccagcgc cctggcctga gagctcgaat       720
ttccccgatc gttcaaacat ttggcaataa agtttcttaa gattgaatcc tgttgccggt       780
cttgcgatga ttatcatata atttctgttg aattacgtta agcatgtaat aattaacatg       840
taatgcatga cgttatttat gagatgggtt tttatgatta gagtcccgca attatacatt       900
taatacgcga tagaaaacaa aatatagcgc gcaaactagg ataaattatc gcgcgcggtg       960
tcatctatgt tactagatcg ggaattctag tggccggccc agctgatatc catcacactg      1020
gcggccgcac tcgagatatc tagacccagc tttcttgtac aaagttggca ttataagaaa      1080
gcattgctta tcaatttgtt gcaacgaaca ggtcactatc agtcaaaata aaatcattat      1140
ttgccatcca gctgcagctc tggcccgtgt ctcaaaatct ctgatgttac attgcacaag      1200
ataaaaatat atcatcatga acaataaaac tgtctgctta cataaacagt aatacaaggg      1260
gtgttatgag ccatattcaa cgggaaacgt cgaggccgcg attaaattcc aacatggatg      1320
ctgatttata tgggtataaa tgggctcgcg ataatgtcgg gcaatcaggt gcgacaatct      1380
atcgcttgta tgggaagccc gatgcgccag agttgtttct gaaacatggc aaaggtagcg      1440
ttgccaatga tgttacagat gagatggtca gactaaactg gctgacggaa tttatgcctc      1500
ttccgaccat caagcatttt atccgtactc ctgatgatgc atggttactc accactgcga      1560

| | |
|---|---|
| tccccggaaa aacagcattc caggtattag aagaatatcc tgattcaggt gaaaatattg | 1620 |
| ttgatgcgct ggcagtgttc ctgcgccggt tgcattcgat tcctgtttgt aattgtcctt | 1680 |
| ttaacagcga tcgcgtattt cgtctcgctc aggcgcaatc acgaatgaat aacggtttgg | 1740 |
| ttgatgcgag tgattttgat gacgagcgta atggctggcc tgttgaacaa gtctggaaag | 1800 |
| aaatgcataa acttttgcca ttctcaccgg attcagtcgt cactcatggt gatttctcac | 1860 |
| ttgataacct tattttttgac gagggggaaat taataggttg tattgatgtt ggacgagtcg | 1920 |
| gaatcgcaga ccgataccag gatcttgcca tcctatggaa ctgcctcggt gagttttctc | 1980 |
| cttcattaca gaaacggctt tttcaaaaat atggtattga taatcctgat atgaataaat | 2040 |
| tgcagtttca tttgatgctc gatgagtttt tctaatcaga attggttaat tggttgtaac | 2100 |
| attattcaga ttgggccccg ttccactgag cgtcagaccc cgtagaaaag atcaaaggat | 2160 |
| cttcttgaga tcctttttttt ctgcgcgtaa tctgctgctt gcaaacaaaa aaaccaccgc | 2220 |
| taccagcggt ggtttgtttg ccggatcaag agctaccaac tcttttttccg aaggtaactg | 2280 |
| gcttcagcag agcgcagata ccaaatactg ttcttctagt gtagccgtag ttaggccacc | 2340 |
| acttcaagaa ctctgtagca ccgcctacat acctcgctct gctaatcctg ttaccagtgg | 2400 |
| ctgctgccag tggcgataag tcgtgtctta ccgggttgga ctcaagacga tagttaccgg | 2460 |
| ataaggcgca gcggtcgggc tgaacggggg gttcgtgcac acagcccagc ttggagcgaa | 2520 |
| cgacctacac cgaactgaga tacctacagc gtgagctatg agaaagcgcc acgcttcccg | 2580 |
| aagggagaaa ggcggacagg tatccggtaa gcggcagggt cggaacagga gagcgcacga | 2640 |
| gggagcttcc agggggaaac gcctggtatc tttatagtcc tgtcgggttt cgccacctct | 2700 |
| gacttgagcg tcgatttttg tgatgctcgt caggggggcg gagcctatgg aaaaacgcca | 2760 |
| gcaacgcggc cttttttacgg ttcctggcct tttgctggcc ttttgctcac atgttctttc | 2820 |
| ctgcgttatc ccctgattct gtggataacc gtattaccgc tagcatggat ctcggggacg | 2880 |
| tctaactact aagcgagagt agggaactgc caggcatcaa ataaaacgaa aggctcagtc | 2940 |
| ggaagactgg gcctttcgtt ttatctgttg tttgtcggtg aacgctctcc tgagtaggac | 3000 |
| aaaatccgcc ggagcggatt tgaacgttgt gaagcaacgg cccggagggt ggcgggcagg | 3060 |
| acgcccgcca taaactgcca ggcatcaaac taagcagaag gccatcctga cggatggcct | 3120 |
| ttttgcgttt ctacaaactc ttcctgttag ttagttactt aagctcgggc cccaaataat | 3180 |
| gattttattt tgactgatag tgacctgttc gttgcaacaa attgataagc aatgcttttt | 3240 |
| tataatgcca actttgtaca aaaaagcagg ctggcgccgg aaccaattca g | 3291 |

<210> SEQ ID NO 39
<211> LENGTH: 5055
<212> TYPE: DNA
<213> ORGANISM: Artificial
<220> FEATURE:
<223> OTHER INFORMATION: Nucleotide sequence of QC301

<400> SEQUENCE: 39

| | |
|---|---|
| catggcccac agcaagcacg gcctgaagga ggagatgacc atgaagtacc acatggaggg | 60 |
| ctgcgtgaac ggccacaagt tcgtgatcac cggcgagggc atcggctacc ccttcaaggg | 120 |
| caagcagacc atcaacctgt gcgtgatcga gggcggcccc ctgcccttca gcgaggacat | 180 |
| cctgagcgcc ggcttcaagt acggcgaccg gatcttcacc gagtaccccc aggacatcgt | 240 |
| ggactacttc aagaacagct gccccgccgg ctacacctgg ggccggagct tcctgttcga | 300 |
| ggacggcgcc gtgtgcatct gtaacgtgga catcaccgtg agcgtgaagg agaactgcat | 360 |

```
ctaccacaag agcatcttca acggcgtgaa cttccccgcc gacggccccg tgatgaagaa    420
gatgaccacc aactgggagg ccagctgcga gaagatcatg cccgtgccta agcagggcat    480
cctgaagggc gacgtgagca tgtacctgct gctgaaggac ggcggccggt accggtgcca    540
gttcgacacc gtgtacaagg ccaagagcgt gcccagcaag atgcccgagt ggcacttcat    600
ccagcacaag ctgctgcggg aggaccggag cgacgccaag aaccagaagt ggcagctgac    660
cgagcacgcc atcgccttcc ccagcgccct ggcctgagag ctcgaatttc cccgatcgtt    720
caaacatttg gcaataaagt ttcttaagat tgaatcctgt tgccggtctt gcgatgatta    780
tcatataatt tctgttgaat tacgttaagc atgtaataat taacatgtaa tgcatgacgt    840
tatttatgag atgggttttt atgattagag tcccgcaatt atacatttaa tacgcgatag    900
aaaacaaaat atagcgcgca aactaggata aattatcgcg cgcggtgtca tctatgttac    960
tagatcggga attctagtgg ccggcccagc tgatatccat cacactggcg ccgcactcg   1020
agatatctag acccagcttt cttgtacaaa gttggcatta taagaaagca ttgcttatca   1080
atttgttgca acgaacaggt cactatcagt caaaataaaa tcattatttg ccatccagct   1140
gcagctctgg cccgtgtctc aaaatctctg atgttacatt gcacaagata aaaatatatc   1200
atcatgaaca ataaaactgt ctgcttacat aaacagtaat acaaggggtg ttatgagcca   1260
tattcaacgg gaaacgtcga ggccgcgatt aaattccaac atggatgctg atttatatgg   1320
gtataaatgg gctcgcgata atgtcgggca atcaggtgcg acaatctatc gcttgtatgg   1380
gaagcccgat gcgccagagt tgtttctgaa acatggcaaa ggtagcgttg ccaatgatgt   1440
tacagatgag atggtcagac taaactggct gacggaattt atgcctcttc cgaccatcaa   1500
gcattttatc cgtactcctg atgatgcatg gttactcacc actgcgatcc ccggaaaaac   1560
agcattccag gtattagaag aatatcctga ttcaggtgaa atattgttg atgcgctggc   1620
agtgttcctg cgccggttgc attcgattcc tgtttgtaat tgtccttta acagcgatcg   1680
cgtatttcgt ctcgctcagg cgcaatcacg aatgaataac ggtttggttg atgcgagtga   1740
ttttgatgac gagcgtaatg gctggcctgt tgaacaagtc tggaaagaaa tgcataaact   1800
tttgccattc tcaccggatt cagtcgtcac tcatggtgat ttctcacttg ataaccttat   1860
ttttgacgag gggaaattaa taggttgtat tgatgttgga cgagtcggaa tcgcagaccg   1920
ataccaggat cttgccatcc tatggaactg cctcggtgag ttttctcctt cattacagaa   1980
acggcttttt caaaaatatg gtattgataa tcctgatatg aataaattgc agtttcattt   2040
gatgctcgat gagtttttct aatcagaatt ggttaattgg ttgtaacatt attcagattg   2100
ggccccgttc cactgagcgt cagaccccgt agaaaagatc aaaggatctt cttgagatcc   2160
ttttttctg cgcgtaatct gctgcttgca acaaaaaaa ccaccgctac cagcggtggt   2220
ttgtttgccg gatcaagagc taccaactct ttttccgaag gtaactggct tcagcagagc   2280
gcagatacca aatactgttc ttctagtgta gccgtagtta ggccaccact tcaagaactc   2340
tgtagcaccg cctacatacc tcgctctgct aatcctgtta ccagtggctg ctgccagtgg   2400
cgataagtcg tgtcttaccg ggttggactc aagacgatag ttaccggata aggcgcagcg   2460
gtcgggctga acggggggtt cgtgcacaca gcccagcttg gagcgaacga cctacaccga   2520
actgagatac ctacagcgtg agctatgaga aagcgccacg cttcccgaag ggagaaaggc   2580
ggacaggtat ccggtaagcg gcagggtcgg aacaggagag cgcacgaggg agcttccagg   2640
gggaaacgcc tggtatcttt atagtcctgt cgggtttcgc cacctctgac ttgagcgtcg   2700
```

-continued

```
attttttgtga tgctcgtcag gggggcggag cctatggaaa aacgccagca acgcggcctt    2760
tttacggttc ctggccttt  gctggccttt tgctcacatg ttctttcctg cgttatcccc    2820
tgattctgtg gataaccgta ttaccgctag catggatctc ggggacgtct aactactaag    2880
cgagagtagg gaactgccag gcatcaaata aaacgaaagg ctcagtcgga agactgggcc    2940
tttcgtttta tctgttgttt gtcggtgaac gctctcctga gtaggacaaa tccgccggga    3000
gcggatttga acgttgtgaa gcaacggccc ggagggtggc gggcaggacg cccgccataa    3060
actgccaggc atcaaactaa gcagaaggcc atcctgacgg atggcctttt tgcgtttcta    3120
caaactcttc ctgttagtta gttacttaag ctcgggcccc aaataatgat tttattttga    3180
ctgatagtga cctgttcgtt gcaacaaatt gataagcaat gcttttttat aatgccaact    3240
ttgtacaaaa aagcaggctg cgccggaac  caattcagtc gacccgggat ccatggtctc    3300
ccaaaatttt aattctaaaa atattgtatg tttatcaaaa tttataagag gggataaaac    3360
acttcgtcaa aattaagtca attttacaat cttgtttgac aaatctccca ctacttattg    3420
cttattaatt aggtctttta taggcaaaaa attacaatac aataataata taaataaacc    3480
tgcatccgga ggaaaactta actgagtatt atattatata acttttgatt caaattgtaa    3540
tttcatacat caaatctctt gactcatgag atataaactt tttacacaca catgtaggcg    3600
aaggctaagg tgggagagca tatgatgtat cccaccatag gaaactatct ttttcacccct   3660 tatatgagt  atcccaccat aaggcacttt gcagggcaac tgacaaagat tgataactca    3720
aagtacctaa attactatta ttgagaagca ttgaatataa catggtctgt tctacctaac    3780
ccataaatgt tgatggttgc atacttcagt tgttacattt aggaaaagac agttacgaat    3840
atatcatcac agtagaataa ttaattctat tttttttttg tcatagaatc ttcttactaa    3900
ttatatcatc acttgttaga tatagaaaat attggatgtt ttaaaagttt ttaagacata    3960
aaatgtattc tatttaattt tttttttatta taaaacatca agaagattta taagaaaata   4020
taacattact tattataata ctatcattat tcatatttt  taaaaaaata tctctagctt    4080
tatatttacg tgaatatgaa attaaagaca tatatgtttt atctgttttt atttttcagt    4140
ttttacttgg tttgaaaata attatcaaaa cataataaat tagaaagtta caaaatggta    4200
aagaaaaaac tgagaagaga acaagcacg  agtttaattt ctggtgaaga attagtttat    4260
cgttggcttc atacgaatat aacgaaaaca gagtaataaa atgttacaca gagtaatata    4320
caaagataga gatataagta gttgataaaa caattgaaaa acgatgaagg aaaaaaggtg    4380
aagagagaac tcatggattc caaacctccc attaacattt acaacaaaat taacatttat    4440
aatgtcttag aaagtatcat atcactaaat gatctaataa agaaaggagt taattagaca    4500
aaaagagaag aatataaaaa taaaatgact acgcatcatc aaatatcgaa accaacaata    4560
cttatggtga ctttaattaa tgatttcggc agagttgaag tcggaaatta taaacaagtt    4620
agtacaaatt taagtgcagc catatgaaaa cttttaattc ttaggaaagt ggcagcatct    4680
cttagggctc caaaatcatt ttgggggaag cagaaacctg ccaagccaca tggctataaa    4740
tatatagaaa cggatgatca agttagccaa ccattatgaa ctctgatata catatttgtc    4800
taaacctata gatatatatt cattaattgt atcatattgt aggtttcagc tacccgcgg    4860 tcattcaatt gcttgcatat gttaaatgaa atcaatcagt aaaattaccct accattcctt    4920 cacctttcac ctaacaaact caggttgaat ctgtactcta tatttagtcc ttaaattctc    4980
aaatcataac attctcactc actataacta accattgaag aagtgcaatt tcgtcctcta    5040
acactcttcc aaatc                                                    5055
```

<210> SEQ ID NO 40
<211> LENGTH: 8187
<212> TYPE: DNA
<213> ORGANISM: Artificial
<220> FEATURE:
<223> OTHER INFORMATION: Nucleotide sequence of PHP25224

<400> SEQUENCE: 40

| | | | | | | |
|---|---|---|---|---|---|---|
| cgcgcgtttc | ggtgatgacg | gtgaaaacct | ctgacacatg | cagctcccgg | agacggtcac | 60 |
| agcttgtctg | taagcggatg | ccgggagcag | acaagcccgt | cagggcgcgt | cagcgggtgt | 120 |
| tggcgggtgt | cggggctggc | ttaactatgc | ggcatcagag | cagattgtac | tgagagtgca | 180 |
| ccatatggac | atattgtcgt | tagaacgcgg | ctacaattaa | tacataacct | tatgtatcat | 240 |
| acacatacga | tttaggtgac | actatagaac | ggcgcgccgg | taccgggccc | cccctcgagt | 300 |
| gcggccgcaa | gcttgtcgac | ggagatcacc | actttgtaca | agaaagctga | acgagaaacg | 360 |
| taaaatgata | taaatatcaa | tatattaaat | tagattttgc | ataaaaaaca | gactacataa | 420 |
| tactgtaaaa | cacaacatat | ccagtcacta | tggtcgacct | gcagactggc | tgtgtataag | 480 |
| ggagcctgac | atttatattc | cccagaacat | caggttaatg | gcgttttga | tgtcattttc | 540 |
| gcggtggctg | agatcagcca | cttcttcccc | gataacggag | accggcacac | tggccatatc | 600 |
| ggtggtcatc | atgcgccagc | tttcatcccc | gatatgcacc | accgggtaaa | gttcacggga | 660 |
| gactttatct | gacagcagac | gtgcactggc | caggggatc | accatccgtc | gcccgggcgt | 720 |
| gtcaataata | tcactctgta | catccacaaa | cagacgataa | cggctctctc | ttttataggt | 780 |
| gtaaaccta | aactgcattt | caccagtccc | tgttctcgtc | agcaaaagag | ccgttcattt | 840 |
| caataaaccg | ggcgacctca | gccatcccctt | cctgattttc | cgctttccag | cgttcggcac | 900 |
| gcagacgacg | ggcttcattc | tgcatggttg | tgcttaccag | accggagata | ttgacatcat | 960 |
| atatgccttg | agcaactgat | agctgtcgct | gtcaactgtc | actgtaatac | gctgcttcat | 1020 |
| agcacacctc | tttttgacat | acttcgggta | tacatatcag | tatatattct | tataccgcaa | 1080 |
| aaatcagcgc | gcaaatacgc | atactgttat | ctggctttta | gtaagccgga | tccacgcgtt | 1140 |
| tacgccccgc | cctgccactc | atcgcagtac | tgttgtaatt | cattaagcat | tctgccgaca | 1200 |
| tggaagccat | cacagacggc | atgatgaacc | tgaatcgcca | gcggcatcag | caccttgtcg | 1260 |
| ccttgcgtat | aatatttgcc | catggtgaaa | acggggcga | agaagttgtc | catattggcc | 1320 |
| acgtttaaat | caaaactggt | gaaactcacc | cagggattgg | ctgagacgaa | aaacatattc | 1380 |
| tcaataaacc | ctttagggaa | ataggccagg | ttttcaccgt | aacacgccac | atcttgcgaa | 1440 |
| tatatgtgta | gaaactgccg | gaaatcgtcg | tggtattcac | tccagagcga | tgaaaacgtt | 1500 |
| tcagtttgct | catggaaaac | ggtgtaacaa | gggtgaacac | tatcccatat | caccagctca | 1560 |
| ccgtctttca | ttgccatacg | gaattccgga | tgagcattca | tcaggcgggc | aagaatgtga | 1620 |
| ataaaggccg | gataaaactt | gtgcttattt | ttctttacgg | tctttaaaaa | ggccgtaata | 1680 |
| tccagctgaa | cggtctggtt | ataggtacat | tgagcaactg | actgaaatgc | ctcaaaatgt | 1740 |
| tctttacgat | gccattggga | tatatcaacg | gtggtatatc | cagtgatttt | tttctccatt | 1800 |
| ttagcttcct | tagctcctga | aaatctcgcc | ggatcctaac | tcaaaatcca | cacattatac | 1860 |
| gagccggaag | cataaagtgt | aaagcctggg | gtgcctaatg | cggccgccat | agtgactgga | 1920 |
| tatgttgtgt | tttacagtat | tatgtagtct | gttttttatg | caaaatctaa | tttaatatat | 1980 |
| tgatatttat | atcatttac | gtttctcgtt | cagcttttttt | gtacaaactt | gtgattcttc | 2040 |

```
cttaccaatc atactaatta ttttgggtta aatattaatc attatttttta agatattaat    2100 taagaaatta aaagatttttt taaaaaaatg tataaaatta tattattcat gattttttcat   2160 acatttgatt ttgataataa atatatttttt tttaatttct taaaaaatgt tgcaagacac    2220
ttattagaca tagtcttgtt ctgtttacaa aagcattcat catttaatac attaaaaaat    2280
atttaatact aacagtagaa tcttcttgtg agtggtgtgg gagtaggcaa cctggcattg    2340
aaacgagaga aagagagtca gaaccagaag acaaataaaa agtatgcaac aaacaaatca    2400
aaatcaaagg gcaaaggctg gggttggctc aattggttgc tacattcaat tttcaactca    2460
gtcaacggtt gagattcact ctgacttccc caatctaagc cgcggatgca aacggttgaa    2520
tctaacccac aatccaatct cgttacttag gggcttttcc gtcattaact caccccctgcc   2580 acccggtttc cctataaatt ggaactcaat gctcccctct aaactcgtat cgcttcagag    2640
ttgagaccaa gacacactcg ttcatatatc tctctgctct tctcttctct tctacctctc    2700
aaggtacttt tcttctccct ctaccaaatc ctagattccg tggttcaatt tcggatcttg    2760
cacttctggt ttgctttgcc ttgcttttttc ctcaactggg tccatctagg atccatgtga   2820
aactctactc tttctttaat atctgcggaa tacgcgtttg actttcagat ctagtcgaaa    2880
tcatttcata attgcctttc tttctttttag cttatgagaa ataaaatcac tttttttttta  2940 tttcaaaata aaccttgggc cttgtgctga ctgagatggg gtttggtgat tacagaattt    3000
tagcgaattt tgtaattgta cttgtttgtc tgtagttttg ttttgttttc ttgtttctca    3060
tacattcctt aggcttcaat tttattcgag tataggtcac aataggaatt caaactttga    3120
gcaggggaat taatcccttc cttcaaatcc agtttgtttg tatatatgtt taaaaaatga    3180
aacttttgct ttaaattcta ttataacttt ttttatggct gaaattttttg catgtgtctt   3240 tgctctctgt tgtaaattta ctgtttaggt actaactcta ggcttgttgt gcagtttttg    3300
aagtataacc atgccacaca acacaatggc ggccaccgct tccagaacca cccgattctc    3360
ttcttcctct tcacacccca ccttccccaa acgcattact agatccaccc tccctctctc    3420
tcatcaaacc ctcaccaaac ccaaccacgc tctcaaaatc aaatgttcca tctccaaacc    3480
ccccacggcg cgcgcccttca ccaaggaagc gccgaccacg gagcccttcg tgtcacggtt   3540
cgcctccggc gaacctcgca agggcgcgga catccttgtg gaggcgctgg agaggcaggg    3600
cgtgacgacg gtgttcgcgt accccggcgg tgcgtcgatg gagatccacc aggcgctcac    3660
gcgctccgcc gccatccgca acgtgctccc gcgccacgag cagggcggcg tcttcgccgc    3720
cgaaggctac gcgcgttcct ccggcctccc cggcgtctgc attgccacct ccggccccgg    3780
cgccaccaac ctcgtgagcg gcctcgccga cgctttaatg gacagcgtcc cagtcgtcgc    3840
catcaccggc caggtcgccc gccggatgat cggcaccgac gccttccaag aaaccccgat    3900
cgtggaggtg agcagatcca tcacgaagca caactacctc atcctcgacg tcgacgacat    3960 ccccgcgtc gtcgccgagg cttttcttcgt cgccacctcc ggccgccccg gtccggtcct   4020
catcgacatt cccaaagacg ttcagcagca actcgccgtg cctaattggg acgagcccgt    4080
taacctcccc ggttacctcg ccaggctgcc caggccccccc gccgaggccc aattggaaca   4140
cattgtcaga ctcatcatgg aggcccaaaa gcccgttctc tacgtcggcg gtggcagttt    4200
gaattccagt gctgaattga ggcgctttgt tgaactcact ggtattcccg ttgctagcac    4260
tttaatgggt cttggaactt ttcctattgg tgatgaatat ccccttcaga tgctgggtat    4320
gcatggtact gtttatgcta actatgctgt tgacaatagt gatttgttgc ttgcctttgg    4380
ggtaaggttt gatgaccgtg ttactgggaa gcttgaggct tttgctagta gggctaagat    4440
```

```
tgttcacatt gatattgatt ctgccgagat tgggaagaac aagcaggcgc acgtgtcggt    4500
ttgcgcggat ttgaagttgg ccttgaaggg aattaatatg attttggagg agaaaggagt    4560
ggagggtaag tttgatcttg gaggttggag agaagagatt aatgtgcaga aacacaagtt    4620
tccattgggt tacaagacat tccaggacgc gatttctccg cagcatgcta tcgaggttct    4680
tgatgagttg actaatggag atgctattgt tagtactggg gttgggcagc atcaaatgtg    4740
ggctgcgcag ttttacaagt acaagagacc gaggcagtgg ttgacctcag ggggtcttgg    4800
agccatgggt tttggattgc ctgcggctat tggtgctgct gttgctaacc ctggggctgt    4860
tgtggttgac attgatgggg atggtagttt catcatgaat gttcaggagt tggccactat    4920
aagagtggag aatctcccag ttaagatatt gttgttgaac aatcagcatt tgggtatggt    4980
ggttcagttg gaggataggt tctacaagtc aatagagct cacacctatc ttggagatcc    5040
gtctagcgag agcgagatat tcccaaacat gctcaagttt gctgatgctt gtgggatacc    5100
ggcagcgcga gtgacgaaga aggaagagct tagagcggca attcagagaa tgttggacac    5160
ccctggcccc taccttcttg atgtcattgt gccccatcag gagcatgtgt tgccgatgat    5220
tcccagtaat ggatccttca aggatgtgat aactgagggt gatggtagaa cgaggtactg    5280
attgcctaga ccaaatgttc cttgatgctt gttttgtaca atatatataa gataatgctg    5340
tcctagttgc aggatttggc ctgtggtgag catcatagtc tgtagtagtt ttggtagcaa    5400
gacattttat tttccttta tttaacttac tacatgcagt agcatctatc tatctctgta    5460
gtctgatatc tcctgttgtc tgtattgtgc cgttggattt tttgctgtag tgagactgaa    5520
aatgatgtgc tagtaataat atttctgtta gaaatctaag tagagaatct gttgaagaag    5580
tcaaaagcta atggaatcag gttacatatt caatgttttt cttttttttag cggttggtag    5640 acgtgtagat tcaacttctc ttggagctca cctaggcaat cagtaaaatg catattcctt    5700
ttttaacttg ccatttatt actttagtg gaaattgtga ccaatttgtt catgtagaac    5760
ggatttggac cattgcgtcc acaaaacgtc tcttttgctc gatcttcaca aagcgatacc    5820
gaaatccaga gatagttttc aaagtcaga atggcaaag ttataaatag taaaacagaa    5880
tagatgctgt aatcgacttc aataacaagt ggcatcacgt ttctagttct agacccgggt    5940
accggcgcgc ccgatcatcc ggatatagtt cctcctttca gcaaaaaacc cctcaagacc    6000
cgtttagagg ccccaagggg ttatgctagt tattgctcag cggtggcagc agccaactca    6060
gcttcctttc gggctttgtt agcagccgga tcgatccaag ctgtacctca ctattccttt    6120
gccctcggac gagtgctggg gcgtcggttt ccactatcgg cgagtacttc tacacagcca    6180
tcggtccaga cggccgcgct tctgcgggcg atttgtgtac gcccgacagt cccggctccg    6240
gatcggacga ttgcgtcgca tcgaccctgc gcccaagctg catcatcgaa attgccgtca    6300
accaagctct gatagagttg gtcaagacca atgcggagca tatacgcccg gagccgcggc    6360
gatcctgcaa gctccggatg cctccgctcg aagtagcgcg tctgctgctc catacaagcc    6420
aaccacggcc tccagaagaa gatgttggcg acctcgtatt gggaatcccc gaacatcgcc    6480
tcgctccagt caatgaccgc tgttatgcgg ccattgtccg tcaggacatt gttggagccg    6540
aaatccgcgt gcacgaggtg ccggacttcg ggcagtcct cggcccaaag catcagctca    6600
tcgagagcct gcgcgacgga cgcactgacg tgtcgtcca tcacagtttg ccagtgatac    6660
acatggggat cagcaatcgc gcatatgaaa tcacgccatg tagtgtattg accgattcct    6720
tgcggtccga atgggccgaa cccgctcgtc tggctaagat cggccgcagc gatcgcatcc    6780
```

| | |
|---|---|
| atagcctccg cgaccggctg cagaacagcg ggcagttcgg tttcaggcag gtcttgcaac | 6840 |
| gtgacaccct gtgcacggcg ggagatgcaa taggtcaggc tctcgctgaa ttccccaatg | 6900 |
| tcaagcactt ccggaatcgg gagcgcggcc gatgcaaagt gccgataaac ataacgatct | 6960 |
| ttgtagaaac catcggcgca gctatttacc cgcaggacat atccacgccc tcctacatcg | 7020 |
| aagctgaaag cacgagattc ttcgccctcc gagagctgca tcaggtcgga gacgctgtcg | 7080 |
| aacttttcga tcagaaactt ctcgacagac gtcgcggtga gttcaggctt ttccatgggt | 7140 |
| atatctcctt cttaaagtta aacaaaatta tttctagagg gaaaccgttg tggtctccct | 7200 |
| atagtgagtc gtattaattt cgcgggatcg agatctgatc aacctgcatt aatgaatcgg | 7260 |
| ccaacgcgcg gggagaggcg gtttgcgtat tgggcgctct tccgcttcct cgctcactga | 7320 |
| ctcgctgcgc tcggtcgttc ggctgcggcg agcggtatca gctcactcaa aggcggtaat | 7380 |
| acggttatcc acagaatcag gggataacgc aggaaagaac atgtgagcaa aaggccagca | 7440 |
| aaaggccagg aaccgtaaaa aggccgcgtt gctggcgttt ttccataggc tccgcccccc | 7500 |
| tgacgagcat cacaaaaatc gacgctcaag tcagaggtgg cgaaacccga caggactata | 7560 |
| aagataccag gcgtttcccc ctggaagctc cctcgtgcgc tctcctgttc cgaccctgcc | 7620 |
| gcttaccgga tacctgtccg cctttctccc ttcgggaagc gtggcgcttt ctcaatgctc | 7680 |
| acgctgtagg tatctcagtt cggtgtaggt cgttcgctcc aagctgggct gtgtgcacga | 7740 |
| accccccgtt cagcccgacc gctgcgcctt atccggtaac tatcgtcttg agtccaaccc | 7800 |
| ggtaagacac gacttatcgc cactggcagc agccactggt aacaggatta gcagagcgag | 7860 |
| gtatgtaggc ggtgctacag agttcttgaa gtggtggcct aactacggct acactagaag | 7920 |
| gacagtattt ggtatctgcg ctctgctgaa gccagttacc ttcggaaaaa gagttggtag | 7980 |
| ctcttgatcc ggcaaacaaa ccaccgctgg tagcggtggt ttttttgttt gcaagcagca | 8040 |
| gattacgcgc agaaaaaaag gatctcaaga agatcctttg atcttttcta cggggtctga | 8100 |
| cgctcagtgg aacgaaaact cacgttaagg gattttggtc atgacattaa cctataaaaa | 8160 |
| taggcgtatc acgaggccct ttcgtct | 8187 |

<210> SEQ ID NO 41
<211> LENGTH: 9358
<212> TYPE: DNA
<213> ORGANISM: Artificial
<220> FEATURE:
<223> OTHER INFORMATION: Nucleotide sequence of QC303

<400> SEQUENCE: 41

| | |
|---|---|
| tttgtacaaa cttgtgattc ttccttacca atcatactaa ttattttggg ttaaatatta | 60 |
| atcattattt ttaagatatt aattaagaaa ttaaaagatt ttttaaaaaa atgtataaaa | 120 |
| ttatattatt catgattttt catacatttg attttgataa taaatatatt tttttaatt | 180 |
| tcttaaaaaa tgttgcaaga cacttattag acatagtctt gttctgttta caaaagcatt | 240 |
| catcatttaa tacattaaaa aatatttaat actaacagta gaatcttctt gtgagtggtg | 300 |
| tgggagtagg caacctggca ttgaaacgag agaaagagag tcagaaccag aagacaaata | 360 |
| aaaagtatgc aacaaacaaa tcaaaatcaa agggcaaagg ctgggggttgg ctcaattggt | 420 |
| tgctacattc aattttcaac tcagtcaacg gttgagattc actctgactt ccccaatcta | 480 |
| agccgcggat gcaaacggtt gaatctaacc cacaatccaa tctcgttact taggggcttt | 540 |
| tccgtcatta actcaccccct gccacccggt ttccctataa attggaactc aatgctcccc | 600 |
| tctaaactcg tatcgcttca gagttgagac caagacacac tcgttcatat atctctctgc | 660 |

```
tcttctcttc tcttctacct ctcaaggtac ttttcttctc cctctaccaa atcctagatt      720
ccgtggttca atttcggatc ttgcacttct ggtttgcttt gccttgcttt ttcctcaact      780
gggtccatct aggatccatg tgaaactcta ctctttcttt aatatctgcg gaatacgcgt      840
ttgactttca gatctagtcg aaatcatttc ataattgcct ttctttcttt tagcttatga      900
gaaataaaat cactttttt ttatttcaaa ataaaccttg ggccttgtgc tgactgagat       960
ggggtttggt gattacagaa ttttagcgaa ttttgtaatt gtacttgttt gtctgtagtt     1020
ttgttttgtt ttcttgtttc tcatacattc cttaggcttc aattttattc gagtataggt     1080
cacaatagga attcaaactt tgagcagggg aattaatccc ttccttcaaa tccagtttgt     1140
ttgtatatat gtttaaaaaa tgaaactttt gctttaaatt ctattataac ttttttatg      1200 gctgaaattt ttgcatgtgt ctttgctctc tgttgtaaat ttactgttta ggtactaact     1260
ctaggcttgt tgtgcagttt ttgaagtata accatgccac acaacacaat ggcggccacc     1320
gcttccagaa ccacccgatt ctcttcttcc tcttcacacc ccaccttccc caaacgcatt     1380
actagatcca ccctccctct ctctcatcaa accctcacca aacccaacca cgctctcaaa     1440
atcaaatgtt ccatctccaa acccccacg cggcgccct tcaccaagga agcgccgacc       1500
acggagccct tcgtgtcacg gttcgcctcc ggcgaacctc gcaagggcgc ggacatcctt     1560
gtggaggcgc tggagaggca gggcgtgacg acggtgttcg cgtacccgg cggtgcgtcg      1620 atggagatcc accaggcgct cacgcgctcc gccgccatcc gcaacgtgct cccgcgccac     1680
gagcagggcg gcgtcttcgc cgccgaaggc tacgcgcgtt cctccggcct ccccggcgtc     1740
tgcattgcca cctccggccc cggcgccacc aacctcgtga gcggcctcgc cgacgcttta     1800
atggacagcg tcccagtcgt cgccatcacc ggccaggtcg cccgccggat gatcggcacc     1860
gacgccttcc aagaaacccc gatcgtggag gtgagcagat ccatcacgaa gcacaactac     1920
ctcatcctcg acgtcgacga catccccgc gtcgtcgccg aggctttctt cgtcgccacc      1980
tccggccgcc ccggtccggt cctcatcgac attcccaaag acgttcagca gcaactcgcc     2040
gtgcctaatt gggacgagcc cgttaacctc cccggttacc tcgccaggct gcccaggccc     2100
cccgccgagg cccaattgga acacattgtc agactcatca tggaggccca aaagcccgtt     2160
ctctacgtcg gcggtggcag tttgaattcc agtgctgaat tgaggcgctt tgttgaactc     2220
actggtattc ccgttgctag cactttaatg ggtcttggaa cttttcctat tggtgatgaa     2280
tattcccttc agatgctggg tatgcatggt actgtttatg ctaactatgc tgttgacaat     2340
agtgatttgt tgcttgcctt tggggtaagg tttgatgacc gtgttactgg gaagcttgag     2400
gcttttgcta gtagggctaa gattgttcac attgatattg attctgccga gattgggaag     2460
aacaagcagg cgcacgtgtc ggtttgcgcg gatttgaagt tggccttgaa gggaattaat     2520
atgattttgg aggagaaagg agtggagggt aagtttgatc ttggaggttg gagagaagag     2580
attaatgtgc agaaacacaa gtttccattg ggttacaaga cattccagga cgcgatttct     2640
ccgcagcatg ctatcgaggt tcttgatgag ttgactaatg gagatgctat tgttagtact     2700
ggggttgggc agcatcaaat gtgggctgcg cagttttaca agtacaagag accgaggcag     2760
tggttgacct caggggtct tggagccatg ggttttggat tgcctgcggc tattggtgct     2820
gctgttgcta accctggggc tgttgtggtt gacattgatg gggatggtag tttcatcatg     2880
aatgttcagg agttggccac tataagagtg gagaatctcc cagttaagat attgttgttg     2940
aacaatcagc atttgggtat ggtggttcag ttggaggata ggttctacaa gtccaataga     3000
```

```
gctcacacct atcttggaga tccgtctagc gagagcgaga tattcccaaa catgctcaag    3060
tttgctgatg cttgtgggat accggcagcg cgagtgacga agaaggaaga cttagagcg     3120
gcaattcaga gaatgttgga caccctggc ccctaccttc ttgatgtcat tgtgccccat     3180
caggagcatg tgttgccgat gattcccagt aatggatcct tcaaggatgt gataactgag    3240
ggtgatggta gaacgaggta ctgattgcct agaccaaatg ttccttgatg cttgttttgt    3300
acaatatata taagataatg ctgtcctagt tgcaggattt ggcctgtggt gagcatcata    3360
gtctgtagta gttttggtag caagacattt tatttccctt ttatttaact tactacatgc    3420
agtagcatct atctatctct gtagtctgat atctcctgtt gtctgtattg tgccgttgga    3480
tttttgctg tagtgagact gaaaatgatg tgctagtaat aatatttctg ttagaaatct     3540
aagtagagaa tctgttgaag aagtcaaaag ctaatggaat caggttacat attcaatgtt    3600
tttctttttt tagcggttgg tagacgtgta gattcaactt ctcttggagc tcacctaggc    3660
aatcagtaaa atgcatattc ctttttaac ttgccattta tttacttta gtggaaattg      3720
tgaccaattt gttcatgtag aacggatttg gaccattgcg tccacaaaac gtctcttttg    3780
ctcgatcttc acaaagcgat accgaaatcc agagatagtt ttcaaaagtc agaaatggca    3840
aagttataaa tagtaaaaca gaatagatgc tgtaatcgac ttcaataaca agtggcatca    3900
cgtttctagt tctagacccg ggtaccggcg cgcccgatca tccggatata gttcctcctt    3960
tcagcaaaaa accctcaag acccgtttag aggcccaag gggttatgct agttattgct      4020
cagcggtggc agcagccaac tcagcttcct ttcgggcttt gttagcagcc ggatcgatcc    4080
aagctgtacc tcactattcc tttgccctcg gacgagtgct ggggcgtcgg tttccactat    4140
cggcgagtac ttctacacag ccatcggtcc agacggccgc gcttctgcgg gcgatttgtg    4200
tacgcccgac agtcccggct ccggatcgga cgattgcgtc gcatcgaccc tgcgcccaag    4260
ctgcatcatc gaaattgccg tcaaccaagc tctgatagag ttggtcaaga ccaatgcgga    4320
gcatatacgc ccggagccgc ggcgatcctg caagctccgg atgcctccgc tcgaagtagc    4380
gcgtctgctg ctccatacaa gccaaccacg gcctccagaa gaagatgttg gcgacctcgt    4440
attgggaatc cccgaacatc gcctcgctcc agtcaatgac cgctgttatg cggccattgt    4500
ccgtcaggac attgttggag ccgaaatccg cgtgcacgag gtgccggact cggggcagt    4560
cctcggccca agcatcagc tcatcgagag cctgcgcgac ggacgcactg acggtgtcgt     4620
ccatcacagt ttgccagtga tacacatggg gatcagcaat cgcgcatatg aaatcacgcc    4680
atgtagtgta ttgaccgatt ccttgcggtc cgaatgggcc gaacccgctc gtctggctaa    4740
gatcggccgc agcgatcgca tccatagcct ccgcgaccgg ctgcagaaca gcgggcagtt    4800
cggtttcagg caggtcttgc aacgtgacac cctgtgcacg gcgggagatg caataggtca    4860
ggctctcgct gaattcccca atgtcaagca cttccggaat cgggagcgcg ccgatgcaa     4920
agtgccgata aacataacga tctttgtaga aaccatcggc gcagctattt acccgcagga    4980
catatccacg ccctcctaca tcgaagctga agcacgaga ttcttcgccc tccgagagct     5040
gcatcaggtc ggagacgctg tcgaactttt cgatcagaaa cttctcgaca gacgtcgcgg    5100
tgagttcagg cttttccatg gtatatctc cttcttaaag ttaaacaaaa ttatttctag     5160
agggaaaccg ttgtggtctc cctatagtga gtcgtattaa tttcgcggga tcgagatctg    5220
atcaacctgc attaatgaat cggccaacgc gcggggagag gcggtttgcg tattgggcgc    5280
tcttccgctt cctcgctcac tgactcgctg cgctcggtcg ttcggctgcg gcgagcggta    5340
tcagctcact caaaggcggt aatacggtta tccacagaat caggggataa cgcaggaaag    5400
```

```
aacatgtgag caaaaggcca gcaaaaggcc aggaaccgta aaaaggccgc gttgctggcg    5460 ttttttccata ggctccgccc ccctgacgag catcacaaaa atcgacgctc aagtcagagg    5520
tggcgaaacc cgacaggact ataaagatac caggcgtttc ccctggaag ctccctcgtg    5580 cgctctcctg ttccgaccct gccgcttacc ggatacctgt ccgcctttct cccttcggga    5640
agcgtggcgc tttctcaatg ctcacgctgt aggtatctca gttcggtgta ggtcgttcgc    5700
tccaagctgg gctgtgtgca cgaacccccc gttcagcccg accgctgcgc cttatccggt    5760
aactatcgtc ttgagtccaa cccggtaaga cacgacttat cgccactggc agcagccact    5820
ggtaacagga ttagcagagc gaggtatgta ggcggtgcta cagagttctt gaagtggtgg    5880
cctaactacg gctacactag aaggacagta tttggtatct gcgctctgct gaagccagtt    5940
accttcggaa aaagagttgg tagctcttga tccggcaaac aaaccaccgc tggtagcggt    6000
ggtttttttg tttgcaagca gcagattacg cgcagaaaaa aaggatctca agaagatcct    6060
ttgatctttt ctacggggtc tgacgctcag tggaacgaaa actcacgtta agggattttg    6120
gtcatgacat taacctataa aaataggcgt atcacgaggc cctttcgtct cgcgcgtttc    6180
ggtgatgacg gtgaaaacct ctgacacatg cagctcccgg agacggtcac agcttgtctg    6240
taagcggatg ccgggagcag acaagcccgt cagggcgcgt cagcgggtgt tggcgggtgt    6300
cggggctggc ttaactatgc ggcatcagag cagattgtac tgagagtgca ccatatggac    6360
atattgtcgt tagaacgcgg ctacaattaa tacataacct tatgtatcat acacatacga    6420
tttaggtgac actatagaac ggcgcgccgg taccgggccc cccctcgagt gcggccgcaa    6480
gcttgtcgac ggagatcacc actttgtaca agaaagctgg gtctagatat ctcgagtgcg    6540
gccgccagtg tgatggatat cagctgggcc ggccactaga attcccgatc tagtaacata    6600
gatgacaccg cgcgcgataa tttatcctag tttgcgcgct atattttgtt ttctatcgcg    6660
tattaaatgt ataattgcgg gactctaatc ataaaaaccc atctcataaa taacgtcatg    6720
cattacatgt taattattac atgcttaacg taattcaaca gaaattatat gataatcatc    6780
gcaagaccgg caacaggatt caatcttaag aaactttatt gccaaatgtt tgaacgatcg    6840
gggaaattcg agctctcagg ccagggcgct ggggaaggcg atggcgtgct cggtcagctg    6900
ccacttctgg ttcttggcgt cgctccggtc ctcccgcagc agcttgtgct ggatgaagtg    6960
ccactcgggc atcttgctgg gcacgctctt ggccttgtac acggtgtcga actggcaccg    7020
gtaccggccg ccgtccttca gcagcaggta catgctcacg tcgcccttca ggatgccctg    7080
cttaggcacg gcatgatct tctcgcagct ggcctcccag ttggtggtca tcttcttcat    7140
cacggggccg tcggcgggga agttcacgcc gttgaagatg ctcttgtggt agatgcagtt    7200
ctccttcacg ctcacggtga tgtccacgtt acagatgcac acggcgccgt cctcgaacag    7260
gaagctccgg ccccaggtgt agccggcggg gcagctgttc ttgaagtagt ccacgatgtc    7320 ctggggtac tcggtgaaga tccggtcgcc gtacttgaag ccggcgctca ggatgtcctc    7380
gctgaagggc aggggccgc cctcgatcac gcacaggttg atggtctgct tgcccttgaa    7440
ggggtagccg atgccctcgc cggtgatcac gaacttgtgg ccgttcacgc agccctccat    7500
gtggtacttc atggtcatct cctccttcag gccgtgcttg ctgtgggcca tggatttgga    7560
agagtgttag aggacgaaat tgcacttctt caatggttag ttatagtgag tgagaatgtt    7620
atgatttgag aatttaagga ctaaatatag agtacagatt caacctgagt ttgttaggtg    7680
aaaggtgaag gaatggtagg taattttact gattgatttc atttaacata tgcaagcaat    7740
```

-continued

| | |
|---|---|
| tgaatgaccg cggggtagct gaaacctaca atatgataca attaatgaat atatatctat | 7800 |
| aggtttagac aaatatgtat atcagagttc ataatggttg gctaacttga tcatccgttt | 7860 |
| ctatatattt atagccatgt ggcttggcag gttctgctt cccccaaaat gattttggag | 7920 |
| ccctaagaga tgctgccact ttcctaagaa ttaaaagttt tcatatggct gcacttaaat | 7980 |
| ttgtactaac ttgtttataa tttccgactt caactctgcc gaaatcatta attaaagtca | 8040 |
| ccataagtat tgttggtttc gatatttgat gatgcgtagt cattttattt ttatattctt | 8100 |
| ctcttttgt ctaattaact cctttcttta ttagatcatt tagtgatatg atactttcta | 8160 |
| agacattata aatgttaatt tgttgtaaa tgttaatggg aggtttggaa tccatgagtt | 8220 |
| ctctcttcac cttttttcct tcatcgtttt tcaattgttt tatcaactac ttatatctct | 8280 |
| atctttgtat attactctgt gtaacatttt attactctgt tttcgttata ttcgtatgaa | 8340 |
| gccaacgata aactaattct tcaccagaaa ttaaactcgt gcttgtttct cttctcagtt | 8400 |
| ttttctttac catttgtaa ctttctaatt tattatgttt tgataattat tttcaaacca | 8460 |
| agtaaaaact gaaaaataaa aacagataaa acatatatgt ctttaatttc atattcacgt | 8520 |
| aaatataaag ctagagatat ttttttaaaa aatatgaata atgatagtat tataataagt | 8580 |
| aatgttatat tttcttataa atcttcttga tgttttataa taaaaaaaaa ttaaatagaa | 8640 |
| tacattttat gtcttaaaaa cttttaaaac atccaatatt ttctatatct aacaagtgat | 8700 |
| gatataatta gtaagaagat tctatgacaa aaaaaaata gaattaatta ttctactgtg | 8760 |
| atgatatatt cgtaactgtc ttttcctaaa tgtaacaact gaagtatgca accatcaaca | 8820 |
| tttatgggtt aggtagaaca gaccatgtta tattcaatgc ttctcaataa tagtaattta | 8880 |
| ggtactttga gttatcaatc tttgtcagtt gccctgcaaa gtgccttatg gtgggataca | 8940 |
| tcatataagg gtgaaaaaga tagttttccta tggtgggata catcatatgc tctcccacct | 9000 |
| tagccttcgc ctacatgtgt gtgtaaaaag tttatatctc atgagtcaag agatttgatg | 9060 |
| tatgaaatta caatttgaat caaaagttat ataatataat actcagttaa gttttcctcc | 9120 |
| ggatgcaggt ttatttatat tattattgta ttgtaatttt ttgcctataa aagacctaat | 9180 |
| taataagcaa taagtagtgg gagatttgtc aaacaagatt gtaaaattga cttaattttg | 9240 |
| acgaagtgtt ttatccctc ttataaattt tgataaacat acaatatttt tagaattaaa | 9300 |
| attttgggag accatggatc ccgggtcgac tgaattggtt ccggcgccag cctgcttt | 9358 |

<210> SEQ ID NO 42
<211> LENGTH: 2817
<212> TYPE: DNA
<213> ORGANISM: Artificial
<220> FEATURE:
<223> OTHER INFORMATION: Nucleotide sequence of pCR8/GW/TOPO

<400> SEQUENCE: 42

| | |
|---|---|
| ctttcctgcg ttatccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |
| acaacgttca aatccgctcc cggcggattt gtcctactca ggagagcgtt caccgacaaa | 420 |
| caacagataa aacgaaaggc ccagtcttcc gactgagcct ttcgttttat ttgatgcctg | 480 |

```
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg cttttttata atgccaactt tgtacaaaaa    660
agcaggctcc gaattcgccc ttaagggcga attcgaccca gctttcttgt acaaagttgg    720
cattataaaa aataattgct catcaatttg ttgcaacgaa caggtcacta tcagtcaaaa    780
taaaatcatt atttgccatc cagctgatat cccctatagt gagtcgtatt acatggtcat    840
agctgtttcc tggcagctct ggcccgtgtc tcaaaatctc tgatgttaca ttgcacaaga    900
taaaaatata tcatcatgcc tcctctagac cagccaggac agaaatgcct cgacttcgct    960
gctgcccaag gttgccgggt gacgcacacc gtggaaacgg atgaaggcac gaacccagtg   1020
gacataagcc tgttcggttc gtaagctgta atgcaagtag cgtatgcgct cacgcaactg   1080
gtccagaacc ttgaccgaac gcagcggtgg taacggcgca gtggcggttt tcatggcttg   1140
ttatgactgt ttttttgggg tacagtctat gcctcgggca tccaagcagc aagcgcgtta   1200
cgccgtgggt cgatgtttga tgttatggag cagcaacgat gttacgcagc agggcagtcg   1260
ccctaaaaca aagttaaaca tcatgaggga agcggtgatc gccgaagtat cgactcaact   1320
atcagaggta gttggcgtca tcgagcgcca tctcgaaccg acgttgctgg ccgtacattt   1380
gtacggctcc gcagtggatg gcggcctgaa gccacacagt gatattgatt tgctggttac   1440
ggtgaccgta aggcttgatg aaacaacgcg gcgagctttg atcaacgacc ttttggaaac   1500
ttcggcttcc cctggagaga gcgagattct ccgcgctgta gaagtcacca ttgttgtgca   1560
cgacgacatc attccgtggc gttatccagc taagcgcgaa ctgcaatttg gagaatggca   1620
gcgcaatgac attcttgcag gtatcttcga gccagccacg atcgacattg atctggctat   1680
cttgctgaca aaagcaagag aacatagcgt tgccttggta ggtccagcgg cggaggaact   1740
ctttgatccg gttcctgaac aggatctatt tgaggcgcta aatgaaacct taacgctatg   1800
gaactcgccg cccgactggg ctggcgatga gcgaaatgta gtgcttacgt tgtcccgcat   1860
ttggtacagc gcagtaaccg gcaaaatcgc gccgaaggat gtcgctgccg actgggcaat   1920
ggagcgcctg ccggcccagt atcagcccgt catacttgaa gctagacagg cttatcttgg   1980
acaagaagaa gatcgcttgg cctcgcgcgc agatcagttg gaagaatttg tccactacgt   2040
gaaaggcgag atcaccaagg tagtcggcaa ataaccctcg agccacccat gaccaaaatc   2100
ccttaacgtg agttacgcgt cgttccactg agcgtcagac cccgtagaaa agatcaaagg   2160
atcttcttga tccttttttt tctgcgcgt aatctgctgc ttgcaaacaa aaaaaccacc   2220
gctaccagcg gtggtttgtt tgccggatca agagctacca actcttttc cgaaggtaac   2280 tggcttcagc agagcgcaga taccaaatac tgtccttcta gtgtagccgt agttaggcca   2340
ccacttcaag aactctgtag caccgcctac atacctcgct ctgctaatcc tgttaccagt   2400
ggctgctgcc agtggcgata gtcgtgtct taccggggttg gactcaagac gatagttacc   2460
ggataaggcg cagcggtcgg gctgaacggg gggttcgtgc acacagccca gcttggagcg   2520
aacgacctac accgaactga gatacctaca gcgtgagcat tgagaaagcg ccacgcttcc   2580
cgaagggaga aaggcggaca ggtatccggt aagcggcagg gtcggaacag gagagcgcac   2640
gagggagctt ccagggggaa acgcctggta tctttatagt cctgtcgggt ttcgccacct   2700
ctgacttgag cgtcgatttt tgtgatgctc gtcagggggg cggagcctat ggaaaaacgc   2760
cagcaacgcg gccttttac ggttcctggc cttttgctgg ccttttgctc acatgtt      2817
```

<210> SEQ ID NO 43
<211> LENGTH: 4201
<212> TYPE: DNA
<213> ORGANISM: Artificial
<220> FEATURE:
<223> OTHER INFORMATION: Nucleotide sequence of QC301-1

<400> SEQUENCE: 43

| | | | | | |
|---|---|---|---|---|---|
| cccaccataa | ggcactttgc | agggcaactg | acaaagattg | ataactcaaa | gtacctaaat | 60 |
| tactattatt | gagaagcatt | gaatataaca | tggtctgttc | tacctaaccc | ataaatgttg | 120 |
| atggttgcat | acttcagttg | ttacatttag | gaaaagacag | ttacgaatat | atcatcacag | 180 |
| tagaataatt | aattctattt | ttttttttgtc | atagaatctt | cttactaatt | atatcatcac | 240 |
| ttgttagata | tagaaaatat | tggatgtttt | aaaagttttt | aagacataaa | atgtattcta | 300 |
| tttaattttt | ttttattata | aaacatcaag | aagatttata | agaaaatata | acattactta | 360 |
| ttataatact | atcattattc | atattttta | aaaaaatatc | tctagcttta | tatttacgtg | 420 |
| aatatgaaat | taaagacata | tatgttttat | ctgtttttat | ttttcagttt | ttacttggtt | 480 |
| tgaaataat | tatcaaaaca | taataaatta | gaaagttaca | aaatggtaaa | gaaaaaactg | 540 |
| agaagagaaa | caagcacgag | tttaatttct | ggtgaagaat | tagtttatcg | ttggcttcat | 600 |
| acgaatataa | cgaaaacaga | gtaataaaat | gttacacaga | gtaatataca | aagatagaga | 660 |
| tataagtagt | tgataaaaca | attgaaaaac | gatgaaggaa | aaaaggtgaa | gagagaactc | 720 |
| atggattcca | aacctcccat | taacatttac | aacaaaatta | acatttataa | tgtcttagaa | 780 |
| agtatcatat | cactaaatga | tctaataaag | aaaggagtta | attagacaaa | aagagaagaa | 840 |
| tataaaaata | aaatgactac | gcatcatcaa | atatcgaaac | caacaatact | tatggtgact | 900 |
| ttaattaatg | atttcggcag | agttgaagtc | ggaaattata | acaagttag | tacaaattta | 960 |
| agtgcagcca | tatgaaaact | tttaattctt | aggaaagtgg | cagcatctct | tagggctcca | 1020 |
| aaatcatttt | gggggaagca | gaaacctgcc | aagccacatg | gctataaata | tatagaaacg | 1080 |
| gatgatcaag | ttagccaacc | attatgaact | ctgatataca | tatttgtcta | aacctataga | 1140 |
| tatatattca | ttaattgtat | catattgtag | gtttcagcta | ccccgcggtc | attcaattgc | 1200 |
| ttgcatatgt | taaatgaaat | caatcagtaa | aattacctac | cattccttca | cctttcacct | 1260 |
| aacaaactca | ggttgaatct | gtactctata | tttagtcctt | aaattctcaa | atcataacat | 1320 |
| tctcactcac | tataactaac | cattgaagaa | gtgcaatttc | gtcctctaac | actcttccaa | 1380 |
| atccaagggc | gaattcgacc | cagctttctt | gtacaaagtt | ggcattataa | aaaataattg | 1440 |
| ctcatcaatt | tgttgcaacg | aacaggtcac | tatcagtcaa | aataaaatca | ttatttgcca | 1500 |
| tccagctgat | atccctata | gtgagtcgta | ttacatggtc | atagctgttt | cctggcagct | 1560 |
| ctggcccgtg | tctcaaaatc | tctgatgtta | cattgcacaa | gataaaaata | tatcatcatg | 1620 |
| cctcctctag | accagccagg | acagaaatgc | ctcgacttcg | ctgctgccca | aggttgccgg | 1680 |
| gtgacgcaca | ccgtggaaac | ggatgaaggc | acgaacccag | tggacataag | cctgttcggt | 1740 |
| tcgtaagctg | taatgcaagt | agcgtatgcg | ctcacgcaac | tggtccagaa | ccttgaccga | 1800 |
| acgcagcggt | ggtaacggcg | cagtggcggt | tttcatggct | tgttatgact | gtttttttgg | 1860 |
| ggtacagtct | atgcctcggg | catccaagca | gcaagcgcgt | tacgccgtgg | gtcgatgttt | 1920 |
| gatgttatgg | agcagcaacg | atgttacgca | gcagggcagt | cgccctaaaa | caaagttaaa | 1980 |
| catcatgagg | gaagcggtga | tcgccgaagt | atcgactcaa | ctatcagagg | tagttggcgt | 2040 |
| catcgagcgc | catctcgaac | cgacgttgct | ggccgtacat | ttgtacggct | ccgcagtgga | 2100 |

```
tggcggcctg aagccacaca gtgatattga tttgctggtt acggtgaccg taaggcttga    2160
tgaaacaacg cggcgagctt tgatcaacga ccttttggaa acttcggctt ccctggaga    2220 gagcgagatt ctccgcgctg tagaagtcac cattgttgtg cacgacgaca tcattccgtg    2280
gcgttatcca gctaagcgcg aactgcaatt tggagaatgg cagcgcaatg acattcttgc    2340
aggtatcttc gagccagcca cgatcgacat tgatctggct atcttgctga caaaagcaag    2400
agaacatagc gttgccttgg taggtccagc ggcggaggaa ctctttgatc cggttcctga    2460
acaggatcta tttgaggcgc taaatgaaac cttaacgcta tggaactcgc cgcccgactg    2520
ggctggcgat gagcgaaatg tagtgcttac gttgtcccgc atttggtaca gcgcagtaac    2580
cggcaaaatc gcgccgaagg atgtcgctgc cgactgggca atggagcgcc tgccggccca    2640
gtatcagccc gtcatacttg aagctagaca ggcttatctt ggacaagaag aagatcgctt    2700
ggcctcgcgc gcagatcagt tggaagaatt tgtccactac gtgaaaggcg agatcaccaa    2760
ggtagtcggc aaataaccct cgagccaccc atgaccaaaa tcccttaacg tgagttacgc    2820
gtcgttccac tgagcgtcag accccgtaga aaagatcaaa ggatcttctt gagatccttt    2880
ttttctgcgc gtaatctgct gcttgcaaac aaaaaaacca ccgctaccag cggtggtttg    2940
tttgccggat caagagctac caactctttt tccgaaggta actggcttca gcagagcgca    3000
gataccaaat actgtccttc tagtgtagcc gtagttaggc caccacttca agaactctgt    3060
agcaccgcct acatacctcg ctctgctaat cctgttacca gtggctgctg ccagtggcga    3120
taagtcgtgt cttaccgggt tggactcaag acgatagtta ccggataagg cgcagcggtc    3180
gggctgaacg gggggttcgt gcacacagcc cagcttggag cgaacgacct acaccgaact    3240
gagataccta cagcgtgagc attgagaaag cgccacgctt cccgaaggga aaaggcgga    3300 caggtatccg gtaagcggca gggtcggaac aggagagcgc acgagggagc ttccaggggg    3360
aaacgcctgg tatctttata gtcctgtcgg gtttcgccac ctctgacttg agcgtcgatt    3420
tttgtgatgc tcgtcagggg ggcggagcct atggaaaaac gccagcaacg cggccttttt    3480
acggttcctg gccttttgct ggccttttgc tcacatgttc tttcctgcgt tatcccctga    3540
ttctgtggat aaccgtatta ccgcctttga gtgagctgat accgctcgcc gcagccgaac    3600
gaccgagcgc agcgagtcag tgagcgagga agcggaagag cgcccaatac gcaaaccgcc    3660
tctccccgcg cgttggccga ttcattaatg cagctggcac gacaggtttc ccgactggaa    3720
agcgggcagt gagcgcaacg caattaatac gcgtaccgct agccaggaag agtttgtaga    3780
aacgcaaaaa ggccatccgt caggatggcc ttctgcttag tttgatgcct ggcagtttat    3840
ggcgggcgtc ctgcccgcca ccctccgggc cgttgcttca caacgttcaa atccgctccc    3900
ggcggatttg tcctactcag gagagcgttc accgacaaac aacagataaa acgaaaggcc    3960
cagtcttccg actgagcctt tcgttttatt tgatgcctgg cagttcccta ctctcgcgtt    4020
aacgctagca tggatgtttt cccagtcacg acgttgtaaa acgacggcca gtcttaagct    4080
cgggccccaa ataatgattt tattttgact gatagtgacc tgttcgttgc aacaaattga    4140
tgagcaatgc ttttttataa tgccaacttt gtacaaaaaa gcaggctccg aattcgccct    4200
t                                                                     4201

<210> SEQ ID NO 44
<211> LENGTH: 5286
<212> TYPE: DNA
<213> ORGANISM: Artificial
<220> FEATURE:
```

<223> OTHER INFORMATION: Nucleotide sequence of QC330

<400> SEQUENCE: 44

```
atcaacaagt tgtacaaaa aagctgaacg agaaacgtaa aatgatataa atatcaatat    60
attaaattag atttgcata aaaaacagac tacataatac tgtaaaacac aacatatcca   120
gtcatattgg cggccgcatt aggcacccca ggctttacac tttatgcttc cggctcgtat   180
aatgtgtgga ttttgagtta ggatccgtcg agattttcag gagctaagga agctaaaatg   240
gagaaaaaaa tcactggata taccaccgtt gatatatccc aatggcatcg taaagaacat   300
tttgaggcat ttcagtcagt tgctcaatgt acctataacc agaccgttca gctggatatt   360
acggcctttt taaagaccgt aaagaaaaat aagcacaagt tttatccggc ctttattcac   420
attcttgccc gcctgatgaa tgctcatccg gaattccgta tggcaatgaa agacggtgag   480
ctggtgatat gggatagtgt tcacccttgt tacaccgttt tccatgagca aactgaaacg   540
ttttcatcgc tctggagtga ataccacgac gatttccggc agtttctaca catatattcg   600
caagatgtgg cgtgttacgg tgaaaacctg gcctatttcc ctaaagggtt tattgagaat   660
atgttttcg tctcagccaa tccctgggtg agtttcacca gttttgattt aaacgtggcc   720
aatatggaca acttcttcgc ccccgttttc accatgggca aatattatac gcaaggcgac   780
aaggtgctga tgccgctggc gattcaggtt catcatgccg tttgtgatgg cttccatgtc   840
ggcagaatgc ttaatgaatt acaacagtac tgcgatgagt ggcagggcgg ggcgtaaaga   900
tctggatccg gcttactaaa agccagataa cagtatgcgt atttgcgcgc tgattttgc    960
ggtataagaa tatatactga tatgtatacc cgaagtatgt caaaaagagg tatgctatga  1020
agcagcgtat tacagtgaca gttgacagcg acagctatca gttgctcaag gcatatatga  1080
tgtcaatatc tccggtctgg taagcacaac catgcagaat gaagcccgtc gtctgcgtgc  1140
cgaacgctgg aaagcggaaa tcaggaagg gatggctgag gtcgcccggt ttattgaaat  1200
gaacggctct tttgctgacg agaacagggg ctggtgaaat gcagtttaag gtttacacct  1260
ataaaagaga gagccgttat cgtctgtttg tggatgtaca gagtgatatt attgacacgc  1320
ccgggcgacg gatggtgatc ccctggcca gtgcacgtct gctgtcagat aaagtctccc  1380
gtgaacttta cccggtggtg catatcgggg atgaaagctg gcgcatgatg accaccgata  1440
tggccagtgt gccggtctcc gttatcgggg aagaagtggc tgatctcagc caccgcgaaa  1500
atgacatcaa aaacgccatt aacctgatgt tctggggaat aaaatgtca ggctcccta   1560
tacacagcca gtctgcaggt cgaccatagt gactggatat gttgtgtttt acagtattat  1620
gtagtctgtt ttttatgcaa aatctaattt aatatattga tatttatatc attttacgtt  1680
tctcgttcag cttcttgta caaagtggtt gatgggatcc atggcccaca gcaagcacgg  1740
cctgaaggag gagatgacca tgaagtacca catggagggc tgcgtgaacg gccacaagtt  1800
cgtgatcacc ggcgagggca tcggctaccc cttcaagggc aagcagacca tcaacctgtg  1860
cgtgatcgag ggcggccccc tgcccttcag cgaggacatc ctgagcgccg gcttcaagta  1920
cggcgaccgg atcttcaccg agtaccccca ggacatcgtg gactacttca gaacagctg   1980
ccccgccggc tacacctggg gccggagctt cctgttcgag gacggcgccg tgtgcatctg  2040
taacgtggac atcaccgtga gcgtgaagga gaactgcatc taccacaaga gcatcttcaa  2100
cggcgtgaac ttccccgccg acggcccccgt gatgaagaag atgaccacca actgggaggc  2160
cagctgcgag aagatcatgc ccgtgcctaa gcagggcatc ctgaagggcg acgtgagcat  2220
gtacctgctg ctgaaggacg gcggccggta ccggtgccag ttcgacaccg tgtacaaggc  2280
```

```
caagagcgtg cccagcaaga tgcccgagtg gcacttcatc cagcacaagc tgctgcggga    2340
ggaccggagc gacgccaaga accagaagtg gcagctgacc gagcacgcca tcgccttccc    2400
cagcgccctg gcctgagagc tcgaatttcc ccgatcgttc aaacatttgg caataaagtt    2460
tcttaagatt gaatcctgtt gccggtcttg cgatgattat catataattt ctgttgaatt    2520
acgttaagca tgtaataatt aacatgtaat gcatgacgtt atttatgaga tgggttttta    2580
tgattagagt cccgcaatta tacatttaat acgcgataga aaacaaaata tagcgcgcaa    2640
actaggataa attatcgcgc gcggtgtcat ctatgttact agatcgggaa ttctagtggc    2700
cggcccagct gatatccatc acactggcgg ccgctcgagt tctatagtgt cacctaaatc    2760
gtatgtgtat gatacataag gttatgtatt aattgtagcc gcgttctaac gacaatatgt    2820
ccatatggtg cactctcagt acaatctgct ctgatgccgc atagttaagc cagccccgac    2880
acccgccaac acccgctgac gcgccctgac gggcttgtct gctcccggca tccgcttaca    2940
gacaagctgt gaccgtctcc gggagctgca tgtgtcagag gttttcaccg tcatcaccga    3000
aacgcgcgag acgaaagggc ctcgtgatac gcctattttt ataggttaat gtcatgacca    3060
aaatccctta acgtgagttt tcgttccact gagcgtcaga ccccgtagaa aagatcaaag    3120
gatcttcttg agatcctttt tttctgcgcg taatctgctg cttgcaaaca aaaaaaccac    3180
cgctaccagc ggtggtttgt ttgccggatc aagagctacc aactcttttt ccgaaggtaa    3240
ctggcttcag cagagcgcag ataccaaata ctgtccttct agtgtagccg tagttaggcc    3300
accacttcaa gaactctgta gcaccgccta catacctcgc tctgctaatc ctgttaccag    3360
tggctgctgc cagtggcgat aagtcgtgtc ttaccgggtt ggactcaaga cgatagttac    3420
cggataaggc gcagcggtcg ggctgaacgg ggggttcgtg cacacagccc agcttggagc    3480
gaacgaccta caccgaactg agatacctac agcgtgagca ttgagaaagc gccacgcttc    3540
ccgaagggag aaaggcggac aggtatccgg taagcggcag ggtcggaaca ggagagcgca    3600
cgagggagct tccaggggga aacgcctggt atctttatag tcctgtcggg tttcgccacc    3660
tctgacttga gcgtcgattt ttgtgatgct cgtcaggggg gcggagccta tggaaaaacg    3720
ccagcaacgc ggcctttta cggttcctgg ccttttgctg gccttttgct cacatgttct    3780
ttcctgcgtt atcccctgat tctgtggata accgtattac cgcctttgag tgagctgata    3840
ccgctcgccg cagccgaacg accgagcgca gcgagtcagt gagcgaggaa gcggaagagc    3900
gcccaatacg caaaccgcct ctccccgcgc gttggccgat tcattaatgc aggttgatca    3960
gatctcgatc ccgcgaaatt aatacgactc actataggga gaccacaacg gtttccctct    4020
agaaataatt ttgtttaact ttaagaagga gatataccca tggaaaagcc tgaactcacc    4080
gcgacgtctg tcgagaagtt tctgatcgaa aagttcgaca cgtctccgga cctgatgcag    4140
ctctcggagg gcgaagaatc tcgtgctttc agcttcgatg taggagggcg tggatatgtc    4200
ctgcgggtaa atagctgcgc cgatggtttc tacaaagatc gttatgttta tcggcacttt    4260
gcatcggccg cgctcccgat tccggaagtg cttgacattg gggaattcag cgagagcctg    4320
acctattgca tctcccgccg tgcacagggt gtcacgttgc aagacctgcc tgaaaccgaa    4380
ctgcccgctg ttctgcagcc ggtcgcggag gctatggatg cgatcgctgc ggccgatctt    4440
agccagacga gcgggttcgg cccattcgga ccgcaaggaa tcggtcaata cactacatgg    4500
cgtgatttca tatgcgcgat tgctgatccc catgtgtatc actggcaaac tgtgatggac    4560
gacaccgtca gtgcgtccgt cgcgcaggct ctcgatgagc tgatgctttg ggccgaggac    4620
```

```
tgccccgaag tccggcacct cgtgcacgcg gatttcggct ccaacaatgt cctgacggac      4680
aatggccgca taacagcggt cattgactgg agcgaggcga tgttcgggga ttcccaatac      4740
gaggtcgcca acatcttctt ctggaggccg tggttggctt gtatggagca gcagacgcgc      4800
tacttcgagc ggaggcatcc ggagcttgca ggatcgccgc ggctccgggc gtatatgctc      4860
cgcattggtc ttgaccaact ctatcagagc ttggttgacg gcaatttcga tgatgcagct      4920
tgggcgcagg tcgatgcga cgcaatcgtc cgatccggag ccgggactgt cgggcgtaca      4980
caaatcgccc gcagaagcgc ggccgtctgg accgatggct gtgtagaagt actcgccgat      5040
agtggaaacc gacgcccag cactcgtccg agggcaaagg aatagtgagg tacagcttgg       5100
atcgatccgg ctgctaacaa agcccgaaag gaagctgagt tggctgctgc caccgctgag      5160
caataactag cataacccct tggggcctct aaacgggtct tgaggggttt tttgctgaaa      5220
ggaggaacta tatccggatg atcgtcgagg cctcacgtgt taacaagctt gcatgcctgc      5280
aggttt                                                                 5286
```

<210> SEQ ID NO 45
<211> LENGTH: 5042
<212> TYPE: DNA
<213> ORGANISM: Artificial
<220> FEATURE:
<223> OTHER INFORMATION: Nucleotide sequence of QC301-1Y

<400> SEQUENCE: 45

```
cttgtacaaa gtggttgatg ggatccatgg cccacagcaa gcacggcctg aaggaggaga       60
tgaccatgaa gtaccacatg gagggctgcg tgaacggcca caagttcgtg atcaccggcg      120
agggcatcgg ctaccccttc aagggcaagc agaccatcaa cctgtgcgtg atcgagggcg      180
gccccctgcc cttcagcgag gacatcctga gcgccggctt caagtacggc gaccggatct      240
tcaccgagta cccccaggac atcgtggact acttcaagaa cagctgcccc gccggctaca      300
cctggggccg gagcttcctg ttcgaggacg gcgccgtgtg catctgtaac gtggacatca      360
ccgtgagcgt gaaggagaac tgcatctacc acaagagcat cttcaacggc gtgaacttcc      420
ccgccgacgg ccccgtgatg aagaagatga ccaccaactg ggaggccagc tgcgagaaga      480
tcatgcccgt gcctaagcag ggcatcctga agggcgacgt gagcatgtac ctgctgctga      540
aggacggcgg ccggtaccgg tgccagttcg acaccgtgta caaggccaag agcgtgccca      600
gcaagatgcc cgagtggcac ttcatccagc acaagctgct gcgggaggac cggagcgacg      660
ccaagaacca gaagtggcag ctgaccgagc acgccatcgc cttccccagc gccctggcct      720
gagagctcga atttccccga tcgttcaaac atttggcaat aaagtttctt aagattgaat      780
cctgttgccg gtcttgcgat gattatcata taatttctgt tgaattacgt taagcatgta      840
ataattaaca tgtaatgcat gacgttattt atgagatggg tttttatgat tagagtcccg      900
caattataca tttaatacgc gatagaaaac aaaatatagc gcgcaaacta ggataaatta      960
tcgcgcgcgg tgtcatctat gttactagat cgggaattct agtggccggc ccagctgata     1020
tccatcacac tggcggccgc tcgagttcta gtgtcacc taaatcgtat gtgtatgata      1080
cataaggtta tgtattaatt gtagccgcgt tctaacgaca atatgtccat atggtgcact     1140
ctcagtacaa tctgctctga tgccgcatag ttaagccagc cccgacaccc gccaacaccc     1200
gctgacgcgc cctgacgggc ttgtctgctc ccggcatccg cttacagaca agctgtgacc     1260
gtctccggga gctgcatgtg tcagaggttt tcaccgtcat caccgaaacg cgcgagacga     1320
aagggcctcg tgatacgcct atttttatag gttaatgtca tgaccaaaat cccttaacgt     1380
```

```
gagttttcgt tccactgagc gtcagacccc gtagaaaaga tcaaaggatc ttcttgagat    1440
cctttttttc tgcgcgtaat ctgctgcttg caaacaaaaa aaccaccgct accagcggtg    1500
gtttgtttgc cggatcaaga gctaccaact cttttttccga aggtaactgg cttcagcaga   1560
gcgcagatac caaatactgt ccttctagtg tagccgtagt taggccacca cttcaagaac   1620
tctgtagcac cgcctacata cctcgctctg ctaatcctgt taccagtggc tgctgccagt   1680
ggcgataagt cgtgtcttac cgggttggac tcaagacgat agttaccgga taaggcgcag   1740
cggtcgggct gaacggggggt ttcgtgcaca cagcccagct tggagcgaac gacctacacc   1800
gaactgagat acctcagcg tgagcattga aaaagcgcca cgcttcccga agggagaaag    1860
gcggacaggt atccggtaag cggcagggtc ggaacaggag agcgcacgag ggagcttcca   1920
gggggaaacg cctggtatct ttatagtcct gtcgggtttc gccacctctg acttgagcgt   1980
cgattttgt gatgctcgtc aggggggcgg agcctatgga aaaacgccag caacgcggcc    2040
ttttttacggt tcctggcctt ttgctggcct tttgctcaca tgttctttcc tgcgttatcc   2100
cctgattctg tggataaccg tattaccgcc tttgagtgag ctgataccgc tcgccgcagc   2160
cgaacgaccg agcgcagcga gtcagtgagc gaggaagcgg aagagcgccc aatacgcaaa   2220
ccgcctctcc ccgcgcgttg gccgattcat taatgcaggt tgatcagatc tcgatcccgc   2280
gaaattaata cgactcacta tagggagacc acaacggttt ccctctagaa ataattttgt   2340
ttaactttaa gaaggagata tacccatgga aaagcctgaa ctcaccgcga cgtctgtcga   2400
gaagtttctg atcgaaaagt tcgacagcgt ctccgacctg atgcagctct cggagggcga   2460
agaatctcgt gctttcagct tcgatgtagg agggcgtgga tatgtcctgc gggtaaatag   2520
ctgcgccgat ggtttctaca agatcgtta tgtttatcgg cactttgcat cggccgcgct   2580
cccgattccg gaagtgcttg acattgggga attcagcgag agcctgacct attgcatctc   2640
ccgccgtgca cagggtgtca cgttgcaaga acctgcctgaa accgaactgc cgctgttct   2700
gcagccggtc gcggaggcta tggatgcgat cgctgcggcc gatcttagcc agacgagcgg   2760
gttcggccca ttcggaccgc aaggaatcgg tcaatacact acatggcgtg atttcatatg   2820
cgcgattgct gatccccatg tgtatcactg gcaaactgtg atggacgaca ccgtcagtgc   2880
gtccgtcgcg caggctctcg atgagctgat gctttgggcc gaggactgcc ccgaagtccg   2940
gcacctcgtg cacgcggatt tcggctccaa caatgtcctg acggacaatg gccgcataac   3000
agcggtcatt gactggagcg aggcgatgtt cggggattcc caatacgagg tcgccaacat   3060
cttcttctgg aggccgtggt tggcttgtat ggagcagcag acgcgctact cgagcggag   3120
gcatccggag cttgcaggat cgccgcggct ccgggcgtat atgctccgca ttggtcttga   3180
ccaactctat cagagcttgg ttgacggcaa tttcgatgat gcagcttggg cgcagggtcg   3240
atgcgacgca atcgtccgat ccggagccgg gactgtcggg cgtacacaaa tcgcccgcag   3300
aagcgcggcc gtctggaccg atggctgtgt agaagtactc gccgatagtg aaaccgacg    3360
ccccagcact cgtccgaggg caaaggaata gtgaggtaca gcttggatcg atccggctgc   3420
taacaaagcc cgaaaggaag ctgagttggc tgctgccacc gctgagcaat aactagcata   3480
accccttggg gcctctaaac gggtcttgag ggtttttttg ctgaaaggag gaactatatc   3540
cggatgatcg tcgaggcctc acgtgttaac aagcttgcat gcctgcaggt ttatcaacaa   3600
gtttgtacaa aaaagcaggc tccgaattcg cccttcccac cataaggcac tttgcagggc   3660
aactgacaaa gattgataac tcaaagtacc taaattacta ttattgagaa gcattgaata   3720
```

```
taacatggtc tgttctacct aacccataaa tgttgatggt tgcatacttc agttgttaca    3780
tttaggaaaa gacagttacg aatatatcat cacagtagaa taattaattc tattttttt     3840 ttgtcataga atcttcttac taattatatc atcacttgtt agatatagaa aatattggat    3900
gttttaaaag tttttaagac ataaaatgta ttctatttaa tttttttttt ttataaaaca    3960
tcaagaagat ttataagaaa ataacatt acttattata atactatcat tattcatatt      4020
ttttaaaaaa atatctctag ctttatattt acgtgaatat gaaattaaag acatatatgt    4080
tttatctgtt tttattttc agtttttact tggtttgaaa ataattatca aaacataata     4140
aattagaaag ttacaaaatg gtaaagaaaa aactgagaag agaaacaagc acgagtttaa    4200
tttctggtga agaattagtt tatcgttggc ttcatacgaa tataacgaaa acagagtaat    4260
aaaatgttac acagtaat atacaaagat agagatataa gtagttgata aaacaattga      4320
aaaacgatga aggaaaaaag gtgaagagag aactcatgga ttccaaacct cccattaaca    4380
tttacaacaa aattaacatt tataatgtct tagaaagtat catatcacta aatgatctaa    4440
taaagaaagg agttaattag acaaaagag aagaatataa aaataaaatg actacgcatc     4500
atcaaatatc gaaaccaaca atacttatgg tgactttaat taatgatttc ggcagagttg    4560
aagtcggaaa ttataaacaa gttagtacaa atttaagtgc agccatatga aaacttttaa    4620
ttcttaggaa agtggcagca tctcttaggg ctccaaaatc attttgggg aagcagaaac     4680 ctgccaagcc acatggctat aaatatatag aaacggatga tcaagttagc caaccattat    4740
gaactctgat atacatattt gtctaaacct atagatatat attcattaat tgtatcatat    4800
tgtaggtttc agctacccg cggtcattca attgcttgca tatgttaaat gaaatcaatc     4860
agtaaaatta cctaccattc cttcacctt cacctaacaa actcaggttg aatctgtact     4920
ctatatttag tccttaaatt ctcaaatcat aacattctca ctcactataa ctaaccattg    4980
aagaagtgca atttcgtcct ctaacactct tccaaatcca agggcgaatt cgacccagct    5040
tt                                                                   5042
```

<210> SEQ ID NO 46
<211> LENGTH: 4646
<212> TYPE: DNA
<213> ORGANISM: Artificial
<220> FEATURE:
<223> OTHER INFORMATION: Nucleotide sequence of QC301-2Y

<400> SEQUENCE: 46

```
cttgtacaaa gtggttgatg ggatccatgg cccacagcaa gcacggcctg aaggaggaga      60
tgaccatgaa gtaccacatg gagggctgcg tgaacggcca caagttcgtg atcaccggcg     120
agggcatcgg ctacccttc aagggcaagc agaccatcaa cctgtgcgtg atcgagggcg      180
gccccctgcc cttcagcgag gacatcctga gcgccggctt caagtacggc gaccggatct     240
tcaccgagta ccccccaggac atcgtggact acttcaagaa cagctgcccc gccggctaca    300
cctggggccg gagcttcctg ttcgaggacg gcgccgtgtg catctgtaac gtggacatca    360
ccgtgagcgt gaaggagaac tgcatctacc acaagagcat cttcaacggc gtgaacttcc    420
ccgccgacgg ccccgtgatg aagaagatga ccaccaactg ggaggccagc tgcgagaaga   480
tcatgcccgt gcctaagcag ggcatcctga agggcgacgt gagcatgtac ctgctgctga   540 aggacgcgg ccgtaccgg tgccagttcg acaccgtgta caaggccaag agcgtgccca     600
gcaagatgcc cgagtggcac ttcatccagc acaagctgct gcgggaggac cggagcgacg   660
ccaagaacca gaagtggcag ctgaccgagc acgccatcgc cttccccagc gccctggcct   720
```

```
gagagctcga atttccccga tcgttcaaac atttggcaat aaagtttctt aagattgaat     780
cctgttgccg gtcttgcgat gattatcata taatttctgt tgaattacgt taagcatgta     840
ataattaaca tgtaatgcat gacgttattt atgagatggg tttttatgat tagagtcccg     900
caattataca tttaatacgc gatagaaaac aaaatatagc gcgcaaacta ggataaatta     960
tcgcgcgcgg tgtcatctat gttactagat cgggaattct agtggccggc cagctgata    1020
tccatcacac tggcggccgc tcgagttcta tagtgtcacc taaatcgtat gtgtatgata    1080
cataaggtta tgtattaatt gtagccgcgt tctaacgaca atatgtccat atggtgcact    1140
ctcagtacaa tctgctctga tgccgcatag ttaagccagc cccgacaccc gccaacaccc    1200
gctgacgcgc cctgacgggc ttgtctgctc ccggcatccg cttacagaca agctgtgacc    1260
gtctccggga gctgcatgtg tcagaggttt tcaccgtcat caccgaaacg cgcgagacga    1320
aagggcctcg tgatacgcct atttttatag gttaatgtca tgaccaaaat cccttaacgt    1380
gagttttcgt tccactgagc gtcagacccc gtagaaaaga tcaaaggatc ttcttgagat    1440
cctttttttc tgcgcgtaat ctgctgcttg caaacaaaaa aaccaccgct accagcggtg    1500
gtttgtttgc cggatcaaga gctaccaact cttttttccga aggtaactgg cttcagcaga    1560
gcgcagatac caaatactgt ccttctagtg tagccgtagt taggccacca cttcaagaac    1620
tctgtagcac cgcctacata cctcgctctg ctaatcctgt taccagtggc tgctgccagt    1680
ggcgataagt cgtgtcttac cgggttggac tcaagacgat agttaccgga taaggcgcag    1740
cggtcgggct gaacggggggg ttcgtgcaca cagcccagct tggagcgaac gacctacacc    1800
gaactgagat acctacagcg tgagcattga aaagcgcca cgcttcccga agggagaaag    1860
gcggacaggt atccggtaag cggcagggtc ggaacaggag agcgcacgag ggagcttcca    1920
gggggaaacg cctggtatct ttatagtcct gtcgggtttc gccacctctg acttgagcgt    1980
cgatttttgt gatgctcgtc aggggggcgg agcctatgga aaaacgccag caacgcggcc    2040
tttttacggt tcctggcctt ttgctggcct tttgctcaca tgttctttcc tgcgttatcc    2100
cctgattctg tggataaccg tattaccgcc tttgagtgag ctgataccgc tcgccgcagc    2160
cgaacgaccg agcgcagcga gtcagtgagc gaggaagcgg aagagcgccc aatacgcaaa    2220
ccgcctctcc ccgcgcgttg gccgattcat taatgcaggt tgatcagatc tcgatcccgc    2280
gaaattaata cgactcacta tagggagacc acaacggttt ccctctagaa ataattttgt    2340
ttaactttaa gaaggagata tacccatgga aaagcctgaa ctcaccgcga cgtctgtcga    2400
gaagtttctg atcgaaaagt tcgacagcgt ctccgacctg atgcagctct cggagggcga    2460
agaatctcgt gctttcagct tcgatgtagg agggcgtgga tatgtcctgc gggtaaatag    2520
ctgcgccgat ggtttctaca agatcgtta tgtttatcgg cactttgcat cggccgcgct    2580
cccgattccg gaagtgcttg acattgggga attcagcgag agcctgacct attgcatctc    2640
ccgccgtgca cagggtgtca cgttgcaaga cctgcctgaa accgaactgc cgctgttct    2700
gcagccggtc gcggaggcta tggatgcgat cgctgcggcc gatcttagcc agacgagcgg    2760
gttcggccca ttcggaccgc aaggaatcgg tcaatacact acatggcgtg atttcatatg    2820
cgcgattgct gatccccatg tgtatcactg gcaaactgtg atggacgaca ccgtcagtgc    2880
gtccgtcgcg caggctctcg atgagctgat gctttgggcc gaggactgcc ccgaagtccg    2940
gcacctcgtg cacgcggatt tcggctccaa caatgtcctg acggacaatg gccgcataac    3000
agcggtcatt gactggagcg aggcgatgtt cggggattcc caatacgagg tcgccaacat    3060
```

```
cttcttctgg aggccgtggt tggcttgtat ggagcagcag acgcgctact tcgagcggag    3120
gcatccggag cttgcaggat cgccgcggct ccgggcgtat atgctccgca ttggtcttga    3180
ccaactctat cagagcttgg ttgacggcaa tttcgatgat gcagcttggg cgcagggtcg    3240
atgcgacgca atcgtccgat ccggagccgg gactgtcggg cgtacacaaa tcgcccgcag    3300
aagcgcggcc gtctggaccg atggctgtgt agaagtactc gccgatagtg gaaaccgacg    3360
ccccagcact cgtccgaggg caaaggaata gtgaggtaca gcttggatcg atccggctgc    3420
taacaaagcc cgaaaggaag ctgagttggc tgctgccacc gctgagcaat aactagcata    3480
acccccttggg gcctctaaac gggtcttgag gggttttttg ctgaaaggag gaactatatc    3540
cggatgatcg tcgaggcctc acgtgttaac aagcttgcat gcctgcaggt ttatcaacaa    3600
gtttgtacaa aaaagcaggc tccgaattcg ccctttatct ctagctttat atttacgtga    3660
atatgaaatt aaagacatat atgttttatc tgtttttatt tttcagtttt tacttggttt    3720
gaaaataatt atcaaaacat aataaattag aaagttacaa aatggtaaag aaaaaactga    3780
gaagagaaac aagcacgagt ttaatttctg gtgaagaatt agtttatcgt tggcttcata    3840
cgaatataac gaaaacagag taataaaatg ttacacagag taatatacaa agatagagat    3900
ataagtagtt gataaaacaa ttgaaaaacg atgaaggaaa aaaggtgaag agagaactca    3960
tggattccaa acctcccatt aacatttaca acaaaattaa catttataat gtcttagaaa    4020
gtatcatatc actaaatgat ctaataaaga aaggagttaa ttagacaaaa agagaagaat    4080
ataaaaataa aatgactacg catcatcaaa tatcgaaacc aacaatactt atggtgactt    4140
taattaatga tttcggcaga gttgaagtcg gaaattataa acaagttagt acaaatttaa    4200
gtgcagccat atgaaaactt ttaattctta ggaaagtggc agcatctctt agggctccaa    4260
aatcattttg ggggaagcag aaacctgcca agcacatgg ctataaatat atagaaacgg    4320
atgatcaagt tagccaacca ttatgaactc tgatatacat attttgtctaa acctatagat    4380
atatattcat taattgtatc atattgtagg tttcagctac cccgcggtca ttcaattgct    4440
tgcatatgtt aaatgaaatc aatcagtaaa attacctacc attccttcac ctttcaccta    4500
acaaactcag gttgaatctg tactctatat ttagtcctta aattctcaaa tcataacatt    4560
ctcactcact ataactaacc attgaagaag tgcaatttcg tcctctaaca ctcttccaaa    4620
tccaagggcg aattcgaccc agcttt                                        4646
```

<210> SEQ ID NO 47
<211> LENGTH: 4340
<212> TYPE: DNA
<213> ORGANISM: Artificial
<220> FEATURE:
<223> OTHER INFORMATION: Nucleotide sequence of QC301-3Y

<400> SEQUENCE: 47

```
cttgtacaaa gtggttgatg ggatccatgg cccacagcaa gcacggcctg aaggaggaga      60
tgaccatgaa gtaccacatg gagggctgcg tgaacggcca caagttcgtg atcaccggcg     120
agggcatcgg ctacccttc aagggcaagc agaccatcaa cctgtgcgtg atcgagggcg     180
gcccctgcc cttcagcgag gacatcctga gcgccggctt caagtacggc gaccggatct     240
tcaccgagta cccccaggac atcgtggact acttcaagaa cagctgcccc gccggctaca     300
cctggggccg gagcttcctg ttcgaggacg gcgccgtgtg catctgtaac gtggacatca     360
ccgtgagcgt gaaggagaac tgcatctacc acaagagcat cttcaacggc gtgaacttcc     420
ccgccgacgg ccccgtgatg aagaagatga ccaccaactg ggaggccagc tgcgagaaga     480
```

```
tcatgcccgt gcctaagcag ggcatcctga agggcgacgt gagcatgtac ctgctgctga    540
aggacggcgg ccggtaccgg tgccagttcg acaccgtgta caaggccaag agcgtgccca    600
gcaagatgcc cgagtggcac ttcatccagc acaagctgct gcgggaggac cggagcgacg    660
ccaagaacca gaagtggcag ctgaccgagc acgccatcgc cttccccagc gccctggcct    720
gagagctcga atttccccga tcgttcaaac atttggcaat aaagtttctt aagattgaat    780
cctgttgccg tcttgcgat gattatcata taatttctgt tgaattacgt taagcatgta    840
ataattaaca tgtaatgcat gacgttattt atgagatggg tttttatgat tagagtcccg    900
caattataca tttaatacgc gatagaaaac aaaatatagc gcgcaaacta ggataaatta    960
tcgcgcgcgg tgtcatctat gttactagat cgggaattct agtggccggc cagctgata    1020 tccatcacac tggcggccgc tcgagttcta tagtgtcacc taaatcgtat gtgtatgata    1080
cataaggtta tgtattaatt gtagccgcgt tctaacgaca atatgtccat atggtgcact    1140
ctcagtacaa tctgctctga tgccgcatag ttaagccagc ccgacaccc gccaacaccc    1200 gctgacgcgc cctgacgggc ttgtctgctc ccggcatccg cttacagaca agctgtgacc    1260
gtctccggga gctgcatgtg tcagaggttt tcaccgtcat caccgaaacg cgcgagacga    1320
aagggcctcg tgatacgcct atttttatag gttaatgtca tgaccaaaat cccttaacgt    1380
gagttttcgt tccactgagc gtcagacccc gtagaaaaga tcaaaggatc ttcttgagat    1440 ccttttttc tgcgcgtaat ctgctgcttg caaacaaaaa aaccaccgct accagcggtg    1500
gtttgtttgc cggatcaaga gctaccaact ctttttccga aggtaactgg cttcagcaga    1560
gcgcagatac caaatactgt ccttctagtg tagccgtagt taggccacca cttcaagaac    1620
tctgtagcac cgcctacata cctcgctctg ctaatcctgt taccagtggc tgctgccagt    1680
ggcgataagt cgtgtcttac cgggttggac tcaagacgat agttaccgga taaggcgcag    1740
cggtcgggct gaacggggg ttcgtgcaca cagcccagct tggagcgaac gacctacacc    1800
gaactgagat acctacagcg tgagcattga aaagcgcca cgcttcccga agggagaaag    1860
gcggacaggt atccggtaag cggcagggtc ggaacaggag agcgcacgag ggagcttcca    1920
gggggaaacg cctggtatct ttatagtcct gtcgggtttc gccacctctg acttgagcgt    1980
cgatttttgt gatgctcgtc aggggggcgg agcctatgga aaaacgccag caacgcggcc    2040 ttttacggt tcctggcctt tgctggcct tttgctcaca tgttctttcc tgcgttatcc    2100
cctgattctg tggataaccg tattaccgcc tttgagtgag ctgataccgc tcgccgcagc    2160
cgaacgaccg agcgcagcga gtcagtgagc gaggaagcgg aagagcgccc aatacgcaaa    2220
ccgcctctcc ccgcgcgttg gccgattcat taatgcaggt tgatcagatc tcgatcccgc    2280
gaaattaata cgactcacta tagggagacc acaacggttt ccctctagaa ataattttgt    2340
ttaactttaa gaaggagata tacccatgga aaagcctgaa ctcaccgcga cgtctgtcga    2400
gaagtttctg atcgaaaagt tcgacagcgt ctccgacctg atgcagctct cggagggcga    2460
agaatctcgt gctttcagct tcgatgtagg agggcgtgga tatgtcctgc gggtaaatag    2520
ctgcgccgat ggtttctaca agatcgtta tgtttatcgg cactttgcat cggccgcgct    2580
cccgattccg gaagtgcttg acattgggga attcagcgag agcctgacct attgcatctc    2640
ccgccgtgca cagggtgtca cgttgcaaga cctgcctgaa accgaactgc ccgctgttct    2700
gcagccggtc gcggaggcta tggatgcgat cgctgcggcc gatcttagcc agacgagcgg    2760
gttcggccca ttcggaccgc aaggaatcgg tcaatacact acatggcgtg atttcatatg    2820
```

```
cgcgattgct gatccccatg tgtatcactg gcaaactgtg atggacgaca ccgtcagtgc    2880
gtccgtcgcg caggctctcg atgagctgat gctttgggcc gaggactgcc ccgaagtccg    2940
gcacctcgtg cacgcggatt tcggctccaa caatgtcctg acggacaatg ccgcataac     3000 agcggtcatt gactggagcg aggcgatgtt cggggattcc caatacgagg tcgccaacat    3060
cttcttctgg aggccgtggt tggcttgtat ggagcagcag acgcgctact tcgagcggag    3120
gcatccggag cttgcaggat cgccgcggct ccgggcgtat atgctccgca ttggtcttga    3180
ccaactctat cagagcttgg ttgacggcaa tttcgatgat gcagcttggg cgcagggtcg    3240
atgcgacgca atcgtccgat ccggagccgg gactgtcggg cgtacacaaa tcgcccgcag    3300
aagcgcggcc gtctggaccg atggctgtgt agaagtactc gccgatagtg gaaaccgacg    3360
ccccagcact cgtccgaggg caaaggaata gtgaggtaca gcttggatcg atccggctgc    3420
taacaaagcc cgaaaggaag ctgagttggc tgctgccacc gctgagcaat aactagcata    3480
accccttggg gcctctaaac gggtcttgag gggttttttg ctgaaaggag gaactatatc    3540
cggatgatcg tcgaggcctc acgtgttaac aagcttgcat gcctgcaggt ttatcaacaa    3600
gtttgtacaa aaaagcaggc tccgaattcg cccttaaggt gaagagagaa ctcatggatt    3660
ccaaacctcc cattaacatt tacaacaaaa ttaacattta taatgtctta gaaagtatca    3720
tatcactaaa tgatctaata agaaaggag ttaattagac aaaagagaa gaatataaaa       3780 ataaaatgac tacgcatcat caaatatcga aaccaacaat acttatgtg actttaatta     3840 atgatttcgg cagagttgaa gtcggaaatt ataaacaagt tagtacaaat ttaagtgcag    3900
ccatatgaaa acttttaatt cttaggaaag tggcagcatc tcttagggct ccaaaatcat    3960
tttgggggaa gcagaaacct gccaagccac atggctataa atatatagaa acggatgatc    4020
aagttagcca accattatga actctgatat acatatttgt ctaaacctat agatatatat    4080
tcattaattg tatcatattg taggtttcag ctaccccgcg gtcattcaat tgcttgcata    4140
tgttaaatga aatcaatcag taaaattacc taccattcct tcacctttca cctaacaaac    4200
tcaggttgaa tctgtactct atatttagtc cttaaattct caaatcataa cattctcact    4260
cactataact aaccattgaa gaagtgcaat ttcgtcctct aacactcttc caaatccaag    4320
ggcgaattcg acccagcttt                                                4340
```

<210> SEQ ID NO 48
<211> LENGTH: 4051
<212> TYPE: DNA
<213> ORGANISM: Artificial
<220> FEATURE:
<223> OTHER INFORMATION: Nucleotide sequence of QC301-4Y

<400> SEQUENCE: 48

```
cttgtacaaa gtggttgatg ggatccatgg cccacagcaa gcacggcctg aaggaggaga     60
tgaccatgaa gtaccacatg gagggctgcg tgaacggcca caagttcgtg atcaccggcg    120
agggcatcgg ctacccccttc aagggcaagc agaccatcaa cctgtgcgtg atcgagggcg    180 gcccccctgcc cttcagcgag gacatcctga gcgccggctt caagtacggc gaccggatct    240
tcaccgagta cccccaggac atcgtggact acttcaagaa cagctgcccc gccggctaca    300
cctggggccg gagcttcctg ttcgaggacg gcgccgtgtg catctgtaac gtggacatca    360
ccgtgagcgt gaaggagaac tgcatctacc acaagagcat cttcaacggc gtgaacttcc    420
ccgccgacgg ccccgtgatg aagaagatga ccaccaactg ggaggccagc tgcgagaaga    480
tcatgcccgt gcctaagcag ggcatcctga agggcgacgt gagcatgtac ctgctgctga    540
```

```
aggacggcgg ccggtaccgg tgccagttcg acaccgtgta caaggccaag agcgtgccca    600
gcaagatgcc cgagtggcac ttcatccagc acaagctgct gcgggaggac cggagcgacg    660
ccaagaacca gaagtggcag ctgaccgagc acgccatcgc cttccccagc gccctggcct    720
gagagctcga atttccccga tcgttcaaac atttggcaat aaagtttctt aagattgaat    780
cctgttgccg gtcttgcgat gattatcata taatttctgt tgaattacgt taagcatgta    840
ataattaaca tgtaatgcat gacgttattt atgagatggg ttttatgat tagagtcccg      900 caattataca tttaatacgc gatagaaaac aaaatatagc gcgcaaacta ggataaatta    960
tcgcgcgcgg tgtcatctat gttactagat cgggaattct agtggccggc cagctgata    1020 tccatcacac tggcggccgc tcgagttcta tagtgtcacc taaatcgtat gtgtatgata   1080
cataaggtta tgtattaatt gtagccgcgt tctaacgaca atatgtccat atggtgcact    1140
ctcagtacaa tctgctctga tgccgcatag ttaagccagc ccgacacccc gccaacaccc   1200
gctgacgcgc cctgacgggc ttgtctgctc ccggcatccg cttacagaca agctgtgacc   1260
gtctccggga gctgcatgtg tcagaggttt tcaccgtcat caccgaaacg cgcgagacga   1320
aagggcctcg tgatacgcct atttttatag gttaatgtca tgaccaaaat cccttaacgt    1380
gagttttcgt tccactgagc gtcagacccc gtagaaaaga tcaaaggatc ttcttgagat    1440 ccttttttc tgcgcgtaat ctgctgcttg caaacaaaaa aaccaccgct accagcggtg    1500
gtttgtttgc cggatcaaga gctaccaact ctttttccga aggtaactgg cttcagcaga   1560
gcgcagatac caaatactgt ccttctagtg tagccgtagt taggccacca cttcaagaac   1620
tctgtagcac cgcctacata cctcgctctg ctaatcctgt taccagtggc tgctgccagt    1680
ggcgataagt cgtgtcttac cgggttggac tcaagacgat agttaccgga taaggcgcag   1740
cggtcgggct gaacggggggg ttcgtgcaca cagcccagct tggagcgaac gacctacacc   1800
gaactgagat acctacagcg tgagcattga gaaagcgcca cgcttcccga agggagaaag   1860
gcggacaggt atccggtaag cggcagggtc ggaacaggag agcgcacgag ggagcttcca   1920
gggggaaacg cctggtatct ttatagtcct gtcgggtttc gccacctctg acttgagcgt   1980
cgatttttgt gatgctcgtc aggggggcgg agcctatgga aaaacgccag caacgcggcc   2040 ttttacggt tcctggcctt ttgctggcct tttgctcaca tgttctttcc tgcgttatcc    2100
cctgattctg tggataaccg tattaccgcc tttgagtgag ctgataccgc tcgccgcagc   2160
cgaacgaccg agcgcagcga gtcagtgagc gaggaagcgg aagagcgccc aatacgcaaa   2220
ccgcctctcc ccgcgcgttg gccgattcat taatgcaggt tgatcagatc tcgatcccgc    2280
gaaattaata cgactcacta tagggagacc acaacggttt ccctctagaa ataattttgt   2340
ttaactttaa gaaggagata tacccatgga aaagcctgaa ctcaccgcga cgtctgtcga   2400
gaagtttctg atcgaaaagt tcgacagcgt ctccgacctg atgcagctct cggagggcga   2460
agaatctcgt gctttcagct tcgatgtagg agggcgtgga tatgtcctgc gggtaaatag    2520
ctgcgccgat ggtttctaca agatcgtta tgtttatcgg cactttgcat cggccgcgct    2580
cccgattccg gaagtgcttg acattgggga attcagcgag agcctgacct attgcatctc   2640
ccgccgtgca cagggtgtca cgttgcaaga cctgcctgaa accgaactgc cgctgttct    2700 gcagccggtc gcggaggcta tggatgcgat cgctgcggcc gatcttagcc agacgagcgg    2760
gttcggccca ttcggaccgc aaggaatcgg tcaatacact acatggcgtg atttcatatg   2820
cgcgattgct gatccccatg tgtatcactg gcaaactgtg atggacgaca ccgtcagtgc   2880
```

```
gtccgtcgcg caggctctcg atgagctgat gctttgggcc gaggactgcc ccgaagtccg    2940
gcacctcgtg cacgcggatt tcggctccaa caatgtcctg acggacaatg gccgcataac    3000
agcggtcatt gactggagcg aggcgatgtt cggggattcc caatacgagg tcgccaacat    3060
cttcttctgg aggccgtggt tggcttgtat ggagcagcag acgcgctact tcgagcggag    3120
gcatccggag cttgcaggat cgccgcggct ccgggcgtat atgctccgca ttggtcttga    3180
ccaactctat cagagcttgg ttgacggcaa tttcgatgat gcagcttggg cgcagggtcg    3240
atgcgacgca atcgtccgat ccggagccgg gactgtcggg cgtacacaaa tcgcccgcag    3300
aagcgcggcc gtctggaccg atggctgtgt agaagtactc gccgatagtg aaaccgacg    3360 ccccagcact cgtccgaggg caaaggaata gtgaggtaca gcttggatcg atccggctgc    3420
taacaaagcc cgaaggaag ctgagttggc tgctgccacc gctgagcaat aactagcata    3480
accccttggg gcctctaaac gggtcttgag gggttttttg ctgaaaggag gaactatatc    3540
cggatgatcg tcgaggcctc acgtgttaac aagcttgcat gcctgcaggt ttatcaacaa    3600
gtttgtacaa aaaagcaggc tccgaattcg cccttggaaa gtggcagcat ctcttagggc    3660
tccaaaatca ttttggggga agcagaaacc tgccaagcca catggctata aatatataga    3720
aacggatgat caagttagcc aaccattatg aactctgata tacatatttg tctaaaccta    3780
tagatatata ttcattaatt gtatcatatt gtaggtttca gctaccccgc ggtcattcaa    3840
ttgcttgcat atgttaaatg aaatcaatca gtaaaattac ctaccattcc ttcacctttc    3900
acctaacaaa ctcaggttga atctgtactc tatatttagt ccttaaattc tcaaatcata    3960
acattctcac tcactataac taaccattga agaagtgcaa tttcgtcctc taacactctt    4020
ccaaatccaa gggcgaattc gacccagctt t                                   4051
```

<210> SEQ ID NO 49
<211> LENGTH: 3882
<212> TYPE: DNA
<213> ORGANISM: Artificial
<220> FEATURE:
<223> OTHER INFORMATION: Nucleotide sequence of QC301-5Y

<400> SEQUENCE: 49

```
cttgtacaaa gtggttgatg ggatccatgg cccacagcaa gcacggcctg aaggaggaga      60
tgaccatgaa gtaccacatg gagggctgcg tgaacggcca caagttcgtg atcaccggcg     120
agggcatcgg ctacccttc aagggcaagc agaccatcaa cctgtgcgtg atcgagggcg     180 gcccctgcc cttcagcgag gacatcctga gcgccggctt caagtacggc gaccggatct     240
tcaccgagta ccccccagga catcgtggact acttcaagaa cagctgcccc gccggctaca     300
cctggggccg gagcttcctg ttcgaggacg gcgccgtgtg catctgtaac gtggacatca     360
ccgtgagcgt gaaggagaac tgcatctacc acaagagcat cttcaacggc gtgaacttcc     420
ccgccgacgg ccccgtgatg aagaagatga ccaccaactg ggaggccagc tgcgagaaga     480
tcatgcccgt gcctaagcag ggcatcctga agggcgacgt gagcatgtac ctgctgctga     540
aggacggcgg ccggtaccgg tgccagttcg acaccgtgta caaggccaag agcgtgccca     600
gcaagatgcc cgagtggcac ttcatccagc acaagctgct gcgggaggac cggagcgacg     660
ccaagaacca gaagtggcag ctgaccgagc acgccatcgc cttccccagc gccctggcct     720
gagagctcga atttccccga tcgttcaaac atttggcaat aaagtttctt aagattgaat     780
cctgttgccg gtcttgcgat gattatcata taatttctgt tgaattacgt taagcatgta     840
ataattaaca tgtaatgcat gacgttattt atgagatggg ttttttatgat tagagtcccg     900
```

```
caattataca tttaatacgc gatagaaaac aaaatatagc gcgcaaacta ggataaatta    960
tcgcgcgcgg tgtcatctat gttactagat cgggaattct agtggccggc ccagctgata   1020
tccatcacac tggcggccgc tcgagttcta tagtgtcacc taaatcgtat gtgtatgata   1080
cataaggtta tgtattaatt gtagccgcgt tctaacgaca atatgtccat atggtgcact   1140
ctcagtacaa tctgctctga tgccgcatag ttaagccagc cccgacaccc gccaacaccc   1200
gctgacgcgc cctgacgggc ttgtctgctc ccggcatccg cttacagaca agctgtgacc   1260
gtctccggga gctgcatgtg tcagaggttt tcaccgtcat caccgaaacg cgcgagacga   1320
aagggcctcg tgatacgcct attttttatag gttaatgtca tgaccaaaat cccttaacgt   1380
gagttttcgt tccactgagc gtcagacccc gtagaaaaga tcaaaggatc ttcttgagat   1440
ccttttttc tgcgcgtaat ctgctgcttg caaacaaaaa aaccaccgct accagcggtg   1500
gtttgtttgc cggatcaaga gctaccaact cttttccga aggtaactgg cttcagcaga   1560
gcgcagatac caaatactgt ccttctagtg tagccgtagt taggccacca cttcaagaac   1620
tctgtagcac cgcctacata cctcgctctg ctaatcctgt taccagtggc tgctgccagt   1680
ggcgataagt cgtgtcttac cgggttggac tcaagacgat agttaccgga taaggcgcag   1740
cggtcgggct gaacggggggg ttcgtgcaca cagcccagct tggagcgaac gacctacacc   1800
gaactgagat acctacagcg tgagcattga aaagcgcca cgcttcccga agggagaaag   1860
gcggacaggt atccggtaag cggcagggtc ggaacaggag agcgcacgag ggagcttcca   1920
gggggaaacg cctggtatct ttatagtcct gtcgggtttc gccacctctg acttgagcgt   1980
cgattttgt gatgctcgtc aggggggcgg agcctatgga aaaacgccag caacgcggcc   2040
ttttttacggt tcctggcctt ttgctggcct tttgctcaca tgttctttcc tgcgttatcc   2100
cctgattctg tggataaccg tattaccgcc tttgagtgag ctgataccgc tcgccgcagc   2160
cgaacgaccg agcgcagcga gtcagtgagc gaggaagcgg aagagcgccc aatacgcaaa   2220
ccgcctctcc ccgcgcgttg gccgattcat taatgcaggt tgatcagatc tcgatcccgc   2280
gaaattaata cgactcacta tagggagacc acaacggttt ccctctagaa ataattttgt   2340
ttaactttaa gaaggagata tacccatgga aaagcctgaa ctcaccgcga cgtctgtcga   2400
gaagtttctg atcgaaaagt tcgacagcgt ctccgacctg atgcagctct cggagggcga   2460
agaatctcgt gctttcagct tcgatgtagg agggcgtgga tatgtcctgc gggtaaatag   2520
ctgcgccgat ggtttctaca agatcgtta tgtttatcgg cactttgcat cggccgcgct   2580
cccgattccg gaagtgcttg acattgggga attcagcgag agcctgacct attgcatctc   2640
ccgccgtgca cagggtgtca cgttgcaaga cctgcctgaa accgaactgc ccgctgttct   2700
gcagccggtc gcggaggcta tggatgcgat cgctgcggcc gatcttagcc agacgagcgg   2760
gttcggccca ttcggaccgc aaggaatcgg tcaatacact acatggcgtg atttcatatg   2820
cgcgattgct gatccccatg tgtatcactg gcaaactgtg atggacgaca ccgtcagtgc   2880
gtccgtcgcg caggctctcg atgagctgat gctttgggcc gaggactgcc ccgaagtccg   2940
gcacctcgtg cacgcggatt tcggctccaa caatgtcctg acggacaatg gccgcataac   3000
agcggtcatt gactggagcg aggcgatgtt cggggattcc caatacgagg tcgccaacat   3060
cttcttctgg aggccgtggt tggcttgtat ggagcagcag acgcgctact cgagcggag   3120
gcatccggag cttgcaggat cgccgcggct ccgggcgtat atgctccgca ttggtcttga   3180
ccaactctat cagagcttgg ttgacggcaa tttcgatgat gcagcttggg cgcagggtcg   3240
```

```
atgcgacgca atcgtccgat ccggagccgg gactgtcggg cgtacacaaa tcgcccgcag    3300
aagcgcggcc gtctggaccg atggctgtgt agaagtactc gccgatagtg gaaaccgacg    3360
ccccagcact cgtccgaggg caaaggaata gtgaggtaca gcttggatcg atccggctgc    3420
taacaaagcc cgaaaggaag ctgagttggc tgctgccacc gctgagcaat aactagcata    3480
accccttggg gcctctaaac gggtcttgag gggttttttg ctgaaaggag gaactatatc    3540
cggatgatcg tcgaggcctc acgtgttaac aagcttgcat gcctgcaggt ttatcaacaa    3600
gtttgtacaa aaaagcaggc tccgaattcg cccttcatat tgtaggtttc agctaccccg    3660
cggtcattca attgcttgca tatgttaaat gaaatcaatc agtaaaatta cctaccattc    3720
cttcaccttt cacctaacaa actcaggttg aatctgtact ctatatttag tccttaaatt    3780
ctcaaatcat aacattctca ctcactataa ctaaccattg aagaagtgca atttcgtcct    3840
ctaacactct tccaaatcca agggcgaatt cgacccagct tt                       3882
```

<210> SEQ ID NO 50
<211> LENGTH: 4157
<212> TYPE: DNA
<213> ORGANISM: Artificial
<220> FEATURE:
<223> OTHER INFORMATION: Nucleotide sequence of pZSL90

<400> SEQUENCE: 50

```
gatccatggc ccacagcaag cacggcctga aggaggagat gaccatgaag taccacatgg      60
agggctgcgt gaacggccac aagttcgtga tcaccggcga gggcatcggc tacccccttca    120
agggcaagca gaccatcaac ctgtgcgtga tcgagggcgg ccccctgccc ttcagcgagg    180
acatcctgag cgccggcttc aagtacggcg accggatctt caccgagtac ccccaggaca    240
tcgtggacta cttcaagaac agctgccccc ccggctacac ctggggccgg agcttcctgt    300
tcgaggacgg cgccgtgtgc atctgtaacg tggacatcac cgtgagcgtg aaggagaact    360
gcatctacca caagagcatc ttcaacggcg tgaacttccc cgccgacggc cccgtgatga    420
agaagatgac caccaactgg gaggccagct gcgagaagat catgcccgtg cctaagcagg    480
gcatcctgaa gggcgacgtg agcatgtacc tgctgctgaa ggacggcggc cggtaccggt    540
gccagttcga caccgtgtac aaggccaaga gcgtgcccag caagatgccc gagtggcact    600
tcatccagca caagctgctg cgggaggacc ggagcgacgc caagaaccag aagtggcagc    660
tgaccgagca cgccatcgcc ttccccagcg ccctggcctg agagctcgaa tttccccgat    720
cgttcaaaca tttggcaata aagtttctta agattgaatc ctgttgccgg tcttgcgatg    780
attatcatat aatttctgtt gaattacgtt aagcatgtaa taattaacat gtaatgcatg    840
acgttattta tgagatgggt ttttatgatt agagtcccgc aattatacat ttaatacgcg    900
atagaaaaca aaatatagcg cgcaaactag gataaattat cgcgcgcggt gtcatctatg    960
ttactagatc gggaattcta gtggccggcc cagctgatat ccatcacact ggcggccgct   1020
cgagttctat agtgtcacct aaatcgtatg tgtatgatac ataaggttat gtattaattg   1080
tagccgcgtt ctaacgacaa tatgtccata tggtgcactc tcagtacaat ctgctctgat   1140
gccgcatagt taagccagcc ccgacacccg ccaacacccg ctgacgcgcc ctgacgggct   1200
tgtctgctcc cggcatccgc ttacagacaa gctgtgaccg tctccgggag ctgcatgtgt   1260
cagaggtttt caccgtcatc accgaaacgc gcgagacgaa agggcctcgt gatacgccta   1320
tttttatagg ttaatgtcat gaccaaaatc ccttaacgtg agttttcgtt ccactgagcg   1380
tcagaccccg tagaaaagat caaaggatct tcttgagatc ctttttttct gcgcgtaatc   1440
```

```
tgctgcttgc aaacaaaaaa accaccgcta ccagcggtgg tttgtttgcc ggatcaagag    1500
ctaccaactc ttttttccgaa ggtaactggc ttcagcagag cgcagatacc aaatactgtc   1560
cttctagtgt agccgtagtt aggccaccac ttcaagaact ctgtagcacc gcctacatac   1620
ctcgctctgc taatcctgtt accagtggct gctgccagtg gcgataagtc gtgtcttacc   1680
gggttggact caagacgata gttaccggat aaggcgcagc ggtcgggctg aacgggggggt  1740 tcgtgcacac agcccagctt ggagcgaacg acctacaccg aactgagata cctacagcgt   1800
gagcattgag aaagcgccac gcttcccgaa gggagaaagg cggacaggta tccggtaagc   1860
ggcagggtcg aacaggaga gcgcacgagg gagcttccag ggggaaacgc ctggtatctt     1920
tatagtcctg tcgggtttcg ccacctctga cttgagcgtc gatttttgtg atgctcgtca   1980
ggggggcgga gcctatggaa aaacgccagc aacgcggcct ttttacggtt cctgcctttt   2040
tgctggcctt ttgctcacat gttctttcct gcgttatccc ctgattctgt ggataaccgt   2100
attaccgcct ttgagtgagc tgataccgct cgccgcagcc gaacgaccga gcgcagcgag   2160
tcagtgagcg aggaagcgga agagcgccca atacgcaaac cgcctctccc cgcgcgttgg   2220
ccgattcatt aatgcaggtt gatcagatct cgatcccgcg aaattaatac gactcactat   2280
agggagacca aacggtttc cctctagaaa taattttgtt taactttaag aaggagatat    2340
acccatggaa aagcctgaac tcaccgcgac gtctgtcgag aagtttctga tcgaaaagtt   2400
cgacagcgtc tccgacctga tgcagctctc ggagggcgaa gaatctcgtg ctttcagctt    2460
cgatgtagga gggcgtggat atgtcctgcg ggtaaatagc tgcgccgatg gtttctacaa   2520
agatcgttat gtttatcggc actttgcatc ggccgcgctc ccgattccgg aagtgcttga   2580
cattggggaa ttcagcgaga gcctgaccta ttgcatctcc cgccgtgcac agggtgtcac   2640
gttgcaagac ctgcctgaaa ccgaactgcc cgctgttctg cagccggtcg cggaggctat   2700
ggatgcgatc gctgcggccg atcttagcca gacgagcggg ttcggcccat tcggaccgca   2760
aggaatcggt caatacacta catggcgtga tttcatatgc gcgattgctg atccccatgt   2820
gtatcactgg caaactgtga tggacgacac cgtcagtgcg tccgtcgcgc aggctctcga   2880
tgagctgatg ctttgggccg aggactgccc cgaagtccgg cacctcgtgc acgcggattt   2940
cggctccaac aatgtcctga cggacaatgg ccgcataaca gcggtcattg actggagcga    3000
ggcgatgttc ggggattccc aatacgaggt cgccaacatc ttcttctgga ggccgtggtt   3060
ggcttgtatg gagcagcaga cgcgctactt cgagcggagg catccggagc ttgcaggatc   3120
gccgcggctc cgggcgtata tgctccgcat tggtcttgac caactctatc agagcttggt   3180
tgacggcaat ttcgatgatg cagcttgggc gcagggtcga tgcgacgcaa tcgtccgatc   3240
cggagccggg actgtcgggc gtacacaaat cgcccgcaga agcgcggccg tctggaccga   3300
tggctgtgta gaagtactcg ccgatagtgg aaaccgacgc cccagcactc gtccgagggc   3360
aaaggaatag tgaggtacag cttggatcga tccggctgct aacaaagccc gaaaggaagc   3420
tgagttggct gctgccaccg ctgagcaata actagcataa ccccttgggg cctctaaacg   3480
ggtcttgagg ggttttttgc tgaaaggagg aactatatcc ggatgatcgt cgaggcctca   3540
cgtgttaaca agcttgcatg cctgcaggtt taaacagtcg actctagaga tccgtcaaca   3600
tggtggagca cgacactctc gtctactcca agaatatcaa agatacagtc tcagaagacc   3660
aaagggctat tgagactttt caacaaaggg taatatcggg aaacctcctc ggattccatt   3720
gcccagctat ctgtcacttc atcaaaagga cagtagaaaa ggaaggtggc acctacaaat   3780
```

| | | | | | | |
|---|---|---|---|---|---|---|
| gccatcattg | cgataaagga | aaggctatcg | ttcaagatgc | ctctgccgac | agtggtccca | 3840 |
| aagatggacc | cccacccacg | aggagcatcg | tggaaaaaga | agacgttcca | accacgtctt | 3900 |
| caaagcaagt | ggattgatgt | gatgatccta | tgcgtatggt | atgacgtgtg | ttcaagatga | 3960 |
| tgacttcaaa | cctacctatg | acgtatggta | tgacgtgtgt | cgactgatga | cttagatcca | 4020 |
| ctcgagcggc | tataaatacg | tacctacgca | ccctgcgcta | ccatccctag | agctgcagct | 4080 |
| tatttttaca | acaattacca | acaacaacaa | acaacaaaca | acattacaat | tactatttac | 4140 |
| aattacagtc | gacccgg | | | | | 4157 |

SOYBEAN PROMOTERS LTP2 AND FLOWER-PREFERRED EXPRESSION THEREOF IN TRANSGENIC PLANTS

CROSS-REFERENCE TO RELATED APPLICATION

This application claims the benefit of U.S. Provisional Application Ser. No. 60/930,878, filed May 17, 2007, which is incorporated by reference herein in its entirety.

FIELD OF THE INVENTION

The present invention relates to the field of plant molecular biology, more particularly to regulation of gene expression in plants.

BACKGROUND OF THE INVENTION

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities can be incorporated properly into the plant's genome. The newly integrated gene (or genes) coding sequence can then be expressed in the plant cell to exhibit the desired new trait or characteristic. It is important that appropriate regulatory signals be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the RNA polymerase binding and other related protein factors that attach to the RNA polymerase and/or promoter, and the rate of RNA synthesis.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters", if the promoters direct RNA synthesis preferentially in certain tissues (RNA synthesis may occur in other tissues at reduced levels). Since patterns of expression of a chimeric gene (or genes) introduced into a plant are controlled using promoters, there is an ongoing interest in the isolation of novel promoters that are capable of controlling the expression of a chimeric gene (or genes) at certain levels in specific tissue types or at specific plant developmental stages.

Among the most commonly used promoters are the nopaline synthase (NOS) promoter (Ebert et al., Proc. Natl. Acad. Sci. U.S.A. 84:5745-5749 (1987)); the octapine synthase (OCS) promoter, caulimovirus promoters such as the cauliflower mosaic virus (CaMV) 19S promoter (Lawton et al., Plant Mol. Biol. 9:315-324 (1987)); the CaMV 35S promoter (Odell et al., Nature 313:810-812 (1985)), and the figwort mosaic virus 35S promoter (Sanger et al., Plant Mol. Biol. 14:433-43 (1990)); the light inducible promoter from the small subunit of rubisco (Pellegrineschi et al., Biochem. Soc. Trans. 23(2):247-250 (1995)); the Adh promoter (Walker et al., Proc. Natl. Acad. Sci. U.S.A. 84:6624-66280 (1987)); the sucrose synthase promoter (Yang et al., Proc. Natl. Acad. Sci. U.S.A. 87:4144-4148 (1990)); the R gene complex promoter (Chandler et al., Plant Cell 1:1175-1183 (1989)); the chlorophyll a/b binding protein gene promoter; and the like.

An angiosperm flower is a complex structure generally consisting of a pedicel, sepals, petals, stamens, and a pistil. A stamen comprises a filament and an anther in which the male gametophyte pollens reside. A pistil comprises a stigma, style and ovary. An ovary contains one or more ovules in which the female gametophyte embryo sac, egg cell, central cell, and other specialized cells reside. Flower promoters in general include promoters that direct gene expression in any of the above tissues or cell types. Lipid transfer protein (LTP) genes have been isolated from barley (Federico et al., Plant Mol. Biol. 57:35-51 (2005)), strawberry (Yubero-Serrano et al, J. Exp. Bot. 54:1865-1877 (2003)), Arabidopsis (Thoma et al., Plant Physiol. 105:35-45 (1994)), Norway spruce (Sabala et al., Plant Mol. Biol. 42:461-478 (2000)), rice (Vignols et al., Gene 142:265-270 (1994)), carrot (Toonen et al., Plant J. 12:1213-1221 (1997)), Brassica napus (Sohal et al., Plant Mol. Biol. 41:75-87 (1999)), Sorghum vulgare (Pelese-Siebenbourg et al., Gene 148:305-308 (1994)), and other plant species. The reported LTP genes are known to have various expression patterns in respective plants. However, there remains a lack of soybean LTP genes or flower-preferred expression of LTP genes. LTP assays have been described (Jean-Claude Kader, Annual Review of Plant Phys. and Plant Mol. Biol. 47: 627-654 (1996). Plant LTPs have eight cysteine residues located at conserved positions. The cysteine residues are engaged in four disulfide bridges (Jean-Claude Kader, Annual Review of Plant Phys. and Plant Mol. Biol. 47: 627-654 (1996)).

Although advances in technology provide greater success in transforming plants with chimeric genes, there is still a need for preferred expression of such genes in desired plants. Often times it is desired to selectively express target genes in a specific tissue because of toxicity or efficacy concerns. For example, flower tissue is a type of tissue where preferred expression is desirable and there remains a need for promoters that preferably initiate transcription in flower tissue. Promoters that initiate transcription preferably in flower tissue control genes involved in flower development and flower abortion.

SUMMARY OF THE INVENTION

Compositions and methods for regulating gene expression in a plant are provided. One aspect is for an isolated polynucleotide comprising: a) a nucleotide sequence comprising the sequence set forth in SEQ ID NO:1 or a full-length complement thereof; or b) a nucleotide sequence comprising a sequence having at least 90% sequence identity, based on the BLASTN method of alignment, when compared to the sequence set forth in SEQ ID NO: 1; wherein said nucleotide sequence is a promoter. Another aspect is for an isolated polynucleotide comprising (a) a nucleotide sequence comprising a fragment of SEQ ID NO:1, SEQ ID NO:2, SEQ ID NO:3, SEQ ID NO:4, SEQ ID NO:5, or SEQ ID NO:6, or a full-length complement thereof; or (b) a nucleotide sequence comprising a sequence having at least 90% sequence identity, based on the BLASTN method of alignment, when compared to the nucleotide sequence of (a); wherein said nucleotide sequence is a promoter.

Other embodiments include recombinant DNA constructs comprising a polynucleotide sequence of the present invention operably linked to a heterologous sequence. Additional, some embodiments provide for transgenic plant cells, transient and stable, transgenic plant seeds, as well as transgenic plants comprising the provided recombinant DNA constructs.

There are provided some embodiments that include methods of expressing a coding sequence or a functional RNA in a flowering plant comprising: introducing a recombinant DNA construct described above into the plant, wherein the heterologous sequence comprises a coding sequence; growing the plant; and selecting a plant displaying expression of the coding sequence or the functional RNA of the recombinant DNA construct.

Furthermore, some embodiments of the present invention include methods of transgenically altering a marketable flower trait of a flowering plant, comprising: introducing a recombinant DNA construct described above into the flowering plant; growing a fertile, mature flowering plant resulting from the introducing step; and selecting a flowering plant expressing the heterologous nucleotide sequence in flower tissue based on the altered marketable flower trait.

Another aspect is for an isolated polynucleotide comprising: (a) a nucleotide sequence encoding a polypeptide, wherein the polypeptide has at least 90% sequence identity, based on the Clustal method of alignment, when compared to the sequence set forth in SEQ ID NO:18, or (b) a full-length complement of the nucleotide sequence of (a).

A further aspect is for an isolated polypeptide, wherein the isolated polypeptide has at least 90% sequence identity, based on the Clustal method of alignment, when compared to the sequence set forth in SEQ ID NO:18.

BRIEF DESCRIPTION OF THE DRAWINGS AND SEQUENCES

The patent or application file contains at least one drawing executed in color. Copies of this patent or application publication with color drawing(s) will be provided by the Office upon request and payment of necessary fee.

The invention can be more fully understood from the following detailed description, the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

SEQ ID NO:1 is a DNA sequence comprising a 1771 nucleotide soybean LTP2 promoter (or full-length LTP2 promoter).

SEQ ID NO:2 is a 1384 basepair truncated form of the LTP2 promoter shown in SEQ ID NO:1 (bp 388-1771 of SEQ ID NO:1).

SEQ ID NO:3 is a 988 basepair truncated form of the LTP2 promoter shown in SEQ ID NO:1 (bp 784-1771 of SEQ ID NO:1).

SEQ ID NO:4 is a 682 basepair truncated form of the LTP2 promoter shown in SEQ ID NO:1 (bp 1090-1771 of SEQ ID NO:1).

SEQ ID NO:5 is a 393 basepair truncated form of the LTP2 promoter shown in SEQ ID NO:1 (bp 1379-1771 of SEQ ID NO:1).

SEQ ID NO:6 is a 224 basepair truncated form of the LTP2 promoter shown in SEQ ID NO:1 (bp 1548-1771 of SEQ ID NO:1).

SEQ ID NO:7 is an oligonucleotide primer used in the PCR amplifications of the truncated LTP2 promoter in SEQ ID NO:2 when paired with SEQ ID NO:8, and the truncated LTP2 promoters in SEQ ID NOs: 3, 4, 5, or 6 when paired with SEQ ID NOs: 9, 10, 11, or 12, respectively.

SEQ ID NO:8 is an oligonucleotide primer used in the PCR amplification of the truncated LTP2 promoter in SEQ ID NO:2 when paired with SEQ ID NO:7.

SEQ ID NO:9 is an oligonucleotide primer used in the PCR amplification of the truncated LTP2 promoter in SEQ ID NO:3 when paired with SEQ ID NO:7.

SEQ ID NO:10 is an oligonucleotide primer used in the PCR amplification of the truncated LTP2 promoter in SEQ ID NO:4 when paired with SEQ ID NO:7.

SEQ ID NO:11 is an oligonucleotide primer used in the PCR amplification of the truncated LTP2 promoter in SEQ ID NO:5 when paired with SEQ ID NO:7.

SEQ ID NO:12 is an oligonucleotide primer used in the PCR amplification of the truncated LTP2 promoter in SEQ ID NO:6 when paired with SEQ ID NO:7.

SEQ ID NO:13 is an oligonucleotide primer specific to the soybean PSO400258 gene used in the first nested PCR amplification of the LTP2 promoter when paired with SEQ ID NO:14.

SEQ ID NO:14 is an oligonucleotide primer used in the first nested PCR amplification of the LTP2 promoter when paired with SEQ ID NO:13.

SEQ ID NO:15 is an oligonucleotide primer specific to the soybean PSO400258 gene used in the second nested PCR amplification of the LTP2 promoter when paired with SEQ ID NO:16. An NcoI restriction site CCATGG is added for subsequent cloning.

SEQ ID NO:16 is an oligonucleotide primer used in the second nested PCR amplification of the LTP2 promoter when paired with SEQ ID NO:15.

SEQ ID NO:17 is the nucleotide sequence of a novel soybean cDNA PSO400258 encoding a polypeptide with similarity to lipid transfer proteins. Nucleotides 1 to 46 are the 5' untranslated sequence, nucleotides 47 to 49 are the translation initiation codon, nucleotides 47 to 418 are polypeptide coding region, nucleotides 419 to 421 are the termination codon, nucleotides 419 to 597 are the 3' untranslated sequence, nucleotides 598 to 629 are part of the poly (A) tail.

SEQ ID NO:18 is the 124 amino acid long putative PSO400258 translation product LTP2 protein sequence.

SEQ ID NO:19 is an oligonucleotide primer used in the diagnostic PCR to check for soybean genomic DNA presence in total RNA or cDNA when paired with SEQ ID NO:20.

SEQ ID NO:20 is an oligonucleotide primer used in the diagnostic PCR to check for soybean genomic DNA presence in total RNA or cDNA when paired with SEQ ID NO:19.

SEQ ID NO:21 is the longer strand sequence of the adaptor supplied in ClonTech™ GenomeWalker™ kit.

SEQ ID NO:22 is an MPSS tag sequence that is specific to the unique gene PSO400258.

SEQ ID NO:23 is a sense primer used in quantitative RT-PCR analysis of PSO400258 gene expression profile.

SEQ ID NO:24 is an antisense primer used in quantitative RT-PCR analysis of PSO400258 gene expression profile.

SEQ ID NO:25 is a sense primer used as an endogenous control gene-specific primer in the quantitative RT-PCR analysis of PSO400258 gene expression profile.

SEQ ID NO:26 is an antisense primer used as an endogenous control gene-specific primer in the quantitative RT-PCR analysis of PSO400258 gene expression profile.

SEQ ID NO:27 is a sense primer used in quantitative PCR analysis of SAMS:ALS transgene copy numbers.

SEQ ID NO:28 is a FAM labeled fluorescent DNA oligo probe used in quantitative PCR analysis of SAMS:ALS transgene copy numbers.

SEQ ID NO:29 is an antisense primer used in quantitative PCR analysis of SAMS:ALS transgene copy numbers.

SEQ ID NO:30 is a sense primer used in quantitative PCR analysis of GM-LTP2:YFP transgene copy numbers.

SEQ ID NO:31 is a FAM labeled fluorescent DNA oligo probe used in quantitative PCR analysis of GM-LTP2:YFP transgene copy numbers.

SEQ ID NO:32 is an antisense primer used in quantitative PCR analysis of GM-LTP2:YFP transgene copy numbers.

SEQ ID NO:33 is a sense primer used as an endogenous control gene primer in quantitative PCR analysis of transgene copy numbers.

SEQ ID NO:34 is a VIC labeled fluorescent DNA oligo probe used as an endogenous control gene probe in quantitative PCR analysis of transgene copy numbers.

SEQ ID NO:35 is an antisense primer used as an endogenous control gene primer in quantitative PCR analysis of transgene copy numbers.

SEQ ID NO:36 is the recombination site attB1 sequence in the Gateway cloning system (Invitrogen).

SEQ ID NO:37 is the recombination site attB2 sequence in the Gateway cloning system (Invitrogen).

SEQ ID NO:38 is the 3291 bp sequence of QC299.

SEQ ID NO:39 is the 5055 bp sequence of QC301.

SEQ ID NO:40 is the 8187 bp sequence of PHP25224.

SEQ ID NO:41 is the 9358 bp sequence of QC303.

SEQ ID NO:42 is the 2817 bp sequence of pCR8/GW/TOPO.

SEQ ID NO:43 is the 4201 bp sequence of QC301-1.

SEQ ID NO:44 is the 5286 bp sequence of QC330.

SEQ ID NO:45 is the 5042 bp sequence of QC301-1Y.

SEQ ID NO:46 is the 4646 bp sequence of QC301-2Y.

SEQ ID NO:47 is the 4340 bp sequence of QC301-3Y.

SEQ ID NO:48 is the 4051 bp sequence of QC3014Y.

SEQ ID NO:49 is the 3882 bp sequence of QC301-5Y.

SEQ ID NO:50 is the 4157 bp sequence of pZSL90.

Table 1 displays the relative abundance (parts per million, PPM) of the PSO400258 gene determined by Lynx MPSS gene expression profiling.

FIG. 1 displays the logarithm of relative quantifications of the PSO400258 gene expression in 14 different soybean tissues by quantitative RT-PCR. The gene expression profile indicates that the PSO400258 gene is highly expressed in flower buds and open flowers.

Figure 2:
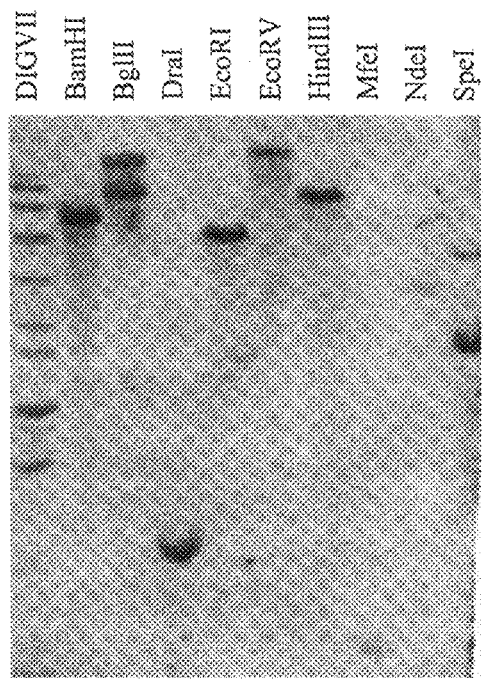
Figure 2:
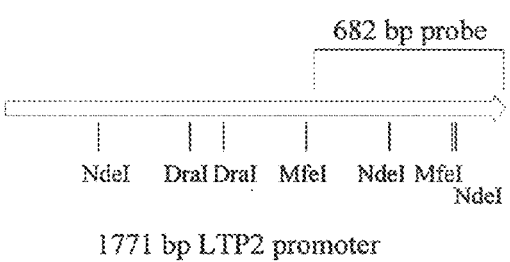

FIG. 2 displays the LTP2 promoter copy number analysis by Southern hybridization. Also displayed is a schematic of the LTP2 promoter showing relative linear positions of a number of restriction sites.

Figure 3:
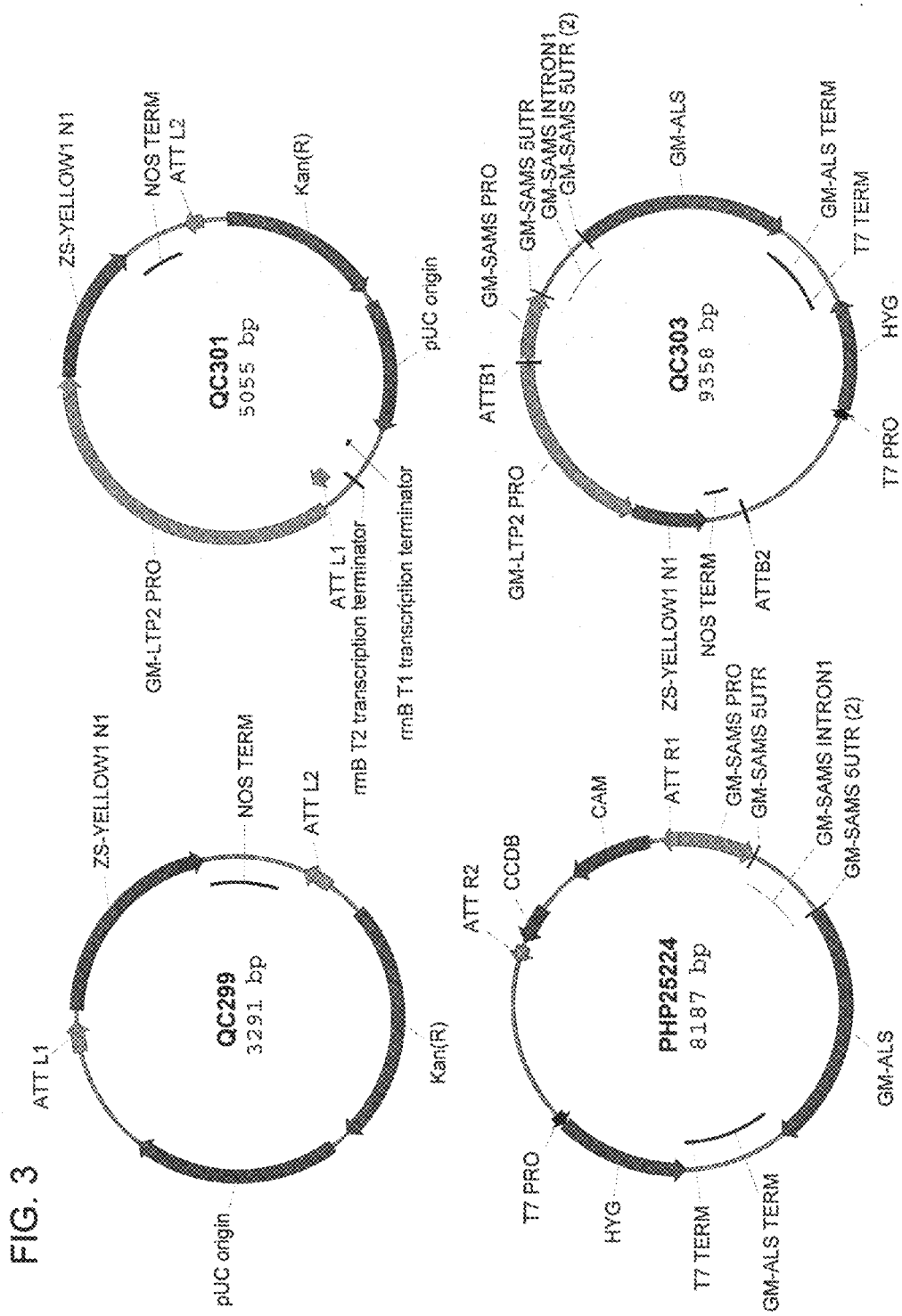

FIG. 3 is a schematic representation of the map of plasmid QC299, QC301, PHP25224, and QC303.

Figure 4:
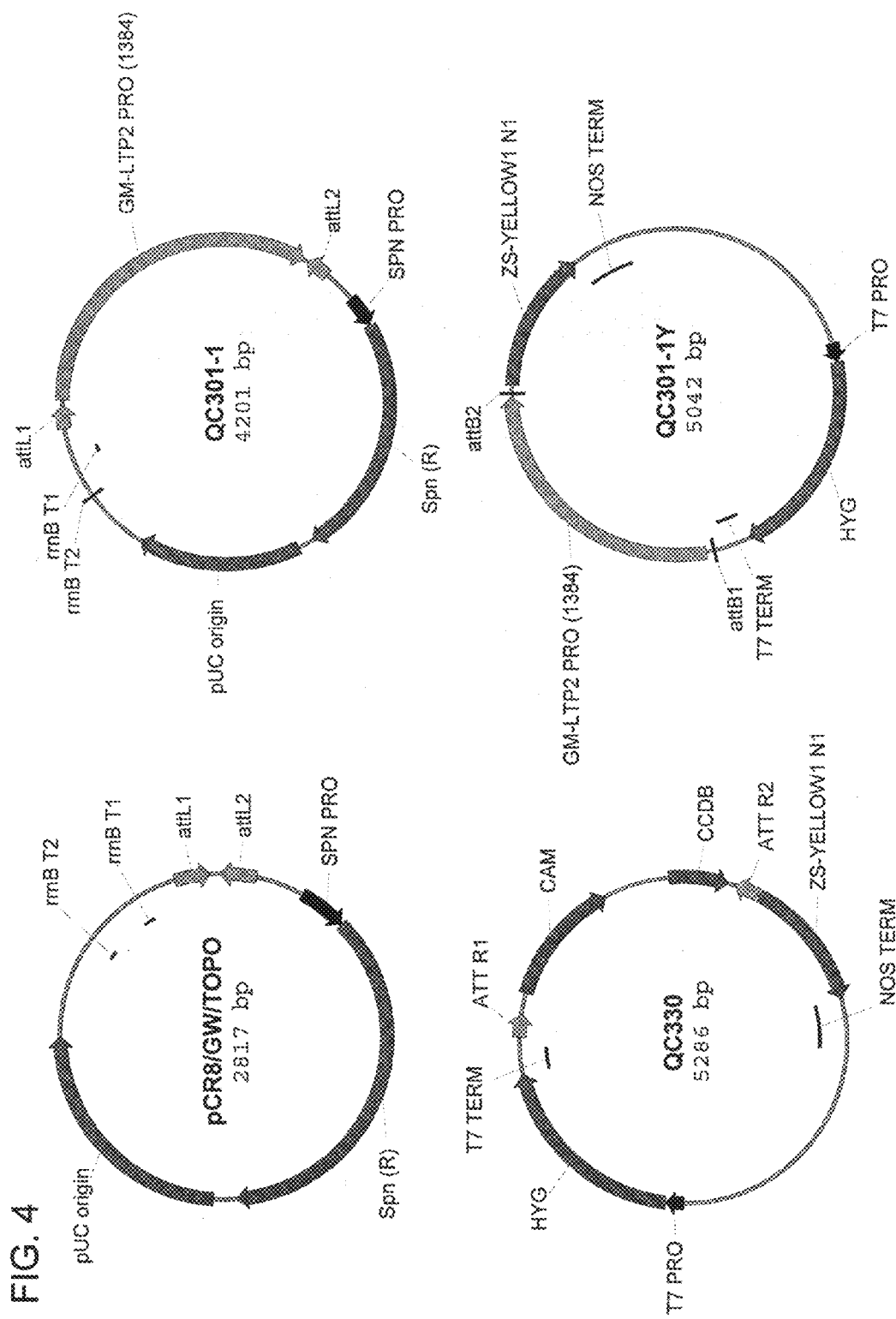

FIG. 4 displays schematic representations of a Gateway cloning entry vector pCR8/GW/TOPO. (Invitrogen), the construct QC301-1 created by cloning the full length LTP2 promoter into pCR8/GW/TOPO, a Gateway cloning destination vector QC330 containing a reporter ZS-YELLOW1 N1, and a final construct QC301-1Y with the 1384 bp truncated LTP2 promoter (SEQ ID NO:2) placed in front of the ZS-YELLOW1 N1 reporter gene. Promoter deletion constructs QC301-2Y, QC301-3Y, QC301Y, and QC301-5Y containing the 988, 682, 393, and 224 bp truncated LTP2 promoters, respectively, have similar map configurations, the difference being in the length of the promoter.

Figure 5:
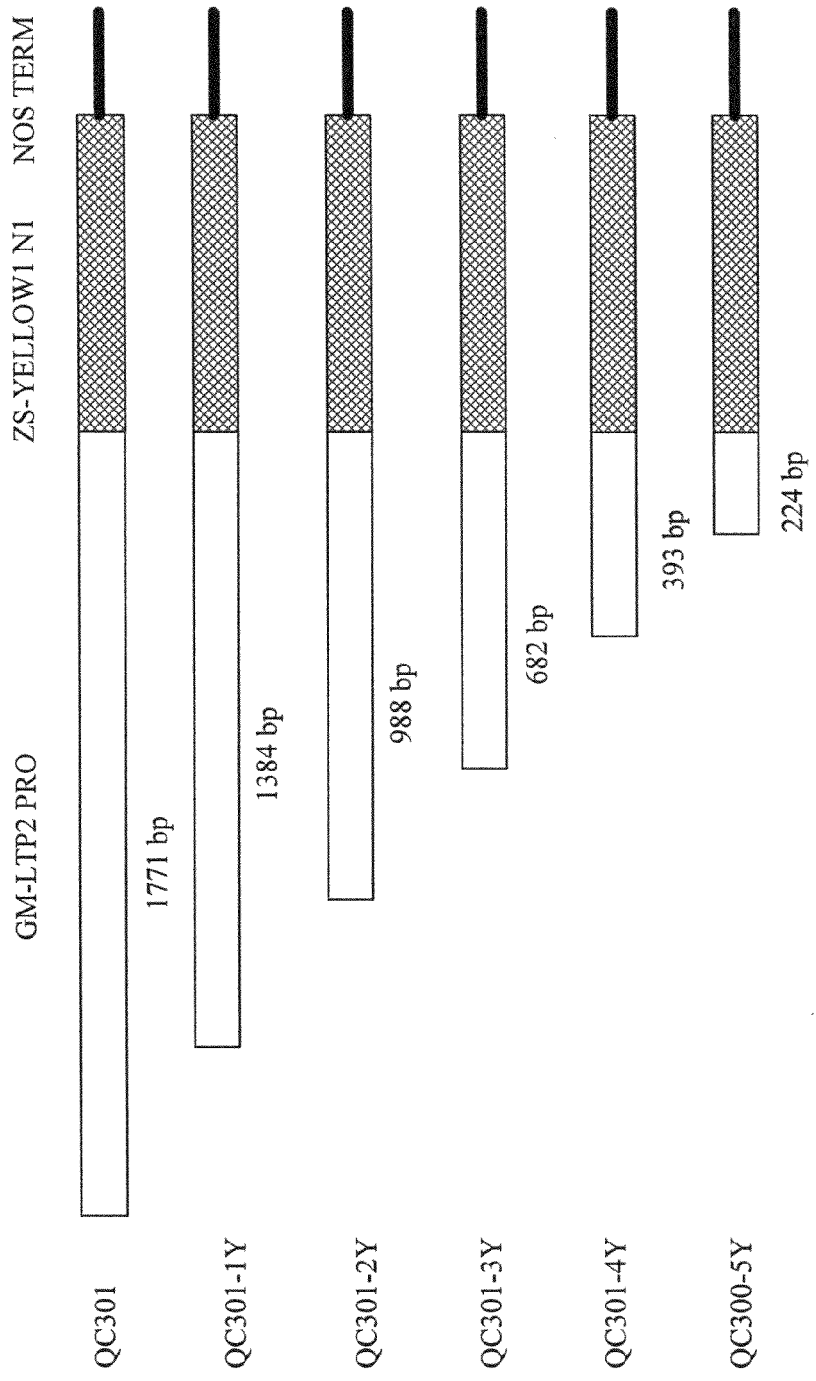

FIG. 5 is a linear schematic of the LTP2 promoter constructs QC301, QC301-1Y, QC301-2Y, QC301-3Y, QC3014Y, and QC301-5Y wherein the reporter ZS-YELLOW1 N1 is operably linked to the full length LTP2 promoter and the progressive truncations of the LTP2 promoter.

Figure 6:
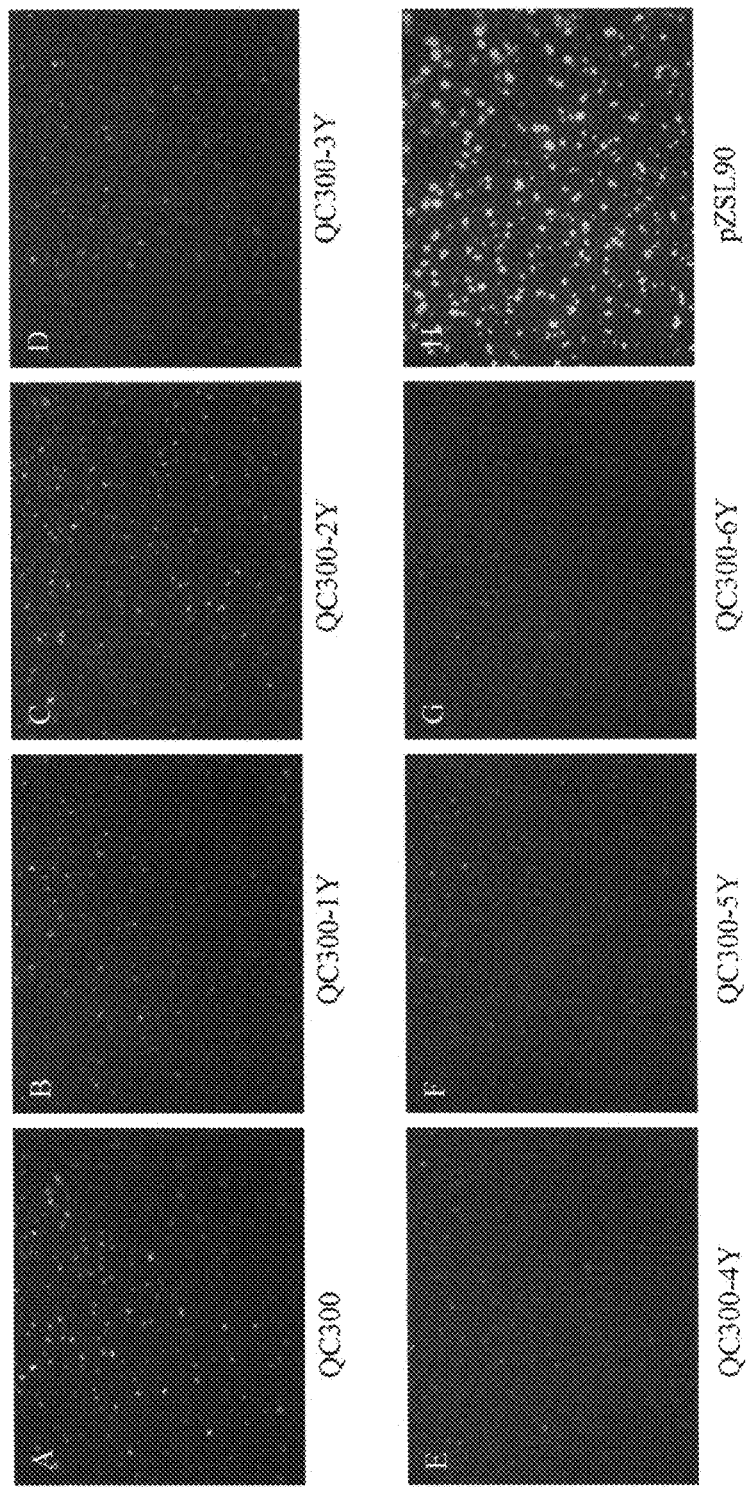

FIG. 6 displays the transient expression of the fluorescent protein reporter gene ZS-YELLOW1 N1 in the cotyledons of germinating soybean seeds. The reporter gene is driven by the full length LTP2 promoter in construct QC301, or driven by the LTP2 promoter or the progressively truncated LTP2 promoters in the transient expression constructs QC301-1Y to QC301-5Y. Construct pZSL90 represents the positive control (constitutive promoter SCP1 drives the same reporter gene).

Figure 7:
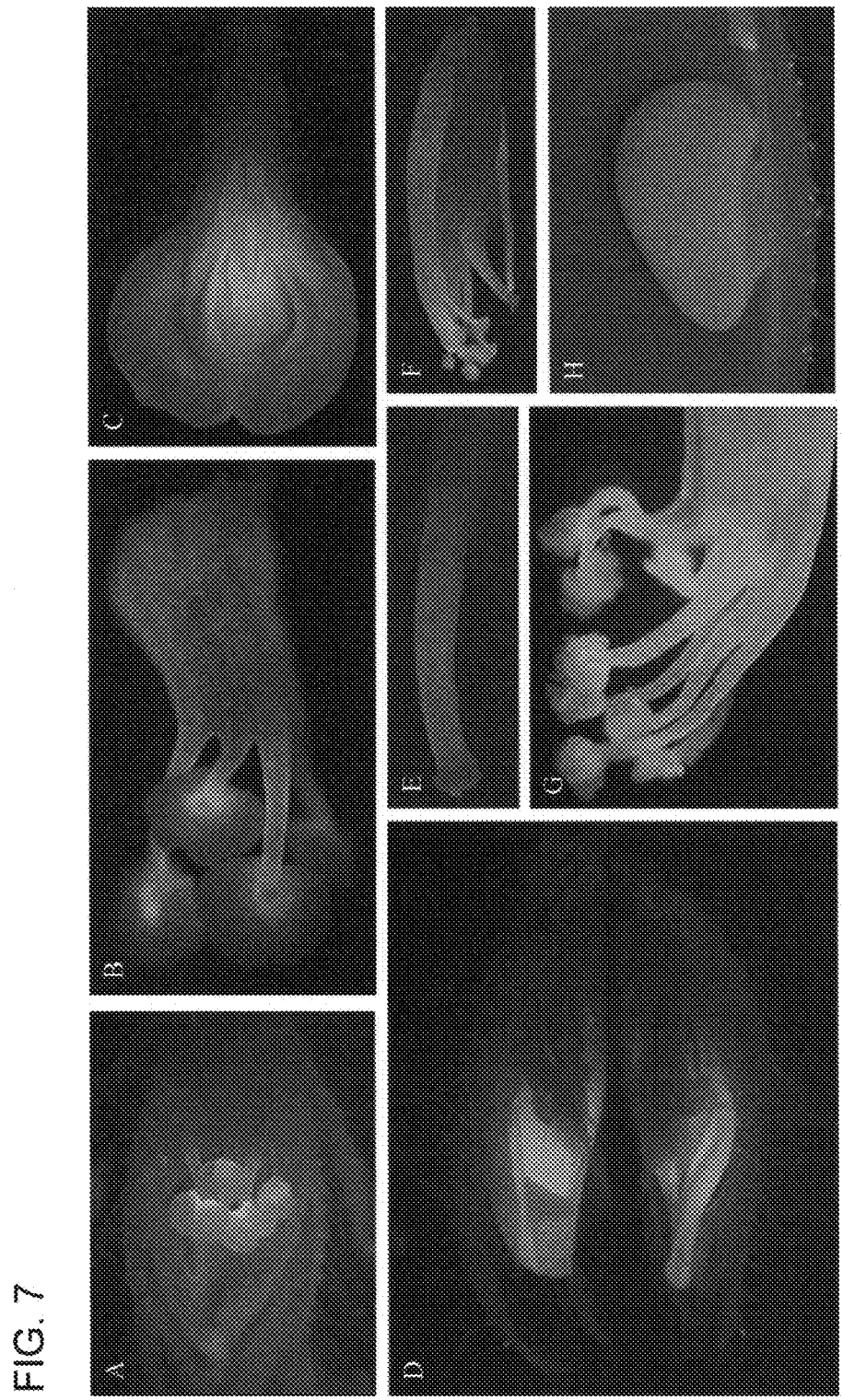

FIG. 7 displays the stable expression of the fluorescent protein reporter gene ZS-YELLOW1 N1 in the floral and other tissues of transgenic soybean plants containing a single copy of the transgene construct QC303. The green color indicates ZS-YELLOW1 N1 gene expression. The red color is background auto fluorescence from plant green tissues.

DETAILED DESCRIPTION OF THE INVENTION

The disclosure of all patents, patent applications, and publications cited herein are incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure, a number of terms shall be utilized.

The term "promoter" refers to a nucleotide sequence capable of controlling the expression of a coding sequence or functional RNA. Functional RNA includes, but is not limited to, transfer RNA (tRNA) and ribosomal RNA (rRNA). Numerous examples of promoters may be found in the compilation by Okamuro and Goldberg (Biochemistry of Plants 15:1-82 (1989)). The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that, since in most cases the exact boundaries of regulatory sequences have not been completely defined, DNA fragments of some variation may have identical promoter activity.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene, and is not necessarily a part of the sequence that encodes the final gene product.

A "flower" is a complex structure consisting of pedicel, sepal, petal, stamen, and carpel. A stamen comprises an anther, pollen and filament. A carpel comprises a stigma, style and ovary. An ovary comprises an ovule, embryo sac, and egg cell. Soybean pods develop from the pistil. It is likely that a gene expressed in the pistil of a flower continues to express in early pod. A "flower cell" is a cell from any one of these structures. Flower promoters in general include promoters that direct gene expression in any of the above tissues or cell types.

The term "flower crop" or "flowering plants" are plants that produce flowers that are marketable within the floriculture industry. Flower crops include both cut flowers and potted flowering plants. Cut flowers are plants that generate flowers that can be cut from the plant and can be used in fresh flower arrangements. Flower crops include roses, carnations, Gerberas, Chrysanthemums, tulips, Gladiolis, Alstroemerias, Anthuriums, lisianthuses, larkspurs, irises, orchids, snapdragons, African violets, azaleas, in addition to other less popular flower crops.

The terms "flower-specific promoter" or "flower-preferred promoter" may be used interchangeably herein and refer to promoters active in flower, with promoter activity being significantly higher in flower tissue versus non-flower tissue. "Preferentially initiates transcription", when describing a particular cell type, refers to the relative level of transcription in that particular cell type as opposed to other cell types. The described LTP2 promoters are promoters that preferentially initiate transcription in flower cells. Preferably, the promoter activity in terms of expression levels of an operably linked sequence is more than ten-fold higher in flower tissue than non-flower tissue. More preferably, the promoter activity is present in flower tissue while undetectable in non-flower tissue.

As used herein, an "LTP2 promoter" refers to one type of flower-specific promoter. The native LTP2 promoter (or full-length native LTP2 promoter) is the native promoter of the putative soybean LTP2 polypeptide, which is a novel protein without significant homology to any known protein in public databases. The "LTP2 promoter", as used herein, also refers to fragments of the full-length native promoter that retain significant promoter activity. For example, an LTP2 promoter of the present invention can be the full-length promoter (SEQ ID NO:1) or a promoter-functioning fragment thereof, which includes, among others, the polynucleotides of SEQ ID NOs: 2, 3, 4, 5, and 6. An LTP2 promoter also includes variants that are substantially similar and functionally equivalent to any portion of the nucleotide sequence set forth in SEQ ID NOs: 1, 2, 3, 4, 5, or 6, or sequences therebetween.

An "isolated nucleic acid fragment" or "isolated polynucleotide" refers to a polymer of ribonucleotides (RNA) or deoxyribonucleotides (DNA) that is single-stranded or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "heterologous nucleic acid fragment" or "heterologous nucleotide sequence" refers to a nucleotide sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed.

The terms "fragment (or variant) that is functionally equivalent" and "functionally equivalent fragment (or variant)" are used interchangeably herein. These terms refer to a portion or subsequence or variant of the promoter sequence of the present invention in which the ability to initiate transcription or drive gene expression (such as to produce a certain phenotype) is retained. Fragments and variants can be obtained via methods such as site-directed mutagenesis and synthetic construction. As with the provided promoter sequences described herein, the contemplated fragments and variants operate to promote the flower-preferred expression of an operably linked heterologous nucleic acid sequence, forming a recombinant DNA construct (also, a chimeric gene). For example, the fragment or variant can be used in the design of recombinant DNA constructs to produce the desired phenotype in a transformed plant. Recombinant DNA constructs can be designed for use in co-suppression or antisense by linking a promoter fragment or variant thereof in the appropriate orientation relative to a heterologous nucleotide sequence.

In some aspects of the present invention, the promoter fragments can comprise at least about 20 contiguous nucleotides, or at least about 50 contiguous nucleotides, or at least about 75 contiguous nucleotides, or at least about 100 contiguous nucleotides of SEQ ID NO:1, SEQ ID NO:2, SEQ ID NO:3, SEQ ID NO:4, SEQ ID NO:5, or SEQ ID NO:6. In another aspect, a promoter fragment is the nucleotide sequence set forth in SEQ ID NO:2, SEQ ID NO:3, SEQ ID NO:4, SEQ ID NO:5, or SEQ ID NO:6. The nucleotides of such fragments will usually comprise the TATA recognition sequence of the particular promoter sequence. Such fragments may be obtained by use of restriction enzymes to cleave the naturally occurring promoter nucleotide sequences disclosed herein, by synthesizing a nucleotide sequence from the naturally occurring promoter DNA sequence, or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989.

The terms "substantially similar" and "corresponding substantially" as used herein refer to nucleic acid sequences, particularly promoter sequences, wherein changes in one or more nucleotide bases do not substantially alter the ability of the promoter to initiate transcription or drive gene expression or produce a certain phenotype. These terms also refer to modifications, including deletions and variants, of the nucleic acid sequences of the instant invention by way of deletion or insertion of one or more nucleotides that do not substantially alter the functional properties of the resulting promoter relative to the initial, unmodified promoter. It is therefore understood, as those skilled in the art will appreciate, that the invention encompasses more than the specific exemplary sequences.

In one example of substantially similar, substantially similar nucleic acid sequences include those that are also defined by their ability to hybridize to the disclosed nucleic acid sequences, or portions thereof. Substantially similar nucleic acid sequences include those sequences that hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2× SSC, 0.5% SDS is increased to 60° C. Another set of highly stringent conditions uses two final washes in 0.1×SSC, 0.1% SDS at 65° C.

In some examples, substantially similar nucleic acid sequences are those sequences that are at least 80% identical to the nucleic acid sequences reported herein or which are at least 80% identical to any portion of the nucleotide sequences reported herein. In some instances, substantially similar nucleic acid sequences are those that are at least 90% identical to the nucleic acid sequences reported herein, or at least 90% identical to any portion of the nucleotide sequences reported herein. In some examples, substantially similar nucleic acid sequences are those that are at least 95% identical to the nucleic acid sequences reported herein, or are at least 95% identical to any portion of the nucleotide sequences reported herein. It is well understood by one skilled in the art that many levels of sequence identity are useful in identifying related polynucleotide sequences. Useful examples of percent identities are those listed above, or also any integer percentage from 80% to 100%, such as, for example, 81%, 82%, 83%, 84%, 85%, 86%, 87%, 88%, 89%, 90%, 91%, 92%, 93%, 94%, 95%, 96%, 97%, 98% and 99%.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid sequence for improved expression in a host cell, it is desirable to design the nucleic acid sequence such that its frequency of codon usage approaches the frequency of preferred codon usage of the host cell.

Sequence alignments and percent similarity calculations may be determined using the Megalign program of the LASARGENE bioinformatics computing suite (DNASTAR Inc., Madison, Wis.). Multiple alignment of the sequences are performed using the Clustal method of alignment (Higgins and Sharp, CABIOS 5:151-153 (1989)) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN refers to a BLAST program that compares a nucleotide query sequence against a nucleotide sequence database.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, and arranged in a manner different than that found in nature. "Endogenous gene" refers to a native gene in its natural location in the genome of an organism. A "foreign" gene refers to a gene not normally found in the host organism, which is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that encodes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, and are not limited to, promoters, enhancers, translation leader sequences, introns, and polyadenylation recognition sequences.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized as affecting the addition of polyadenylic acid tracts to the 3' end of the mRNA precursor. The use of different 3' non-coding sequences is exemplified by Ingelbrecht et al., Plant Cell 1:671-680 (1989).

"RNA transcript" refers to a product resulting from RNA polymerase-catalyzed transcription of a DNA sequence. When an RNA transcript is a perfect complementary copy of a DNA sequence, it is referred to as a primary transcript, or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene. The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated yet has an effect on cellular processes.

The term "operably linked" refers to the association of nucleic acid sequences on a single polynucleotide so that the function of one is affected by the other. For example, a promoter is operably linked with a heterologous nucleotide sequence, e.g., a coding sequence, when it is capable of affecting the expression of that heterologous nucleotide sequence (i.e., for example, the coding sequence is under the transcriptional control of the promoter). A coding sequence can be operably linked to promoter sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, refers to the production of a functional end-product, e.g., an mRNA or a protein (precursor or mature).

The term "recombinant DNA construct" or "recombinant expression construct" is used interchangeably and refers to a discrete polynucleotide into which a nucleic acid sequence or fragment can be moved. Preferably, it is a plasmid vector or a fragment thereof comprising the promoters of the present invention. The choice of plasmid vector is dependent upon the method that will be used to transform host plants. The skilled artisan is well aware of the genetic elements that must be present on the plasmid vector in order to successfully transform, select and propagate host cells containing the recombinant DNA construct. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at post-transcriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al., Plant J. 16:651-659 (1998); and Gura, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication Nos. WO99/53050 and WO02/00904). This increases the frequency of co-suppression in the recovered transgenic plants. Another variation describes the use of plant viral sequences to direct the suppression, or "silencing", of proximal mRNA encoding sequences (PCT Publication No. WO98/36083). Neither of these co-suppressing phenomena has been elucidated mechanistically at the molecular level, although genetic evidence has been obtained that may lead to the identification of potential components (Elmayan et al., Plant Cell 10:1747-1757 (1998)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" refers to the transfer of a nucleic acid fragment into the genome of a host organism, resulting in genetically stable inheritance. Host organisms containing the transformed nucleic acid fragments are referred to as "transgenic" organisms. Thus, a "transgenic plant cell" as used herein refers to a plant cell containing the transformed nucleic acid fragments. The preferred method of soybean cell transformation is use of particle-accelerated or "gene gun" transformation technology (Klein, T., Nature (London) 327:70-73 (1987); U.S. Pat. No. 4,945,050).

"Transient expression" refers to the temporary expression of often reporter genes such as β-glucuronidase (GUS), fluorescent protein genes GFP, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

A "marketable flower trait" is a characteristic or phenotype of the flower of a plant such as the color, scent or morphology of a flower. The marketable flower trait is a characteristic of a flower that is of high regard to a flower crop consumer in deciding whether to purchase the flower crop.

The phrase "genes involved in anthocyanin biosynthesis" refers to genes that encode proteins that play a role in converting metabolic precursors into the one of a number of anthocyanins. Examples of genes involved in the biosynthesis of anthocyanin are dyhydroflavonol 4-reductase, flavonoid 3,5-hydroxylase, chalcone synthase, chalcone isomerase, flavonoid 3-hydroxylase, anthocyanin synthase, and UDP-glucose 3-O-flavonoid glucosyl transferase (see, e.g., Mori et al., Plant Cell Reports 22:415-421 (2004)).

The phrase "genes involved in the biosynthesis of fragrant fatty acid derivatives" refers to genes that encode proteins that play a role in manipulating the biosynthesis of fragrant fatty acid derivatives such as terpenoids, phenylpropanoids, and benzenoids in flowers (see, e.g., Tanaka et al., Plant Cell, Tissue and Organ Culture 80:1-24 (2005)). Examples of such genes include S-linalool synthase, acetyl CoA:benzylalcohol acetyltransferase, benzyl CoA:benzylalcohol benzoyl transferase, S-adenosyl-L-methionine:benzoic acid carboxyl methyl transferase (BAMT), mycrene synthases, (E)-β-ocimene synthase, orcinol O-methyltransferase, and limonene synthases (see, e.g., Tanaka et al., supra).

The term "flower homeotic genes" or "flower morphology modifying genes" refers to genes that are involved in pathways associated with flower morphology. A modification of flower morphology can lead to a novel form of the respective flower that can enhance its value in the flower crop marketplace. Morphology can include the size, shape, or petal pattern of a flower. Some example of flower homeotic genes include genes involved in cell-fate determination (in ABC combinatorial model of gene expression), including AGAMOUS, which determines carpel fate in the central whorl, APETALA3, which determines the sepal fate in the outer whorl, and PISTILLATA, which determines petal development in the second whorl (Espinosa-Soto et al., *Plant Cell* 16:2923-2939 (2004)).

Standard recombinant DNA and molecular cloning techniques used herein are well known in the art and are described more fully in Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments consisting of a series of repetitive cycles (Perkin Elmer Cetus Instruments, Norwalk, Conn.). Typically, the double stranded DNA is heat denatured; the two primers complementary to the 3' boundaries of the target segment are annealed at low temperature and then extended at an intermediate temperature. One set of these three consecutive steps comprises a cycle.

Embodiments of the present invention include isolated polynucleotides comprising a nucleotide sequence that is a promoter. In some instances the nucleotide sequence includes one or more of the following:
 a) the sequence set forth in SEQ ID NO:1 or a full-length complement thereof; or
 b) a nucleotide sequence comprising a sequence having at least 90% sequence identity, based on the BLASTN method of alignment, when compared to the sequence set forth in SEQ ID NO:1.

In other aspects, the nucleotide sequence includes one or more of the following:
 (a) a nucleotide sequence comprising a fragment of SEQ ID NO:1, SEQ ID NO:2, SEQ ID NO:3, SEQ ID NO:4, SEQ ID NO:5, or SEQ ID NO:6, or a full-length complement thereof; or
 (b) a nucleotide sequence comprising a sequence having at least 90% sequence identity, based on the BLASTN method of alignment, when compared to the nucleotide sequence of (a).

The nucleotide sequences of the present invention can be referred to as a promoter or as having promoter-like activity. In some embodiments the nucleotide sequence is a promoter that preferentially initiates transcription in a plant flower cell. Such promoter is referred to as a flower-specific promoter. Preferably the promoter of the present invention is the soybean "LTP2" promoter.

In a preferred embodiment, the promoter comprises the nucleotide sequence set forth in SEQ ID NO:1, SEQ ID NO:2, SEQ ID NO:3, SEQ ID NO:4, SEQ ID NO:5, or SEQ ID NO:6. The present invention also includes nucleic acid fragments, variants, and complements of the aforementioned nucleotide sequences or promoters, provided that they are substantially similar and functionally equivalent to the nucleotide sequence set forth in these nucleotide sequences. A nucleic acid fragment or variant that is functionally equivalent to the present LTP2 promoter is any nucleic acid fragment or variant that is capable of initiating the expression, preferably initiating flower-specific expression, of a coding sequence or functional RNA in a similar manner to the LTP2 promoter. The expression patterns of LTP2 gene and its promoter are set forth in Examples 1, 2, 7, and 8. In one example, the expression pattern of a LTP2 promoter fragment or variant will have expression patterns similar to that of the LTP2 promoter.

In some aspects, a recombinant DNA construct can be formed in part by operably linking at least one of the promoters of the present invention to any heterologous nucleotide sequence. The heterologous nucleotide sequence can be expressed in a cell as either a functional RNA or a polypeptide. The cell for expression includes a plant or bacterial cell, preferably a plant cell. The recombinant DNA construct preferably includes the LTP2 promoter. The recombinant DNA construct preferably includes a heterologous nucleotide sequence that encodes a protein that plays a role in flower color formation, fragrance production, or shape/morphology development of the flower. The color of a flower can be altered transgenically by expressing genes involved in betalain, carotenoid, or flavanoid biosynthesis. In regard to genes involved in the biosynthesis of anthocyanin, dyhydroflavonol 4-reductase, flavonoid 3,5-hydroxylase, chalcone synthase, chalcone isomerase, flavonoid 3-hydroxylase, anthocyanin synthase, and UDP-glucose 3-O-flavonoid glucosyl transferase are some examples. The scent of a flower can be altered transgenically by expressing genes that manipulate the biosynthesis of fragrant fatty acid derivatives such as terpenoids, phenylpropanoids, and benzenoids in flowers. Some embodiments of the invention include a heterologous nucleotide sequence that is selected from S-linalool synthase, acetyl CoA:benzylalcohol acetyltransferase, benzyl CoA:benzylalcohol benzoyl transferase, S-adenosyl-L-methionine:benzoic acid carboxyl methyl transferase, mycrene synthases, (E)-β-ocimene synthase, orcinol O-methyltransferase, or limonene synthases. Flower structures/morphologies can be altered transgenically by expressing flower homeotic genes to create novel ornamental varieties. Some embodiments of the invention include a heterologous nucleotide sequence that is selected from genes such as, for example, AGAMOUS, APETALA3, and PISTILLATA.

It is recognized that the instant promoters may be used with their native coding sequences to increase or decrease expression in flower tissue. The selection of the heterologous nucleic acid fragment depends upon the desired application or phenotype to be achieved. The various nucleic acid sequences can be manipulated so as to provide for the nucleic acid sequences in the proper orientation.

Plasmid vectors comprising the instant recombinant DNA construct can be constructed. The choice of plasmid vector is dependent upon the method that will be used to transform host cells. The skilled artisan is well aware of the genetic elements that must be present on the plasmid vector in order to successfully transform, select and propagate host cells containing the recombinant DNA construct.

The described polynucleotide embodiments encompass isolated or substantially purified nucleic acid compositions. An "isolated" or "purified" nucleic acid molecule, or biologically active portion thereof, is substantially free of other cellular material or culture medium when produced by recombinant techniques, or substantially free of chemical precursors or other chemicals when chemically synthesized. An "isolated" nucleic acid is essentially free of sequences (preferably protein encoding sequences) that naturally flank the polynucleotide (i.e., sequences located at the 5' and 3' ends of the nucleic acid) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequences that naturally flank the polynucleotide in genomic DNA of the cell from which the polynucleotide is derived.

In another embodiment, the present invention includes host cells comprising either the recombinant DNA constructs or isolated polynucleotides of the present invention. Examples of the host cells of the present invention include, and are not limited to, yeast, bacteria, and plants, including flower crops such as, e.g., rose, carnation, Gerbera, Chrysanthemum, tulip, Gladioli, Alstroemeria, Anthurium, lisianthus, larkspur, irises, orchid, snapdragon, African violet, or azalea. Preferably, the host cells are plant cells, and more preferably, flower crop cells, and more preferably, Gerbera, rose, carnation, Chrysanthemum, or tulip cells.

Methods for transforming dicots, primarily by use of Agrobacterium tumefaciens, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); Brassica (U.S. Pat. No. 5,463,174); peanut (Cheng et al., Plant Cell Rep. 15:653-657 (1996); McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses Agrobacterium rhizogenes (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection (Neuhaus et al., Physiol. Plant. 79:213-217 (1990)), or particle bombardment (McCabe et al., Biotechnology 6:923 (1988); Christou et al., Plant Physiol. 87:671-674 (1988)).

In another embodiment, the present invention includes transgenic plants comprising the recombinant DNA constructs provided herein. The transgenic plants are selected from, for example, one of a number of various flower crops including roses, carnations, Gerberas, Chrysanthemums, tulips, Gladiolis, Alstroemerias, Anthuriums, lisianthuses, larkspurs, irises, orchids, snapdragons, African violets, azaleas, in addition to other less popular flower crops.

In some embodiments of the invention, there are provided transgenic seeds produced by the transgenic plants provided. Such seeds are able to produce another generation of transgenic plants.

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, there are generally available standard resource materials that describe specific conditions and procedures for the construction, manipulation and isolation of macromolecules (e.g., DNA molecules, plasmids, and the like), generation of recombinant DNA fragments and recombinant expression constructs, and the screening and isolating of clones (see, for example, Sambrook et al., 1989; Maliga et al., In Methods in Plant Molecular Biology; Cold Spring Harbor Press, 1995; Birren et al., In Genome Analysis: Detecting Genes, 1; Cold Spring Harbor N.Y., 1998; Birren et al., In Genome Analysis: Analyzing DNA, 2; Cold Spring Harbor: N.Y., 1998; Clark, Ed., In Plant Molecular Biology: A Laboratory Manual; Springer: N.Y., 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by northern analysis of mRNA expression, western analysis of protein expression, or phenotypic analysis. Also of interest are seeds obtained from transformed plants displaying the desired expression profile.

The level of activity of the LTP2 promoter in flowers is in some cases comparable to that of many known strong promoters such as the CaMV 35S promoter (Atanassova et al., Plant Mol. Biol. 37:275-285 (1998); Battraw and Hall, Plant Mol. Biol. 15:527-538 (1990); Holtorf et al., Plant Mol. Biol. 29:637-646 (1995); Jefferson et al., EMBO J. 6:3901-3907 (1987); Wilmink et al., Plant Mol. Biol. 28:949-955 (1995)), the Arabidopsis oleosin promoters (Plant et al., Plant Mol. Biol. 25:193-205 (1994); Li, Texas A&M University Ph.D. dissertation, pp. 107-128 (1997)), the Arabidopsis ubiquitin extension protein promoters (Callis et al., J. Biol. Chem. 265(21):12486-12493 (1990)), a tomato ubiquitin gene promoter (Rollfinke et al., Gene 211:267-276 (1998)), a soybean heat shock protein promoter (Raschke et al., J. Mol. Biol. 199(4):549-557 (1988)), and a maize H3 histone gene promoter (Atanassova et al., Plant Mol. Biol. 37:275-285 (1998)).

In some embodiments, the promoters of the present invention are useful when flower-specific expression of a target heterologous nucleic acid fragment is required. Another useful feature of the promoters is its expression profile having high levels in developing flowers and low levels in young developing seeds (See Example 1). The promoters of the present invention are most active in developing flower buds and open flowers, while still having activity although approximately ten times lower in developing seeds. Thus, the promoters can be used for gene expression or gene silencing in flowers, especially when gene expression or gene silencing is desired predominantly in flowers along with a lower degree in developing seeds.

In some embodiments, the promoters of the present invention are to construct recombinant DNA constructs that can be used to reduce expression of at least one heterologous nucleic acid sequence in a plant cell. To accomplish this, a recombinant DNA construct can be constructed by linking the heterologous nucleic acid sequence to a promoter of the present invention. (See U.S. Pat. No. 5,231,020 and PCT Publications WO99/53050, WO02/00904, and WO98/36083 for methodology to block plant gene expression via cosuppression) Alternatively, recombinant DNA constructs designed to express antisense RNA for a heterologous nucleic acid fragment can be constructed by linking the fragment in reverse orientation to a promoter of the present invention. (See U.S. Pat. No. 5,107,065 for methodology to block plant gene expression via antisense RNA.) Either the cosuppression or antisense chimeric gene can be introduced into plants via transformation. Transformants, wherein expression of the heterologous nucleic acid sequence is decreased or eliminated, are then selected.

There are embodiments of the present invention that include promoters of the present invention being utilized for methods of altering (increasing or decreasing) the expression of at least one heterologous nucleic acid sequence in a plant cell which comprises: transforming a plant cell with a recombinant DNA expression construct described herein; growing fertile mature plants from the transformed plant cell; and selecting plants containing a transformed plant cell wherein the expression of the heterologous nucleotide sequence is altered (increased or decreased).

Transformation and selection can be accomplished using methods well-known to those skilled in the art including, but not limited to, the methods described herein.

There are provided some embodiments that include methods of expressing a coding sequence in a plant that is a flower crop comprising: introducing a recombinant DNA construct disclosed herein into the plant; growing the plant; and selecting a plant displaying expression of the coding sequence; wherein the nucleotide sequence comprises: a nucleotide sequence comprising the sequence set forth in SEQ ID NO:1 or a full-length complement thereof; a nucleotide sequence comprising a fragment of the sequence set forth in SEQ ID NO:1, SEQ ID NO:2, SEQ ID NO:3, SEQ ID NO:4, SEQ ID NO:5, or SEQ ID NO:6, or a full-length complement thereof, or in alternative embodiments, the sequence set forth in SEQ ID NO:2, SEQ ID NO:3, SEQ ID NO:4, SEQ ID NO:5, or SEQ ID NO:6; or a nucleotide sequence comprising a sequence having at least 90% sequence identity, based on the BLASTN method of alignment, when compared to the sequence set forth in SEQ ID NO:1; wherein said nucleotide sequence initiates transcription in a flower cell of the plant.

Furthermore, some embodiments of the present invention include methods of transgenically altering a marketable flower trait of a flowering plant, comprising: introducing a recombinant DNA construct disclosed herein into the flowering plant; growing a fertile, mature flowering plant resulting from the introducing step; and selecting a flowering plant expressing the heterologous nucleotide sequence in flower tissue based on the altered marketable flower trait.

As further described in the Examples below, the promoter activity of the soybean genomic DNA fragment sequence SEQ ID NO:1 upstream of the LTP2 protein coding sequence was assessed by linking the fragment to a yellow fluorescence reporter gene, ZS-YELLOW1 N1 (YFP) (Matz et al., Nat. Biotechnol. 17:969-973 (1999)), transforming the promoter: YFP expression cassette into soybean, and analyzing YFP expression in various cell types of the transgenic plants (see Example 7 and 8). All parts of the transgenic plants were analyzed and YFP expression was predominantly detected in flowers. These results indicated that the nucleic acid fragment contained flower-preferred promoter.

Some embodiments of the present invention provide recombinant DNA constructs comprising at least one isopentenyl transferase nucleic acid sequence operably linked to a provide promoter, preferably a LTP2 promoter. The isopentenyl transferase plays a key step in the biosynthesis of plant cytokinin (Kakimoto, J. Plant Res. 116:233-239 (2003)). Elevated levels of cytokinin in plant cells might help to delay floral senescence and abortion which may present a potential way to improve crop yields (Chang et al., Plant Physiol. 132:2174-2183 (2003); Young et al., Plant J. 38:910-922 (2004)).

Utilities for Flower-Specific Promoters

The color, scent or morphology of a flower represents marketable flower traits, or characteristics/phenotypes of a flower that consumers, particularly floriculturalists, consider when determining which flowers are desirable and will be purchased. Hence, it would be beneficial to be able to alter these characteristics in order to satisfy the desires of consumers. Transgenic technologies can be implemented in order to achieve such results.

The phenotype of a flower can be altered transgenically by expressing genes, preferably in flower tissue, that play a role in color formation, fragrance production, or shape/morphology development of the flower. This type of alteration is particularly useful in the floriculture industry, and particularly useful for flowering plants.

The color of a flower is mainly the result of three types of pigment, flavanoids, carotenoids, and betalains. The flavanoids are the most common of the three and they contribute to colors ranging from yellow to red to blue, with anthocyanins being the major flavanoid. Carotenoids are C-40 tetraterpenoids that contribute to the majority of yellow hues and contribute to orange/red, bronze and brown colors, e.g., that seen in roses and chrysanthemums. Betalains are the least abundant and contribute to various hues of ivory, yellow, orange, red and violet. The color of a flower can be altered transgenically by expressing genes involved in, e.g., betalain, carotenoid, or flavanoid biosynthesis. In one example, the color of a flower can be altered transgenically by expressing genes involved in the biosynthesis of anthocyanin, for example, dyhydroflavonol 4-reductase, flavonoid 3,5-hydroxylase, chalcone synthase, chalcone isomerase, flavonoid 3-hydroxylase, anthocyanin synthase, and UDP-glucose 3-O-flavonoid glucosyl transferase. In some aspects of the invention, the gene involved in anthocyanin biosynthesis is the flavonoid 3,5-hydroxylase gene (see, e.g., Mori et al., Plant Cell Reports 22:415-421 (2004)). This type of alteration is particularly useful in the floriculture industry, providing novel flower colors in flower crops.

In addition to color, the scent of a flower can be altered transgenically by expressing genes that manipulate the biosynthesis of fragrant fatty acid derivatives such as terpenoids, phenylpropanoids, and benzenoids in flowers (see, e.g., Tanaka et al., Plant Cell, Tissue and Organ Culture 80:1-24 (2005)). Genes involved in the biosynthesis of fragrant fatty acid derivatives can be operably linked to the flower-specific promoters presently described for preferential expression in flower tissue. The preferential expression in flower tissue can be utilized to generate new and desirable fragrances to enhance the demand for the underlying cut flower. A number of known genes that are involved in the biosynthesis of floral scents are described below. A strong sweet scent can be generated in a flower by introducing or up-regulating expression of S-linalool synthase, which was earlier isolated from Clarkia breweri. Two genes that are responsible for the production of benzylacetate and benzylbenzoate are acetyl CoA:benzylalcohol acetyltransferase and benzyl CoA:benzylalcohol benzoyl transferase, respectively. These transferases were also reported to have been isolated from *C. breweri*. A phenylpropanoid floral scent, methylbenzoate, is synthesized in part by S-adenosyl-L-methionine:benzoic acid carboxyl methyl transferase (BAMT), which catalyzes the final step in the biosynthesis of methyl benzoate. BAMT is known to have a significant role in the emission of methyl benzoate in snapdragon flowers. Two monoterpenes, mycrene and (E)-β-ocimene, from snapdragon are known to be synthesized in part by the terpene synthases: mycrene synthases and (E)-β-ocimene synthases. Other genes involved in biosynthesis of floral scents have been reported and are being newly discovered, many of which are isolated from rose. Some genes involved in scent production in the rose include orcinol O-methyltransferase, for synthesis of S-adenosylmethionine, and limonene synthases (see, e.g., Tanaka et al., supra).

Flower structures/morphologies can be altered transgenically by expressing flower homeotic genes to create novel ornamental varieties. The flower homeotic genes that are determinative of flower morphology include genes such as AGAMOUS, APETALA3, PISTILLATA, and others that are known and/or are being elucidated (see, e.g., Espinosa-Soto et al., Plant Cell 16:2923-2939 (2004)).

EXAMPLES

Aspects of the present invention are exemplified in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

In the discussion below, parts and percentages are by weight and degrees are Celsius, unless otherwise stated. Sequences of promoters, cDNA, adaptors, and primers-listed herein are in the 5' to 3' orientation unless described otherwise. Techniques in molecular biology were typically performed as described in Ausubel et al., 1990 or Sambrook et al., 1989.

Example 1

Lynx MPSS Profiling of Soybean Genes Preferably Expressed in Flowers

Soybean expression sequence tags (ESTs) were generated by sequencing randomly selected clones from cDNA libraries constructed from different soybean tissues. Multiple EST sequences may have different lengths representing different regions of the same soybean gene. For those EST sequences representing the same gene that are found more frequently in a flower-specific cDNA library, there is a possibility that the representative gene could be a flower preferred gene candidate. Multiple EST sequences representing the same soybean gene were compiled electronically based on their overlapping sequence homology into a full length sequence representing a unique gene. These assembled, unique gene sequences were cumulatively collected and the information was stored in a searchable database. Flower specific candidate genes were identified by searching this database to find gene sequences that are frequently found in flower libraries but are rarely found in other tissue libraries, or not found in other tissue libraries.

One unique gene, PSO400258, was identified in the search as a flower specific gene candidate since all of the ESTs representing PSO400258 were mostly found in flower tissue. PSO400258 cDNA sequence (SEQ ID NO:17) as well as its putative translated protein sequence (SEQ ID NO:18) were used to search National Center for Biotechnology Information (NCBI) databases. PSO400258 was found to represent a novel soybean gene with significant homology to lipid transfer protein genes identified in different species (e.g., over 50% identity to lipid transfer proteins from, e.g., *Gossypium hirsutum* (common cotton), *Davidia involucrata* (dove tree), *Platanus x acerifolia* (Liberty London planetree), *Hevea brasiliensis* (rubber tree), *Citrus sinensis* (peach), *Rubus idaeus*

(raspberry), *Lens culinaris* (lentil), *Vitus vinifera* (European grapevine)). PSO400258 was subsequently named as LTP2 to reflect this sequence homology.

A more sensitive gene expression profiling methodology MPSS (Mass Parallel Signature Sequence) transcript profiling technique (Brenner et al., Proc Natl Acad Sci USA 97:1665-70 (2000)) was used to confirm PSO400258 as a flower specific gene. The MPSS technology involves the generation of 17 base signature tags from mRNA samples that have been reverse transcribed from poly A+ RNA isolated using standard molecular biology techniques (Sambrook et al., 1989). The tags are simultaneously sequenced and assigned to genes or ESTs. The abundance of these tags is given a number value that is normalized to parts per million (PPM) which then allows the tag expression, or tag abundance, to be compared across different tissues. Genome wide gene expressions can be profiled simultaneously using this technology. Since each 17 base tag is long enough to be specific to only one or a few genes in any genome, the MPSS platform can be used to determine the expression pattern of a particular gene and its expression levels in different tissues.

MPSS gene expression profiles were generated from different soybean tissues over time, and the profiles were accumulated in a searchable database. PSO400258 cDNA sequence SEQ ID NO:17 was used to search the MPSS database to identify a MPSS tag sequence (SEQ ID NO:22) that is identical to a 17 base pair region from position 523 to 539 in the 3'UTR (3' untranslated region) of PSO400258 cDNA sequence. The identified MPSS tag was then used to search the MPSS database to reveal its abundance in different soybean tissues. As illustrated in Table 1, the PSO400258 gene was confirmed to be highly abundant in flowers and also detectable in pods and seeds, a desired expression profile for its promoter to be able to express genes in flowers and in developing pods and seeds.

TABLE 1

| Target gene | PSO400258 |
|---|---|
| MPSS tag sequence | SEQ ID NO: 22 |
| Flower | 4319 |
| Pod | 33 |
| Flower bud | 2619 |
| Lateral root | 0 |
| Leaf | 0 |
| Petiole | 0 |
| Primary root | 0 |
| Seed | 316 |
| Stem | 0 |

Example 2

Quantitative RT-PCR Profiles of LTP2 Gene Expression in Soybean

The MPSS profiles of LTP2 gene, i.e. PSO400258, was confirmed and extended by analyzing 14 different soybean tissues using the relative quantitative RT-PCR (qRT-PCR) technique with a 7500 real time PCR system (Applied Biosystems, Foster City, Calif.).

Fourteen soybean tissues (somatic embryo, somatic embryo grown one week on charcoal plate, leaf, leaf petiole, root, flower bud, open flower, R3 pod, R4 seed, R4 pod coat, R5 seed, R5 pod coat, R6 seed, R6 pod coat) were collected from cultivar 'Jack' and flash frozen in liquid nitrogen. The seed and pod development stages were defined according to descriptions in Fehr and Caviness, IWSRBC 80:1-12 (1977). Total RNA was extracted with Trizol reagents (Invitrogen, Carlsbad, Calif.) and treated with DNase I to remove any trace amount of genomic DNA contamination. The first strand cDNA was synthesized with Superscript III reverse transcriptase (Invitrogen).

PCR analysis was performed to confirm that the cDNA was free of genomic DNA. The forward and reverse primers used for PCR analysis are shown in SEQ ID NO:19 and SEQ ID NO:20

The primers are specific to the 5'UTR intron/exon junction region of a soybean S-adenosylmethionine synthetase gene promoter (WO00/37662). PCR using this primer set amplifies a 967 bp DNA fragment from any soybean genomic DNA template and a 376 bp DNA fragment from the cDNA template. The genomic DNA-free cDNA aliquots were used in qRT-PCR analysis of PSO400258 using gene-specific primers SEQ ID NO:23 and SEQ ID NO:24. An endogenous soybean ATP sulfurylase gene was used as an internal control for normalization with primers SEQ ID NO:25 and SEQ ID NO:26 and soybean wild type genomic DNA was used as the calibrator for relative quantification.

The qRT-PCR profiling of the LTP2 gene expression confirmed its predominant flower expression and also showed ongoing expression at levels approximately ten fold lower during early pod and seed development (FIG. 1).

Example 3

Isolation of Soybean LTP2 Promoter

The soybean genomic DNA fragment corresponding to the LTP2 promoter was isolated using a polymerase chain reaction (PCR) based approach called genome walking using the Universal GenomeWalker™ kit from Clontech™ (Product User Manual No. PT3042-1).

Soybean genomic DNA samples were digested, separately, to completion with four restriction enzymes DraI, EcoRV, HpaI, or PmlI, each of which generates DNA fragments having blunt ends. Double strand adaptors supplied in the GenomeWalker™ kit were added to the blunt ends of the genomic DNA fragments by DNA ligase. Two rounds of PCR were performed to amplify the LTP2 corresponding genomic DNA fragment using two nested primers supplied in the Universal GenomeWalker™ kit that are specific to the adaptor sequence (AP1 and AP2, for the first and second adaptor primer, respectively), and two LTP2 gene specific primers (GSP1 and GSP2) designed based on the 5' coding sequence of LTP2 (PSO400258). The oligonucleotide sequences of the four primers are shown in SEQ ID NO:13 (GSP1), SEQ ID NO:14 (AP1), SEQ ID NO:15 (GSP2), and in SEQ ID NO:16 (AP2). The GSP2 primer contains a recognition site for the restriction enzyme NcoI. The AP2 primer from the Universal GenomeWalker™ kit contains a SaII restriction site. The 3' end of the adaptor sequence SEQ ID NO:21 contains a XmaI recognition site downstream to the corresponding SalI restriction site in AP2 primer.

The AP1 and the GSP1 primers were used in the first round PCR using each of the adaptor ligated genomic DNA samples (DraI, EcoRV, HpaI or PmlI) under conditions defined in the GenomeWalker™ protocol. Cycle conditions were 94° C. for 4 minutes; 35 cycles of 94° C. for 30 seconds, 60° C. for 1 minute, and 68° C. for 3 minutes; and a final 68° C. for 5 minutes before holding at 4° C. One microliter from each of the first round PCR products was used as templates for the second round PCR with the AP2 and GSP2 primers. Cycle conditions for second round PCR were 94° C. for 4 minutes; 25 cycles of 94° C. for 30 seconds, 60° C. for 1 minute, and 68° C. for 3 minutes; and a final 68° C. for 5 minutes before holding at 4° C. Agarose gels were run to identify specific PCR product with an optimal fragment length. An approximately 1.8 Kb PCR product was detected and subsequently cloned into pCR2.1-TOPO vector by TOPO TA cloning (Invitrogen). Sequencing of the cloned PCR products revealed that its 3' end matched the 46 bp 5' end of the PSO400258 cDNA sequence, indicating that the PCR product was indeed the corresponding LTP2 genomic DNA fragment. The 1771 bp genomic DNA sequence upstream of the putative LTP2 start codon ATG is herein designated as soybean LTP2 promoter (SEQ ID NO:1), which includes 5 bp GGGAT non-soybean DNA sequence at the 5' end derived from restriction sites used for cloning.

Example 4

LTP2 Promoter Copy Number Analysis

Southern hybridization analysis was performed to determine whether there were other sequences in the soybean genome with high similarity to the LTP2 promoter. Soybean 'Jack' wild type genomic DNA was digested with nine different restriction enzymes BamHI, BglII, DraI, EcoRI, EcoRV, HindIII, MfeI, NdeI, and SpeI, each separately, and distributed in a 0.7% agarose gel by electrophoresis. Each of the digested DNA samples was blotted onto a Nylon membrane and hybridized with digoxigenin (DIG) labeled LTP2 promoter DNA probe according to the standard protocol (Roche Applied Science, Indianapolis, Ind.). The LTP2 promoter probe was labeled by PCR using the DIG DNA labeling kit (Roche Applied Science) with two gene specific primers SEQ ID NO:10 and SEQ ID NO:7 to make a 682 bp probe described in SEQ ID NO:4 covering the 3' half of LTP2 promoter sequence.

Since two restriction enzymes MfeI and NdeI cut both inside and outside of the 682 bp LTP2 probe region, two bands were expected in each digestion if LTP2 promoter is a single copy sequence (FIG. 2B). A 515 bp band (between two MfeI sites) and an unknown size band were expected for MfeI digestion. A 1022 bp (between two NdeI sites) and an unknown size band were expected for NdeI digestion. The unknown size bands in both MfeI and NdeI digestions would be weaker than the bands in other digestion lanes since only a 190 bp or a 179 bp portion, respectively after each digestion, would be hybridized by the LTP2 probe. In agreement with the analysis, a weak band was detected in MfeI, or NdeI digestion lane (FIG. 2A). The expected 515 bp MfeI band and 1022 bp NdeI were not retained on the Southern blot since any band smaller than ~1 Kb would run out of the agarose gel under the experiment conditions in order to get better separation of digested genomic DNA.

Since seven of the above nine restriction enzymes BamHI, BglII, DraI, EcoRI, EcoRV, HindIII, and SpeI did not cut inside the LTP2 probe region as illustrated in FIG. 2B, a single band was expected to be hybridized by the LTP2 probe in each of the lanes if the LTP2 promoter sequence had only one copy in soybean genome. As expected, a single band was detected in lanes loaded with DNA digested, respectively, with five restriction enzymes BamHI, DraI, EcoRI, EcoRV, and HindIII (FIG. 2A) supporting a single copy LTP2. Two bands were detected in BglII and SpeI digestion lanes, which may be due to partial digestion of the DNA.

Example 5

LTP2:YFP Reporter Constructs and Soybean Transformation

The cloned LTP2 promoter PCR fragment described in EXAMPLE 3 was digested with NcoI, gel purified using a DNA gel extraction kit (Qiagen, Valencia, Calif.) and cloned into the NcoI site of a Gateway cloning ready vector QC299 (FIG. 3 and SEQ ID NO:38) containing a promoter-less fluorescent reporter gene ZS-YELLOW1 N1 (YFP) to make the reporter construct QC301 (SEQ ID NO:39) with the soybean LTP2 promoter driving the YFP gene expression (FIG. 3). Clones with correct orientation of the LTP2 promoter relevant to the YFP gene were selected by double restriction enzymes digestion with MfeI and XbaI. The LTP2:YFP expression cassette in construct QC301 was linked to the SAMS:ALS (S-adenosyl methionine synthetase:acetolactate synthase) expression cassette in construct PHP25224 (FIG. 3 and SEQ ID NO:40) by Gateway cloning to create construct QC303 (FIG. 3 and SEQ ID NO:41). The linked LTP2:YFP and SAMS:ALS cassettes were released as a 6844 bp DNA fragment from construct QC303 by AscI restriction digestion, separated from the vector backbone fragment by agarose gel electrophoresis, and purified from the gel using a Qiagen DNA gel extraction kit. The purified DNA fragment was used to transform soybean cultivar Jack using the particle gun bombardment method (Klein et al., Nature 327:70-73 (1987); U.S. Pat. No. 4,945,050) to study the LTP2 promoter activity in stably transformed soybean plants.

Soybean somatic embryos from the Jack cultivar were induced as follows. Cotyledons (smaller than 3 mm in length) were dissected from surface-sterilized, immature seeds and were cultured for 6-10 weeks under fluorescent light at 26° C. on a Murashige and Skoog media ("MS media") containing 0.7% agar and supplemented with 10 mg/ml 2,4-dichlorophenoxyacetic acid (2,4-D). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (helium retrofit) (Bio-Rad Laboratories, Hercules, Calif.). To 50 µl of a 60 mg/ml 1.0 mm gold particle suspension were added (in order): 30 µl of 10 ng/µl LTP2:YFP+SAMS:ALS DNA fragment, 20 µl of 0.1 M spermidine, and 25 µl of 5 M CaCl$_2$. The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each 5 µl of the DNA-coated gold particles was then loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 100 ng/ml chlorsulfuron as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 100 ng/ml chlorsulfuron selection agent to increase mass. The embryogenic suspension cultures were then transferred to solid agar MS media plates without 2,4-D supplement to allow somatic embryos to develop. A sample of each event was collected at this stage for PCR and quantitative PCR analysis.

Cotyledon stage somatic embryos were dried-down (by transferring them into an empty small Petri dish that was seated on top of a 10 cm Petri dish to allow slow dry down) to mimic the last stages of soybean seed development. Dried-down embryos were placed on germination solid media, and transgenic soybean plantlets were regenerated. The transgenic plants were then transferred to soil and maintained in growth chambers for seed production.

Genomic DNA was extracted from somatic embryo samples and analyzed by quantitative PCR using the 7500 real time PCR system (Applied Biosystems) with gene-specific primers and 6-carboxyfluorescein (FAM)-labeled fluorescence probes to check copy numbers of both the SAMS:ALS expression cassette and the LTP2:YFP expression cassette. The qPCR analysis was done in duplex reactions with a heat shock protein (HSP) gene as the endogenous control and a transgenic DNA sample with a known single copy of SAMS:ALS or YFP transgene as the calibrator using the relative quantification methodology. The endogenous control HSP probe was labeled with VIC (Applera Corporation, Norwalk, Conn.) and the target gene SAMS or YFP probe was labeled with FAM for the simultaneous detection of both fluorescent probes in the same duplex reactions. The primers and probes used in the qPCR analysis are listed below.

| | |
|---|---|
| SAMS forward primer: | SEQ ID NO: 27 |
| FAM labeled SAMS probe: | SEQ ID NO: 38 |
| SAMS reverse primer: | SEQ ID NO: 29 |
| YFP forward primer: | SEQ ID NO: 30 |
| FAM labeled YFP probe: | SEQ ID NO: 31 |
| YFP reverse primer: | SEQ ID NO: 32 |
| HSP forward primer: | SEQ ID NO: 33 |
| VIC labeled HSP probe: | SEQ ID NO: 34 |
| HSP reverse primer: | SEQ ID NO: 35 |

FAM labeled DNA oligo probes and VIC labeled oligo probes were obtained from Sigma Genosys (The Woodlands, Tex.).

Only transgenic soybean events containing 1 or 2 copies of both the SAMS:ALS expression cassette and the LTP2:YFP expression cassette were selected for further gene expression evaluation and seed production (see Table 2). Events negative for YFP qPCR or with more than 2 copies for the SAMS or YFP qPCR were terminated. YFP expression detection in flowers as described in EXAMPLE 8 is also recorded in the same table.

TABLE 2

| Event ID | YFP qPCR | SAMS qPCR | YFP Expression |
|---|---|---|---|
| 4773.1.11 | 1.60 | 2.17 | − |
| 4773.1.6 | 2.06 | 2.04 | + |
| 4773.1.7 | 0.99 | 0.85 | + |
| 4773.2.10 | 1.93 | 2.13 | + |
| 4773.2.11 | 1.05 | 0.89 | + |
| 4773.2.2 | 0.81 | 0.63 | + |
| 4773.2.3 | 1.73 | 2.11 | + |
| 4773.2.8 | 1.00 | 1.13 | + |
| 4773.3.4 | 0.88 | 0.77 | − |
| 4773.4.2 | 1.06 | 0.95 | + |
| 4773.5.1 | 0.99 | 1.10 | + |
| 4773.5.3 | 1.00 | 0.97 | + |
| 4773.6.2 | 0.91 | 0.95 | − |

Example 6

Construction of LTP2 Promoter Deletion Constructs

To define the transcriptional elements controlling the LTP2 promoter activity, five 5' unidirectional deletion fragments SEQ ID NO:2 of 1384 bp, SEQ ID NO:3 of 988 bp, SEQ ID NO:4 of 682 bp, SEQ ID NO:5 of 393 bp, and SEQ ID NO:6 of 224 bp were made by utilizing PCR amplification and the full length soybean LTP2 promoter contained in the original construct QC301 (FIG. 3) as DNA template. The same antisense primer (SEQ ID NO:7) was used in the amplification of all the five LTP2 promoter fragments by pairing with different sense primers SEQ ID NOs: 8, 9, 10, 11, and 12 respectively, to produce the promoter fragments represented by SEQ ID NOs: 2, 3, 4, 5, and 6.

Each of the PCR amplified promoter DNA fragments was cloned into the Gateway cloning ready TA cloning vector pCR8/GW/TOPO (Invitrogen, Carlsbad, Calif.; FIG. 4 and SEQ ID NO:42) and clones with the insert in correct orientation, relative to the Gateway recombination sites attL1 and attL2 in the pCR8/GW/TOPO vector, were selected by MfeI and XbaI double restriction enzymes digestion analysis or sequence confirmation (see the example map QC300-1 (SEQ ID NO:43) in FIG. 4, which contains the 1384 LTP2 promoter deletion fragment SEQ ID NO:2). The maps of constructs QC300-2, QC300-3, QC3004, and QC300-5 containing the LTP2 promoter deletion fragments SEQ ID NOs:3, 4, 5, and 6 were similar. The promoter fragment in the right orientation was subsequently cloned into the Gateway destination vector QC330 (FIG. 4 and SEQ ID NO:44) by Gateway LR clonase reaction (Invitrogen) to place the promoter fragment in front of the reporter gene YFP (see the example map QC300-1Y (SEQ ID NO:45) in FIG. 4, which contains the 1384 LTP2 promoter deletion fragment SEQ ID NO:2). A 21 bp Gateway recombination site attB2 (SEQ ID NO:37) was inserted between the promoter and the YFP reporter gene coding region as a result of the Gateway cloning process. Another 21 bp Gateway recombination site attB1 (SEQ ID NO:36) was left at the 5' end of the LTP2 promoter. The maps of constructs QC300-2Y (SEQ ID NO:46), QC300-3Y (SEQ ID NO:47), QC300-4Y (SEQ ID NO:48), and QC300-6Y (SEQ ID NO:49) containing the LTP2 promoter deletion fragments SEQ ID NOs: 3, 4, 5, and 6 were similar.

The LTP2:YFP promoter deletion constructs QC300-1Y, QC300-2Y, QC300-3Y, QC300-4Y, and QC300-5Y were ready to be transformed into germinating soybean cotyledons by gene gun bombardment method for transient gene expression study. The 1771 bp full length LTP2 promoter in construct QC301 was included as a positive control for transient expression analysis. A simple schematic description of the five LTP2 promoter deletion fragments can be found in FIG. 5.

Example 7

Transient Expression Analysis of LTP2:YFP Constructs

Full length LTP2 promoter construct QC301 and its series deletion constructs QC301-1Y, 2Y, 3Y, 4Y, and 5Y were tested by the YFP gene transient expression assay using germinating soybean cotyledons as the target tissue. Soybean seeds were rinsed with 10% Tween 20 in sterile water, surface-sterilized with 70% ethanol for 2 minutes and then by 6% sodium hypochloride for 15 minutes. After rinsing, the seeds were placed on wet filter paper in a Petri dish to germinate for 4-6 days under fluorescent light at 26° C. Green cotyledons were excised and placed inner side up on a 0.7% agar plate containing MS media for particle gun bombardment.

The DNA and gold particle mixtures were prepared similarly as described in EXAMPLE 5 except with more DNA (100 ng/µl). The bombardments were also carried out under similar parameters as described in EXAMPLE 5. YFP expression was checked under a Leica MZFLIII stereo microscope equipped with UV light source and appropriate light filters (Leica Microsystems Inc., Bannockburn, Ill.), and all microscopic pictures were taken under the same camera settings: 1.06 gamma, 0.0% gain, and 0.58 second exposure approximately 24 hours after bombardment with 8× magnification.

The 1771 bp full length LTP2 promoter construct QC301 expressed but much less than the positive control construct pZSL90 (SEQ ID NO:50), which contained a strong constitutive promoter SCP1 (U.S. Pat. No. 6,072,050), in transient expression assay as shown by the different size green dots (FIGS. 6A, H). Each dot represented a single cotyledon cell which appeared larger if the fluorescence was strong or smaller if the fluorescence was weak, even under the same magnification. The QC301-1Y construct containing the 1384 bp truncated LTP2 promoter fragment and with the attB2 Gateway recombination site (Invitrogen) inserted between the LTP2 promoter and the YFP had weaker expression than the full length LTP2 promoter (FIG. 6B). But a shorter 988 bp LTP2 promoter fragment construct QC301-2Y somehow restored its expression to a similar level as the full length LTP2 promoter (FIG. 6C). One explanation could be that a negative regulatory element present in QC301-1Y was removed in QC301-2Y by more truncation of the promoter. The 682 bp truncated LTP2 promoter construct QC300-3Y had similar expression as the 1384 bp truncation construct QC301-1Y (FIG. 6D). Further truncation of the LTP2 promoter to 393 bp in construct QC301-4Y dramatically reduced the promoter activity as indicated by the fewer and smaller fluorescence dots (FIG. 6E). But even when the LTP2 promoter was truncated to the 224 bp minimal size in construct QC301-5Y, the promoter fragment still retained very low level activity with only a few faint green dots barely detectable (FIG. 6F). A promoter-less construct QC299 (FIG. 3) was used as a negative control in which not a single dot was detected (FIG. 6G). This suggests that the very faint dots shown in FIG. 6F by construct QC301-5Y resulted from the minimal 224 bp LTP2 promoter.

Example 8

LTP2:YFP Expression in Stable Transgenic Soybean Plants

YFP gene expression was checked at different stages of transgenic plant development for yellow fluorescence emission under a Leica MZFLIII stereo microscope equipped with UV light source and appropriate light filters (Leica Microsystems Inc., Bannockburn, Ill.). No specific yellow fluorescence was detected during somatic embryo development or in vegetative tissues such as leaf, petiole, stem, or root of transgenic plant, or in very young flower bud when flower structure had not formed. Fluorescence was only detected in flower buds and flowers.

A soybean flower consists of five sepals, five petals including one standard large upper petal, two large side petals, and two small fused lower petals called kneel to enclose ten stamens and one pistil. The filaments of the ten stamens fuse together to form a sheath to enclose the pistil and separate into 10 branches only at the top to each bear an anther. The pistil consists of a stigma, a style, and an ovary in which there are normally 24 ovules that will eventually develop into seeds.

Specific fluorescence signal (green color) was first detected in the petals of flower bud (FIGS. 7A, B). In older flower bud and open flower when the pistil and stamens fully developed, fluorescence was detected in fused filaments and the style part of pistil (FIGS. 7C, D). No specific fluorescence was detected in the ovary part of pistil or in anthers. The yellow color in anthers was more likely non-specific background as revealed more clearly in FIG. 7D, and FIG. 7I. The yellow auto fluorescence in anthers was even stronger under a non-specific UV light filter while YFP-specific greenish fluorescence disappeared under the same non-specific filter. Similarly, no specific fluorescence was clearly detected in either pollen grains still attached to anthers (FIG. 7I) or in mature pollen grains (white arrow) attached to the style (FIG. 7E).

One unique expression pattern of the LTP2 promoter was that specific fluorescence was detected as a stripe in the inner wall of an open pistil (FIG. 7F). It seemed that the stripe consisted of a thin layer of structure to which ovules were attached. When an ovule (white arrow) was detached from the stripe, the fluorescence came off together with the ovule and left a red non-fluorescent spot in the stripe (FIG. 7F). Though the stripe was not structurally distinct from other parts of the inner pistil wall, it might have unique functions because of the highly specialized expression of the LTP2 gene in the stripe. No fluorescence was detected in other parts of the inner ovary wall, the outer ovary surface, or even the distal part of ovules. When ovule was developing into immature seed, fluorescence was concentrated in the funiculus, the tissue connecting developing seed to ovary wall (FIG. 7G). In older but still green seed, fluorescence spread to the seed coat while maintaining the high concentration at the connecting tissue (FIG. 7H), but fluorescence was never detected in the embryo (FIG. 7J).

In conclusion, the LTP2:YFP expression was only detected in petals, filaments, style, a stripe in the ovary inner wall, funiculus, and seed coat. Ten out of 13 transgenic events expressed YFP in the same manner as described in details above (Table 2). The other three events contained the transgene as revealed by qPCR but failed to express YFP.

What is claimed is:

1. A recombinant DNA construct comprising
a nucleotide sequence comprising any one of the sequences set forth in SEQ ID NO:1, SEQ ID NO:2, SEQ ID NO:3, SEQ ID NO:4, SEQ ID NO:5 or SEQ ID NO:6
operably linked to at least one heterologous sequence,
wherein said nucleotide sequence is a flower-specific promoter.

2. The recombinant DNA construct of claim 1 wherein the heterologous sequence encodes a gene involved in anthocyanin biosynthesis, a gene involved in the synthesis of fragrant fatty acid derivatives, a gene that is determinative of flower morphology, or a gene involved in biosynthesis of plant cytokinin.

3. The recombinant DNA construct of claim 2, wherein the gene involved in anthocyanin biosynthesis is dyhydroflavonol 4-reductase, flavonoid 3,5-hydroxylase, chalcone synthase, chalcone isomerase, flavonoid 3-hydroxylase, anthocyanin synthase, or UDP-glucose 3-O-flavonoid glucosyl transferase.

4. The recombinant DNA construct of claim 2, wherein the gene involved in the synthesis of fragrant fatty acid derivatives is S-linalool synthase, acetyl CoA:benzylalcohol acetyltransferase, benzyl CoA:benzylalcohol benzoyl transferase, S-adenosyl-L-methionine:benzoic acid carboxyl methyl transferase, mycrene synthase, (E)-β-ocimene synthase, orcinol O-methyltransferase, or limonene synthase.

5. The recombinant DNA construct of claim 2, wherein the gene that is determinative of flower morphology is AGAMOUS, APETALA, or PISTILLATA.

6. The recombinant DNA construct of claim 2, wherein the gene involved in biosynthesis of plant cytokinin is isopentenyl transferase.

7. A vector comprising the recombinant DNA construct of claim 1.

8. A cell comprising the recombinant DNA construct of claim 1.

9. The cell of claim 8, wherein the cell is a plant cell.

10. A transgenic plant having stably incorporated into its genome the recombinant DNA construct of claim 1.

11. The transgenic plant of claim 10, wherein the plant is a flowering plant.

12. The transgenic plant of claim 11, wherein the flowering plant is rose, carnation, Gerbera, Chrysanthemum, tulip, Gladioli, Alstroemeria, Anthurium, lisianthus, larkspur, irises, orchid, snapdragon, African violet, or azalea.

13. A transgenic seed produced by the transgenic plant of claim 10, wherein the transgenic seed comprises the recombinant DNA construct.

14. A method of expressing a coding sequence or a functional RNA in a flowering plant comprising:
   a) introducing the recombinant DNA construct of claim 1 into the plant, wherein the at least one heterologous sequence comprises a coding sequence or encodes a functional RNA;
   b) growing the plant of step a); and
   c) selecting a plant displaying expression of the coding sequence or the functional RNA of the recombinant DNA construct.

15. A method of transgenically altering a marketable flower trait of a flowering plant, comprising:
   a) introducing a recombinant DNA construct of claim 1 into the flowering plant;
   b) growing a fertile, mature flowering plant resulting from step a); and
   c) selecting a flowering plant expressing the at least one heterologous sequence in flower tissue based on the altered marketable flower trait.

16. The method of claim 15 wherein the marketable flower trait is color, morphology, or fragrance.

* * * * *